US010328159B2

(12) United States Patent
Brahmbhatt et al.

(10) Patent No.: US 10,328,159 B2
(45) Date of Patent: Jun. 25, 2019

(54) ENHANCED LOADING OF INTACT, BACTERIALLY DERIVED VESICLES WITH SMALL MOLECULE COMPOUNDS

(71) Applicant: EnGeneIC Molecular Delivery Pty Ltd., Lane Cove West, Sydney (AU)

(72) Inventors: Himanshu Brahmbhatt, Sydney (AU); Jennifer MacDiarmid, Sydney (AU)

(73) Assignee: ENGENIC MOLECULAR DELIVERY PTY LTD., Sydney (AU)

( * ) Notice: Subject to any disclaimer, the term of this patent is extended or adjusted under 35 U.S.C. 154(b) by 242 days.

(21) Appl. No.: 14/873,776

(22) Filed: Oct. 2, 2015

(65) Prior Publication Data

US 2016/0095941 A1 Apr. 7, 2016

Related U.S. Application Data

(60) Provisional application No. 62/059,466, filed on Oct. 3, 2014.

(51) Int. Cl.
*A61K 31/706* (2006.01)
*A61K 31/136* (2006.01)
*A61K 47/69* (2017.01)
*A61K 9/50* (2006.01)
*A61K 31/65* (2006.01)

(52) U.S. Cl.
CPC ........ *A61K 47/6901* (2017.08); *A61K 9/5068* (2013.01); *A61K 31/65* (2013.01); *A61K 31/706* (2013.01)

(58) Field of Classification Search
CPC .............................. A61K 47/48; A61K 31/706
See application file for complete search history.

(56) References Cited

U.S. PATENT DOCUMENTS

| | | | |
|---|---|---|---|
| 5,306,809 A | 4/1994 | Boon et al. | |
| 6,521,431 B1 | 2/2003 | Kiser et al. | |
| 7,183,105 B2 | 2/2007 | Sabbadini et al. | |
| 8,449,877 B2 | 5/2013 | Brahmbhatt et al. | |
| 8,470,984 B2 | 6/2013 | Caruso et al. | |
| 8,591,862 B2 | 11/2013 | Brahmbhatt et al. | |
| 8,669,101 B2 | 3/2014 | Brahmbhatt et al. | |
| 2004/0138168 A1* | 7/2004 | Satishchandran ...... | C12N 15/63 514/44 R |
| 2005/0112065 A1 | 5/2005 | Drummond et al. | |
| 2005/0239217 A1* | 10/2005 | Graham ............. | G01N 33/5432 436/528 |
| 2006/0216810 A1 | 9/2006 | Ju | |
| 2009/0253651 A1* | 10/2009 | Norbedo ............. | C08B 37/0072 514/54 |
| 2011/0275585 A1* | 11/2011 | Brahmbhatt ....... | A61K 31/7088 514/34 |
| 2012/0121615 A1 | 5/2012 | Flygare et al. | |
| 2013/0071482 A1 | 3/2013 | Bae et al. | |
| 2013/0261094 A1 | 10/2013 | Rijcken et al. | |

FOREIGN PATENT DOCUMENTS

| | | |
|---|---|---|
| WO | WO1998/02446 | 1/1998 |
| WO | WO2000/67776 | 11/2000 |
| WO | WO2003/033519 A2 | 4/2003 |
| WO | WO2004/082689 * | 9/2004 |
| WO | WO2004/113507 | 12/2004 |
| WO | WO2005/056749 A2 | 6/2005 |
| WO | WO2005/079854 A1 | 9/2005 |
| WO | WO2006/108052 A2 | 10/2006 |
| WO | WO 2008/012695 A2 | 1/2008 |
| WO | WO 2010/009277 A2 | 1/2010 |
| WO | WO 2011/027222 A2 | 3/2011 |
| WO | WO2013/088250 A1 | 6/2013 |
| WO | WO 2014/122232 A1 | 8/2014 |

OTHER PUBLICATIONS

Susanne Paukner et al., Sealed Bacterial Ghosts-Novel Targeting Vehicles for Advanced Drug Delivery of Water-soluble Substances, Journal of Drug Targeting, vol. 11 (3), 151-161. (Year: 2003).*
Barak, "Open Questions about the Function and Evolution of Bacterial Min Systems, *Frontiers in Microbilogy*," Opinion Article, 3 pages (2013).
Britton et al., "Characterization of a prokaryotic SMC protein involved in chromosome partitioning", Genes & Development, 1998, vol. 12, pp. 1254-1259.
Caravella et al., "Design of next-generation protein therapeutics," *Curr. Opin. Chem. Biol.* 14: pp. 520-528 (2010). [Abstract].
Consoli, et al., "Cellular pharmacology of mitoxantrone in p-glycoprotein-positive and -negative human myeloid leukemic cell lines," vol. 11, pp. 2066-2074 (1997).
Da Silva et al., HER3 and downstream pathways are involved in colonization of brain metastases from breast cancer, *Breast Cancer Res.* 12: R46 (1-13) (2010).
Debinski et al., "Molecular Expression Analysis of Restrictive Receptor for Interleukin 13, a Brain Tumor-associated Cancer/Testis Antigen," *Mol. Med.* 6: 440-449 (2000).
De Boer et al., "Roles of MinC and MinD in the Site-Specific Septation Block Mediated by the MinCDE System of *Escherichia coli*", Journal of Bacteriology, 1992, vol. 174, No. 1, pp. 63-70.
Ducry, et al., "Antibody-drug conjugates: linking cytotoxic payloads to monoclonal antibodies," Bioconjugate Chem., vol. 21, pp. 5-13 (2013).
Duncan, "Polymer Conjugates as Anticancer Nanomedicines," Nature Reviews Cancer, vol. 6, pp. 688-701 (2006).
Gajate, et al., "Antitumor alkyl-lysophospholipid analog adelfosine induces apoptosis in pancreatic cancer by targeting endoplasmic reticulum," Oncogene 31, pp. 2627-2639 (2012) [Abstract].
Goh et al., "Endocytosis of Receptor Tyrosine Kinases," *Cold Spring Harb. Perspect. Biol.* 5: a017459, 17 pages (2013).

(Continued)

*Primary Examiner* — Michael G. Hartley
*Assistant Examiner* — Jagadishwar R Samala
(74) *Attorney, Agent, or Firm* — Foley & Lardner LLP

(57) ABSTRACT

Enhanced loading of small molecule compounds into intact, bacterially derived vesicles provides operational and therapeutic advantages.

12 Claims, 24 Drawing Sheets

(56) References Cited

OTHER PUBLICATIONS

Harry, "Bacterial cell division: regulating Z-ring formation", Molecular Microbiology, 2001, vol. 40, No. 4, pp. 795-803.
Hershey, "IL-13 receptors and signaling pathways: an evolving web," *J. Allergy Clin. Immunol.*, vol. 111, pp. 677-690 (2003).
Hiraga et al., "Chromosome Partitioning in *Escherichia coli*: Novel Mutants Producing Anucleate Cells", Journal of Bacteriology, 1989, vol. 171, No. 3, pp. 1496-1505.
Hu et al., "Topological regulation of cell division in *Escherichia coli* involves rapid pole to pole oscillation of the division inhibitor MinC under the control of MinD and MinE", Molecular Microbiology, 1999, vol. 34, No. 1, pp. 82-90.
Husseini, "Folic Acid Quenches Doxorubicin Fluorescence," Adv. Sci. Lett. 7: p. 726 (2012).
Ireton et al., "spo0J Is Required for Normal Chromosome Segregation as well as the Initiation of Sporulation in *Bacillus subtilis*", Journal of Bacteriology, 1994, vol. 176, No. 17, pp. 5320-5329.
Jarboe et al., "Expression of Interleukin-13 Receptor α2 in Glioblastoma Multiforme: Implications for Targeted Therapies," Cancer Res. 67: 7983-7986 (2007).
Lemmon et al., "Cell signaling by receptor-tyrosine kinases," *Cell* 141(7): 1117-134 (2010).
MacDiarmid, et al., "Bacterially derived 400 nm particles for encapsulation and cancer cell targeting of chemotherapeutics", Cancer Cell, 11: 431-445, (2007).
Mollinedo et al., "Involvement of lipid rafts in the localization and dysfunction effect of the antitumor ether phospholipid edelfosine in mitochondria," Cell Death and Disease, vol. 2, 9 pages (2011).
Nicoletti et al., "N-(2-hydroxypropyl)methacrylamide-amphotericin B (HPMA-AmB) copolymer conjugates as antileishmanial agents," vol. 33, pp. 441-448 (2009).
Nie et al., "pH-Responsive Polymers for Delivery of Nucleic Acid Therapeutics," *Polymeric Biomaterials: Medicinal and Pharmaceutical Applicaitons*, Chapter 16, pp. 413-432 (2013).
Okada et al., "Cytoplasmic Axial Filaments in *Escherichia coli* Cells: Possible Function in the Mechanism of Chromosome Segregation and Cell Division", Journal of Bacteriology, pp. 917-922 (1994).
Okano et al., Total Synthesis of (+)-Yatakemycin, J. Am. Chem. Soc., vol. 128, No. 22, pp. 7136-7137 (2006).
Raskin et al., "MinDE-Dependent Pole-to-Pole Oscillation of Division Inhibitor MinC in *Escherichia coli*", Journal of B acteriology, vol. 181, No. 20, Oct. 1999, pp. 6419-6424.
Reeve et al. "Bacteriophage SPO1-Induced Macromolecular Synthesis in Minicells of Bacillus subtillis", Journal of Virology, vol. 15, No. 6, Jun. 1975, pp. 1308-1316.
Smith et al., "Subcellular Distribution of the Anticancer Drug Mitoxantrone in Human and Drug-resistant Murine Cells Analyzed by Flow Cytometry and Confocal Microscopy and Its Relationship to the Induction of DNA Damage," Cancer Res., vol. 52, pp. 4000-4008 (1992).
Stewart et al., "Genetic and Morphological Characterization of an *Escherichia coli* Chromosome segregation Mutant", Journal of Bacteriology, Jul. 1992, vol. 174, No. 13, pp. 4513-4516.
Tanpure et al., "Synthesis of structurally diverse benzosuberene analogues and their biological evaluation as anti-cancer agents," *Bioorg. Med. Chem.* 21 8019-8032 (2013).
Tietze et al., Synthesis, Biological Evaluation, and Live Cell Imaging of Novel Fluorescent Duocarmycin Analogs, *Chem. Biodivers.*, vol. 9, No. 11, pp. 2559-2570 (2012).
Wykosky et al., "Interleukin-13 Receptor α2, EphA2, and Fos-Related Antigen 1 as Molecular Denominators of High-Grade Astrocytomas and Specific Targets for Combinatorial Therapy," *Clin Cancer Res.* 14: 199-208 (2008).
International Preliminary Report on Patentability issued in related International Patent Application No. PCT/IB2015/057558, dated Apr. 13, 2017.
Extended Search Report issued in co-pending European Patent Application No. 15846818.1, dated Apr. 30, 2018.
MacDiarmid, et al., Bacterially-derived nanocells for tumor-targeted delivery of chemotherapeutics and cell cycle inhibitors, *Cell Cycle Landes Biosciences*, vol. 6, No. 17, pp. 2099-2105 (Sep. 2007).
Najme Sadat Hosseini Motlagh, et al., "Fluorescence properties of several chemotherapy drugs: doxorubicin, paclitaxel and bleomycin," Biomedical Optics Express, vol. No. 6, p. 2400, May 2016).
Search Report issued in co-pending Singapore Patent Application No. 11201702627U, dated May 21, 2018.
Quintieri et al., "Formation and Antitumor Activity of PNU-159682, A Major Metabolite of Nemorubicin in Human Liver Microsomes," *Clin. Cancer Research*, vol. 11, pp. 1608-1617 (Feb. 2005).

* cited by examiner

ENHANCED LOADING OF INTACT, BACTERIALLY DERIVED VESICLES WITH SMALL MOLECULE COMPOUNDS

CROSS-REFERENCE TO RELATED APPLICATION

This application claims priority from U.S. Provisional Patent Application No. 62/059,466, filed Oct. 3, 2014. The contents of this application is incorporated herein by reference in its entirety.

BACKGROUND

Non-living but intact bacterial vesicles that enclose biologically active agents have been used for therapeutic purposes. In international patent application WO2003/033519, for instance, the present inventors described the preparation and use of bacterially derived intact minicells that contain therapeutic nucleic acid molecules. By way of WO2005/079854, the present inventors also showed that small molecular drugs, whether hydrophilic or hydrophobic, can be packaged into minicells which, when taken up by a target mammalian cell, can release the drugs into the cytoplasm of the target cell. Likewise, U.S. Pat. No. 8,591,862 lists the present inventors and demonstrates the preparation and use of intact killed bacterial cells packaged with therapeutic agents.

Killed bacterial cells by definition are nonliving, as are minicells. Neither type of intact bacterial vesicle can replicate or actively invade host cells.

The present inventors have reported that killed bacterial cells and minicells, despite their relatively large size, can be taken up by a target mammalian cell, when brought into contact with the cell, and then degraded in late-endosomes/lysosomes, releasing their drug payload into the target cell. Uptake is improved when the killed bacterial cells or minicells are attached to a ligand that targets the mammalian cell. Illustrative of such a ligand, described in WO2005/056749, is a bispecific antibody that has (i) a first arm with specificity for a minicell surface structure and (ii) a second arm with specificity for a non-phagocytic mammalian cell surface receptor.

The present inventors also discovered that, upon intravenous administration to a tumor-bearing mammalian host, minicells rapidly extravasated via the leaky vasculature associated with many solid tumors, including certain brain tumors (WO2013/088250), and the minicells accumulated in the tumor microenvironment. That the minicells were confined to the tumor microenvironment and did not penetrate into normal tissues is believed to be due to an inability of the minicells, with a diameter of ~400 nm±50 nm, to escape from the normal vasculature surrounding normal (non-tumor) tissues.

In addition, the present inventors described methodology for loading drug payloads into such bacterial vesicles. For instance, nucleic acids can be packaged into an intact nonliving bacterial vesicle when incubated with the vesicle under a concentration gradient, during which the nucleic acids move down the gradient into the vesicle. See, e.g., U.S. Pat. No. 8,669,101. Alternatively, a plasmid that encodes a nucleic acid can be transduced into a live bacterium and replicate or transcribe to produce the nucleic acid. The nucleic acid-packaged live bacterium then can be killed, yielding a killed bacterial cell as described above, or it can generate an intact minicell, itself loaded with the nucleic acid. See, e.g., WO2003/033519.

Unlike nucleic acids, small molecule drugs typically cannot be produced from a plasmid. As noted, however, the present inventors discovered that such drugs can be loaded into a vesicle directly. Their approach to loading small molecule drugs was illustrated in experiments reported by MacDiarmid et al., *Cancer Cell* 11: 431-5 (2007).

For the experiments reported in that 2007 disclosure, drug loading was effected with minicells contained in 1 to 2 milliliters (ml) of phosphate-buffered saline ("PBS buffer"), which has the composition: 137 mM NaCl, 2.7 mM KCl, 10 mM $Na_2PO_4$, 2 mM $KH_2PO_4$ (adjusted to pH 7.4). See P. Gerhardt, et al., MANUAL OF METHODS FOR GENERAL BACTERIOLOY, 2nd ed., American Society for Microbiology (Washington, D.C.), 1981. On this 1 ml-to-2-ml scale (hereafter, "small scale"), co-incubation of the minicells with a given drug was followed by an effort to remove excess drug from the minicells. This effort entailed centrifugation, thereby to pellet the drug-packaged minicells, and a subsequent discarding of the supernatant, where any excess drug was thought to reside. The minicells then were resuspended in fresh PBS, again 1 to 2 ml, and the steps of centrifugation and supernatant discarding were repeated five to six times for a given preparation. In the present disclosure this conventional process is referred to as "the small-scale protocol," which entails the co-incubation (loading) step and multiple steps of washing by resuspension, centrifugation and supernatant discarding, all performed in a 1-to-2-ml scale.

As follow-up to implementing the small-scale protocol, MacDiarmid et al. extracted drug that was associated with the minicells, see the last full sentence on page 433 ff., whereupon the drug concentration was determined using HPLC analysis. For several anticancer drugs MacDiarmid et al. reported an estimated loading efficiency for the small-scale process in terms, for instance, of "~10 million . . . molecules . . . per minicell" of doxorubicin. Id., first full sentence of page 435.

SUMMARY OF THE INVENTION

By further investigation the present inventors have discovered that, when incubated with a nonliving, intact bacterial vesicle that initially does not contain a given fluorescent compound, the latter can move down the resultant concentration gradient (high outside to low inside) into the cytoplasm of the vesicle unexpectedly more quickly than an otherwise similar but non-fluorescent compound, and also that the fluorescent compound can achieve a surprisingly higher intra-vesicular concentration. Along these lines the inventors observed, for example, that linking a non-fluorescent compound with a fluorescent moiety greatly improves loading into nonliving, intact bacterial vesicles, relative results obtained with the non-fluorescent compound itself, notwithstanding that such modification typically effects an increase in molecular weight, which would have been thought to hamper drug loading.

In relation to the loading of fluorescent compounds particularly, the inventors also have determined that an even greater enhancement of efficiency occurs when the loading of a fluorescent compound is effected in a medium to which has been added a binary ionic compound such as an alkali metal halide salt, e.g., potassium chloride, sodium chloride, and potassium bromide. Pursuant to the invention, the presence in the loading medium of such a compound, in a concentration as low as on the order of about 200 mM, improves loading efficiency for a fluorescent compound by two-fold or more, with loading effectively complete after only about fifteen minutes.

More generally, the inventors found that the centrifugation involved in the small-scale protocol, discussed above, can be eliminated and the small-scale protocol itself replaced, for both fluorescent and non-fluorescent compounds, with a process of co-incubation (loading) followed by multiple steps of washing via cross-flow filtration. See, generally, CROSS FLOW FILTRATION METHOD HANDBOOK (29-0850-76 AB), GE Healthcare, accessed at www.gelifesciences.com/gehds_images/GELS/Related %/20Content/Files/1392028292867/litdoc29085076_201403130459 08.pdf. See also MEMBRANE PROCESSES IN BIOTECHNOLOGY AND PHARMACEUTICS, edited by Catherine Charcosset, Elsevier (2012), and STERILE FILTRATION: A PRACTICAL APPROACH, edited by Maik W. Jorniitz and Theodore H. Meltzer, Taylor & Francis (2000). In accordance with the invention, the cross-flow filtration is conducted with pharmaceutical grade filters, which are available commercially from Sartorius Stedim Systems, GE Healthcare and Pall Corporation, among other suppliers. It is within the purview of those knowledgeable in filtration field to select a suitable filter based on the description in the user's manual provided by the supplier, depending on the size of the filter, the production scale, etc. Additionally, the pore size of the filter is standard, e.g., 0.45 µm or 0.2 µm, depending on the purpose of the filtration. The pressure applied during filtration varies at every step and is adjusted according to the need.

In this context an unexpected advantage was found to pertain when the scale of washing drug-packaged vesicles in buffer was increased, in terms of the volume of buffer employed, by between about four and five orders of magnitude, i.e., on the liter scale (hereafter, "large scale") as compared to the milliliter scale of the small-scale protocol, e.g., by a three-to-five-times repeated washing of drug-loaded vesicles in about 20 liters of fresh buffer per repetition. Pursuant to this approach (hereafter, "the large-scale process"), therefore, on the order of about 100 liters of buffer can be employed, for example, in washing steps for a given batch of drug-loaded vesicles.

Consequently the inventive method yields not only a reduction in free endotoxin levels but also a reduction in a hitherto unrecognized fraction of payload compound that the conventional small-scale protocol leaves trapped on the outer surface of the vesicle. By way of illustration, the small-scale protocol resulted in a number of doxorubicin molecules loaded per intact minicell that MacDiarmid et al. (2007), supra, estimated at about 10 million. With the large-scale process of the present invention, this number is under about 1 million molecules per minicell (see Example 6 below). Thus, the small-scale protocol was associated with the trapping of some 9 million molecules of doxorubicin to the outer layer of the packaged minicells, contrasting markedly with the inventive methodology (see Example 14).

According to the process of the invention, therefore, trapping of a payload compound to the outside of a packaging vesicle is minimized, and loaded compound stays inside the vesicles when the concentration gradient is removed. The invention thus provides a highly effective approach to preparing intact, nonliving bacterial vesicles that enclose loaded compound in amounts on the order of hundreds of nanograms of compound per $10^9$ minicells.

In one aspect, therefore, the present disclosure provides a composition comprising an intact and nonliving bacterial vesicle that encloses a fluorescent small molecule drug, which is not doxorubicin, irinotecan, bisantrene, topotecan, epirubicin, daunorubicin, mitoxantrone, Oregon Green® 488-conjugated paclitaxel, or BODIPY® FL-conjugated vinblastine. The vesicle is either an intact, bacterially derived minicell or a killed bacterial cell. In some embodiments the minicell encloses at least 500,000 molecules of the small molecule drug. Preferably, the small molecule drug is biologically active. In some embodiments the small molecule drug has a molecular weight of about 900 Dalton or less. In other embodiments, the small molecule drug is cytotoxic. Exemplary small molecule drugs include but are not limited to morpholinyl anthracycline derivatives, such as PNU-159682. In certain embodiments the small molecule drug is activated in vivo.

In another aspect, the disclosure provides a composition comprising an intact and nonliving bacterial vesicle that encloses a compound of formula D-L-F or a salt thereof, wherein: D is the residue of a small molecule drug, L is a linker, and F is a fluorescent moiety. The linker suitable for this invention either has a half-life of between 6 hours and 24 hours or is degraded under an acidic pH condition, such as in the endosome of a mammalian cell. Illustrative small molecule drugs, fluorescent moieties, and linkers and the structures thereof are detailed below.

In yet another aspect, a composition is provided that comprises an intact, bacterially derived bacterial vesicle enclosing a compound that comprises an active agent bound through a linker to an energy transfer moiety, wherein the active agent is other than Oregon Green® 488-conjugated paclitaxel and BODIPY® FL-conjugated vinblastine. In some embodiments the energy transfer moiety is a light emitting moiety, comprises a conjugated pi system, or comprises an acridinyl moiety, a xanthenyl moiety, or a benzimidazolyl moiety.

In a related aspect, the invention is directed to a method of loading a plurality of minicells with a desired compound without resort to centrifugation. The method includes the steps of (A) incubating the plurality in a volume of an incubation solution of the desired compound in a buffered liquid, wherein the volume is on the order of about 100 mls or more, and then (B) subjecting the plurality to multiple washing steps, each comprising cross-flow filtration of the minicells with a volume of buffered liquid that is on the order of liters, wherein none of the washing steps employs centrifugation of the minicells. In some embodiments a binary ionic compound, which is different from the desired compound to be loaded within the minicell, is dissolved in the incubation solution to a concentration that is on the order of about 200 mM or more. Preferably, step (B) comprises three to five washing steps. In some embodiments, the desired compound is fluorescent. In some embodiments the incubating of step (A) is for a period of about 4 hours. In some embodiments the desired compound is biologically active. The desired compound can be a small molecule drug having a molecular weight of about 900 Dalton or less. Preferably, the small molecule drug is cytotoxic. The small molecule drug can be activated in vivo. In other embodiments the desired compound is of a formula D-L-F or a salt thereof, where D is the residue of a small molecule drug, L is a linker, and F is a fluorescent moiety. Preferably, the linker has a half-life of between 6 hours and 24 hours or is degraded in the endosome of a mammaline cell.

In yet another aspect, the description relates treating cancer in a patient in need thereof. The treatment comprises administering to the patient an effective amount of a composition encompassed by this invention. In some embodiments the composition comprises a cytotoxic compound.

DETAILED DESCRIPTION

Figure 1:
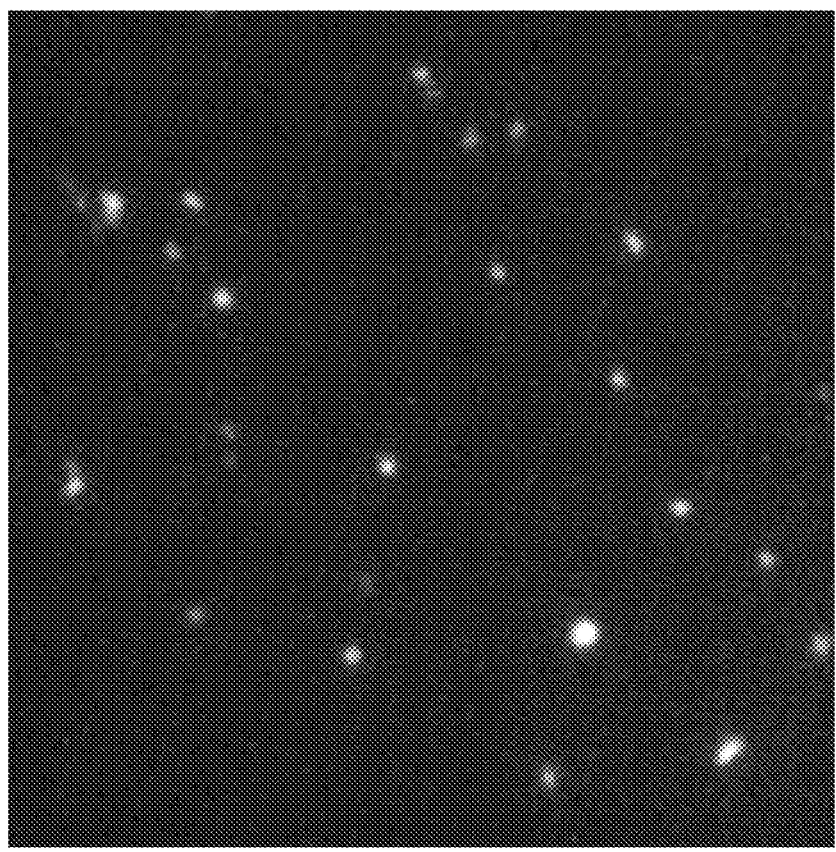
FIG. 1 shows a fluorescent image of minicells packaged with Vinblastine BODIPY® FL. The minicells fluoresce bright red on a black background, indicating that Vinblastine BODIPY® FL is present in the minicells and not in the exterior space.

The present disclosure provides both methodology for loading a compound into intact, bacterially derived, nonliving vesicles, a category inclusive of minicells and killed bacterial cells, and compositions, preferably pharmaceutical grade, that contain such compound-loaded vesicles.

(A) Definitions

Unless defined otherwise, all technical and scientific terms used in this description have the same meaning as commonly understood by those skilled in the relevant art.

For convenience, the meaning of certain terms and phrases employed in the specification, examples, and appended claims are provided below. Other terms and phrases are defined throughout the specification.

The singular forms "a" "an," and "the" include plural reference unless the context clearly dictates otherwise.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, except where the context requires otherwise, the term "comprise" and variations of the term, such as "comprising," "comprises" and "comprised" are not intended to exclude other additives, components, integers or steps.

The phrases "biologically active" and "biological activity" are used to qualify or to denote, as the case may be, the effect(s) of a compound or composition on living matter. Thus, a material is biologically active or has biological activity if it has interaction with or effect on any cell tissue in a human or animal body, e.g., by reacting with protein, nucleic acid, or other molecules in a cell.

"Cancer," "neoplasm," "tumor," "malignancy" and "carcinoma" used interchangeably herein, refer to cells or tissues that exhibit an aberrant growth phenotype characterized by a significant loss of control of cell proliferation. The methods and compositions of this disclosure particularly apply to malignant, pre-metastatic, metastatic, and non-metastatic cells.

"Drug" refers to any physiologically or pharmacologically active substance that produces a local or systemic effect in animals, particularly mammals and humans.

"Individual," "subject," "host," and "patient," terms used interchangeably in this description, refer to any mammalian subject for whom diagnosis, treatment, or therapy is desired. The individual, subject, host, or patient can be a human or a non-human animal. Thus, suitable subjects can include but are not limited to non-human primates, cattle, horses, dogs, cats, guinea pigs, rabbits, rats, and mice.

The terms "treatment," "treating," "treat," and the like refer to obtaining a desired pharmacological and/or physiologic effect in a tumor patient. The effect can be prophylactic in terms of completely or partially preventing tumor growth or a symptom thereof and/or the effect can be therapeutic in terms of a partial or complete stabilization or cure for a tumor and/or for an adverse effect attributable to the tumor. Treatment covers any treatment of a tumor in a mammal, particularly a human. A desired treatment effect can be a tumor response, which can be measured as reduction of tumor mass or inhibition of tumor mass increase. Alternatively or additionally, a desired treatment effect can be an increase of overall patient survival, progress-free survival, time to tumor recurrence, or a reduction of adverse effect.

"Alkyl" refers to a monovalent saturated straight or branched chain linear hydrocarbon group having from 1 to 20, or from 1 to 10, or from 1 to 6, or from 1 to 4 carbon atoms. Examples of alkyl groups include methyl, ethyl, n-propyl, iso-propyl, n-butyl, sec-butyl, tert-butyl, pentyl, hexyl, pentyl or octyl. A $C_1$-$C_4$ straight chained or branched alkyl group is also referred to as a "lower alkyl" group.

"Alkylene" refers to a divalent saturated straight or branched chain linear hydrocarbon group having from 1 to 20, or from 1 to 10, or from 1 to 6, or from 1 to 4 carbon atoms, or 1, or 2 carbon atoms. Examples of alkylene include —$CH_2)_y$—, wherein y is 1, 2, 3, 4, 5, 6, 7, 8, 9 or 10.

"Cycloalkyl" refers to cyclic hydrocarbon group having from 3 to 10, or from 3 to 8 carbon atoms. Examples of cycloalkyl groups include, for instance, adamantyl, cyclopropyl, cyclobutyl, cyclopentyl, cyclooctyl, and cyclohexenyl. "$C_{u-v}$cycloalkyl" refers to cycloalkyl groups having u to v carbon atoms as ring members.

"Heterocycle" or "heterocyclic" or "heterocyclo" or "heterocycloalkyl" or "heterocyclyl" refers to a saturated or partially saturated cyclic group having from 3 to 18 total ring atoms, from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the term "heterocyclic", "heterocycle", "heterocyclo", "heterocycloalkyl" or "heterocyclyl" applies when there is at least one ring heteroatom and the point of attachment is at an atom of a non-aromatic ring (e.g., 1,2,3,4-tetrahydroquinoline-3-yl, 5,6,7,8-tetrahydroquinoline-6-yl, and decahydroquinolin-6-yl). In one embodiment, the nitrogen and/or sulfur atom(s) of the heterocyclic group are optionally oxidized to provide for the N-oxide, sulfinyl, sulfonyl moieties. More specifically the heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

Substituted alkyl, alkylene, cycloalkyl or heterocycle refers to alkyl, alkylene, cycloalkyl or heterocycle, respectively, having 1 to 5 or 1 to 3 substitutes that do not substantially interfere with the anti-cancer activity of the compounds. Examples of substituents on alkyl groups include —OH, —$NH_2$, —$NO_2$, —CN, —COOH, halo, haloalkyl, aryl, heteroayl, alkylaryl, alkoxy, haloalkoxy, —$OR^a$, oxo (=O), —O—$COR^a$, —$COR^a$, —$SO_3H$, —$NHR^a$, —$NR^aR^b$, —$COOR^a$, —CHO, —$CONH_2$, —$CONHR^a$, —$CONR^aR^b$, —$NHCOR^a$, —$NR^cCOR^a$, —$NHCONH_2$, —$NHCONR^aH$, —$NHCONR^aR^b$, —$NR^cCONH_2$, —$NR^cCONR^aH$, —$NR^cCONR^aR^b$, —C(=NH)—$NH_2$, —C(=NH)—$NHR^a$, —C(=NH)—$NR^aR^b$, —C(=$NR^c$)—$NH_2$, —C(=$NR^c$)—$NHR^a$, —C(=$NR^c$)—$NR^aR^b$, —NH—C(=NH)—$NH_2$, —NH—C(=NH)—$NHR^a$, —NH—C(=NH)—$NR^aR^b$, —NH—C(=$NR^c$)—$NH_2$, —NH—C(=$NR^c$)—$NHR^a$, —NH—C(=$NR^c$)—$NR^aR^b$, —$NR^d$—C(=NH)—$NH_2$, —$NR^d$—C(=NH)—$NHR^a$, —$NR^d$—C(=NH)—$NR^aR^b$, —$NR^d$—C(=$NR^c$)—$NH_2$, —$NR^d$—C(=$NR^c$)—$NHR^a$, —$NR^d$—C(=$NR^c$)—$NR^aR^b$, —$NHNH_2$, —$NHNHR^a$, —$NHNR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2R^a$ and —CO-alkyl, wherein $R^a$, $R^b$, $R^c$ and $R^d$ are independently alkyl, haloalkyl, cycloalkyl, phenyl or benzyl. In some embodiments, the substituent(s) are selected from —OH, halo, phenyl, benzyl, pyridyl, and $C_1$-$C_8$ alkoxy. In some embodiments, the substituent(s) are selected from —OH, halo, and $C_1$-$C_4$ alkoxy. Examples of substituents on alkylene, cycloalkyl or heterocycle groups include —OH, —$NH_2$, —$NO_2$, —CN, —COOH, halo, haloalkyl, alkyl, aryl, heteroayl, alkylaryl, alkoxy, haloalkoxy, oxo (=O), —$OR^a$, —O—$COR^a$, —$COR^a$, —$SO_3H$, —$NHR^a$, —$NR^aR^b$, —$COOR^a$, —CHO, —$CONH_2$, —$CONHR^a$, —$CONR^aR^b$, —$NHCOR^a$, —$NR^cCOR^a$, —$NHCONH_2$, —$NHCONR^aH$, —$NHCONR^aR^b$, —$NR^cCONH_2$, —$NR^cCONR^aH$, —$NR^cCONR^aR^b$, —C(=NH)—$NH_2$, —C(=NH)—$NHR^a$, —C(=NH)—$NR^aR^b$, —C(=$NR^c$)—$NH_2$, —C(=$NR^c$)—$NHR^a$, —C(=$NR^c$)—$NR^aR^b$, —NH—C(=NH)—$NH_2$, —NH—C(=NH)—$NHR^a$, —NH—C(=NH)—$NR^aR^b$, —NH—C(=$NR^c$)—$NH_2$, —NH—C(=$NR^c$)—$NHR^a$, —NH—C(=$NR^c$)—$NR^aR^b$, —$NR^d$—C(=NH)—$NH_2$, —$NR^d$—C(=NH)—$NHR^a$, —$NR^d$—C(=NH)—$NR^aR^b$, —$NR^d$—C(=$NR^c$)—$NH_2$, —$NR^d$—C(=$NR^c$)—$NHR^a$, —$NR^d$—C(=$NR^c$)—$NR^aR^b$, —$NHNH_2$, —$NHNHR^a$, —$NHNR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2R^a$ and —CO-alkyl, wherein $R^a$, $R^b$, $R^c$ and $R^d$ are independently alkyl, haloalkyl, cycloalkyl, phenyl or benzyl. In some embodiments, the substituent(s) are selected from —OH, halo, $C_1$-$C_4$ alkyl, phenyl, benzyl, pyridyl, and $C_1$-$C_8$ alkoxy. In some embodiments, the substituent(s) are selected from —OH, $C_1$-$C_4$ alkyl, halogen, and $C_1$-$C_4$ alkoxy.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom. For instance, 5,6,7,8 tetrahydronaphthalene-2-yl is an aryl group, with its point of attachment at the 2-position of the aromatic phenyl ring.

"Substituted aryl" refers to an aryl group which is substituted with 1 to 8 or, in some embodiments, 1 to 5, 1 to 3 or 1 to 2 substituents selected from the group consisting of —OH, oxo (=O), —$NH_2$, —$NO_2$, —CN, —COOH, halo, haloalkyl, alkyl, aryl, heteroaryl, alkylaryl, alkoxy, haloalkoxy, —$OR^a$, —O—$COR^a$, —$COR^a$, —COOH, —$SO_3H$, —$NHR^a$, —$NR^aR^b$, —$COOR^a$, —CHO, —$CONH_2$, —$CONHR^a$, —$CONR^aR^b$, —$NHCOR^a$, —$NR^cCOR^a$, —$NHCONH_2$, —$NHCONR^aH$, —NHCON-$R^aR^b$, —$NR^cCONH_2$, —$NR^cCONR^aH$, —$NR^cCONR^aR^b$, —C(=NH)—$NH_2$, —C(=NH)—$NHR^a$, —C(=NH)—$NR^aR^b$, —C(=$NR^c$)—$NH_2$, —C(=$NR^c$)—$NHR^a$, —C(=$NR^c$)—$NR^aR^b$, —NH—C(=NH)—$NH_2$, —NH—C(=NH)—$NHR^a$, —NH—C(=NH)—$NR^aR^b$, —NH—C(=$NR^c$)—$NH_2$, —NH—C(=$NR^c$)—$NHR^a$, —NH—C(=NR)—$NR^aR^b$, —$NR^d$—C(=NH)—$NH_2$, —$NR^d$—C(=NH)—$NHR^a$, —$NR^d$—C(=NH)—$NR^aR^b$, —$NR^d$—C(=$NR^c$)—$NH_2$, —$NR^d$—C(=$NR^c$)—$NHR^a$, —$NR^d$—C(=$NR^c$)—$NR^aR^b$, —$NHNH_2$, —$NHNHR^a$, —$NHR^aR^b$, —$SO_2NH_2$, —$SO_2NHR$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2R^a$ and —CO-alkyl, wherein $R^a$, $R^b$, $R^c$ and $R^d$ are independently alkyl, cycloalkyl, phenyl or benzyl. In some embodiments, the substituent(s) are selected from —OH, halo, $C_1$-$C_4$ alkyl, phenyl, benzyl, pyridyl, and $C_1$-$C_8$ alkoxy. In some embodiments, the substituent(s) are selected from —OH, $C_1$-$C_4$ alkyl, halogen, and $C_1$-$C_4$ alkoxy.

"Haloalkyl" refers to an alkyl group substituted with 1 to 5 or 1 to 3 halo.

"Alkoxy" refers to the group —O-alkyl wherein alkyl is as defined herein. "Substituted alkoxy" refers to —O-(substituted alkyl).

"Haloalkoxy" refers to the group —O-haloalkyl wherein haloalkyl is as defined herein.

"Halo" refers to —F, —C, —Br or —I.

"Heteroaryl" denotes an aromatic group of from 1 to 14 carbon atoms and 1 to 6 heteroatoms selected from the group consisting of oxygen, nitrogen, and sulfur and includes a 5-to-18-member ring or ring system that includes a single ring (e.g., imidazolyl) or multiple rings (e.g., benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g., 1,2,3,4-tetrahydroquinolin-6-yl and 5,6,7,8-tetrahydroquinolin-3-yl). In one embodiment, the nitrogen and/or the sulfur ring atom(s) of the heteroaryl group are optionally oxidized to provide for the N-oxide (N→O), sulfinyl, or sulfonyl moieties. In some embodiments, the heteroaryl comprises a total of 5, 6 or 7 ring atoms, and is referred to as 5-membered, 6-membered or 7-membered heteroaryl, respectively. Examples of heteroaryl include but is not limited to pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, quinazolinonyl, benzimidazolyl, benzisoxazolyl, or benzothienyl.

"Small-scale protocol" denotes a procedure, exemplified in MacDiarmid et al. (2007), in which bacterially derived vesicles such as minicells are loaded with a therapeutic payload in a buffered liquid, typically PBS buffer, which is on the order of milliliters in volume, e.g., 1 to 2 ml, after which the loaded minicells are subjected to multiple washing steps, involving centrifugation, supernatant discarding and minicell resuspension, again in milliliter volumes of buffered liquid.

By contrast, "large-scale process" refers to methodology of the present invention where loaded minicells are subjected to multiple (e.g., 3 to 5) washing steps in which cross-flow filtration is employed (without centrifugation) with volumes on the order of tens of liters (e.g., about 20 liters) per step of PBS buffer or other buffered liquid suitable for cell biology research, such as HEPES-buffered saline, borate-buffered saline and Tris-buffered saline. In addition, for a large-scale process the step of loading minicells with a therapeutic payload, such as a small molecule drug, is carried out in a volume of buffered liquid that is preferably on the order of about 100 milliliters or more, where the buffered liquid, such as PBS buffer, optionally has a concentration of a binary ionic compound, such as KCl, that is on the order of about 200 mM or more.

The phrase "pharmaceutical grade" denotes a lacking of parental cell contamination, cell debris, free endotoxin and other pyrogens that is sufficient to meet regulatory requirements for human intravenous administration. See, e.g., "Guidance for Industry—Pyrogen and Endotoxins Testing," U.S. Food and Drug Administration (June 2012).

"Residue of a compound" denotes the moiety obtained by removal from a compound of an atom or moiety, such as a hydrogen atom, a —OH, or a —CO—$CH_3$ group. In some embodiments, therefore, a residue of a compound is the moiety obtained by removing a hydrogen atom from a compound.

"Substituted heteroaryl" refers to a heteroaryl group that is substituted with from 1 to 8, or in some embodiments 1 to 5, or 1 to 3, or 1 to 2 substituents selected from the group consisting of the substituents defined for substituted aryl.

"Stereoisomer" and "stereoisomers" denote compound(s) differing in the chirality of one or more stereocenters. Stereoisomers include enantiomers and diastereomers. The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known, as evidenced by the discussion in Chapter 4 of MARCH'S ADVANCED ORGANIC CHEMISTRY, 7th ed. (Wiley, 2013).

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety, such as pyrazoles, imidazoles, benzimidazoles, triazoles, and tetrazoles. By the same token, reference herein to a "compound" includes its tautomers as well.

"Pharmaceutically acceptable salt" refers to pharmaceutically acceptable salts derived from a variety of organic and inorganic counter ions well known in the art and includes, by way of example only, sodium, potassium, calcium, magnesium, ammonium, and tetraalkylammonium. When the molecule contains a basic functionality, acid addition salts of organic or inorganic acids, such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, oxalic acid, 4-toluenesulfonic acid, camphorsulfonic acid, methanesulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Salts also can be formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like. Pharmaceutically acceptable salts are suitable for administration in a patient and possess desirable pharmacological properties. Suitable salts further include those described in HANDBOOK OF PHARMACEUTICAL SALTS: PROPERTIES, SELECTION, AND USE, $2^{nd}$ ed. (Wiley, 2011).

"Payload" in this description identifies or qualifies biologically active material that is to be loaded or that has been loaded into a minicell for delivery to a targeted host cell.

(B) The Inventors' Discoveries and their Surprising Nature

As noted, the inventors discovered that fluorescence per se greatly increases the loading efficiency of a small molecule compound into an intact, nonliving bacterial vesicle. For instance, the examples below show that unmodified paclitaxel can be packaged into a minicell to reach a concentration of 2,115 copies (molecules) per minicell (Example 9), and while a water soluble derivative of paclitaxel, TF.Pac, can reach 50,000 copies per minicell (Example 10), both by co-incubation with the minicells. In contrast, both of two fluorescent derivatives of paclitaxel, FLUTAX-1 and an FITC-conjugated paclitaxel (FCP), can be loaded into minicells to arrive at high concentrations of 270,000 copies (Example 2) and 230,000 copies per minicell (Example 4). These concentrations are higher by 127-fold and 109-fold, respectively, relative to that reached by the unmodified (underivatized), non-fluorescent compound.

Larger molecules would have been expect generally to be harder to load into vesicles than smaller ones because the loading process is believed to entail transiting through membrane channels, where size would impact on movement. Nevertheless, even though FCP (molecular weight: 1455.6 Daltons) is much larger than paclitaxel (molecular weight: 853.9 Daltons), the fluorescent derivative can reach an intra-vesicle concentration that is 109-fold higher than paclitaxel itself. For this reason, too, the inventors' discoveries in this regard are quite surprising.

Possibly due to a small-size advantage in addition to their (auto)fluorescent property, doxorubicin and mitoxantrone reach about 800,000 copies (Example 6) and 759,000 copies per minicell (Examples 12), respectively. Fluorescent compounds BacLight™ Green dye (Example 5), SYTO 9 (Example 7), and 9-AAHH (Example 8) also exhibit high loading efficiency.

Yet another fluorescent conjugate of paclitaxel, Paclitaxel Oregon Green-488, reaches such high concentrations as well (Example 3). A fluorescent derivative of vinblastine, BODIPY® FL, likewise is loaded into minicells with high efficiency, as Example 1 demonstrates. Such loading is not possible with unmodified vinblastine, a fact that was not apparent from the disclosure by MacDiarmid et al. (2007), supra, of using BODIPY® FL-conjugated vinblastine as well as Oregon Green® 488-conjugated paclitaxel to document, by fluorescent microscopy, the loading of minicells with a drug. See FIGS. 1(E) and (F) of MacDiarmid et al. (2007), at page 432 (legend).

Another surprising aspect of the invention is that the high loading efficiency of fluorescent compounds seems unrelated to the hydrophilicity or the hydrophobicity of a given compound. For instance, paclitaxel is hydrophobic while both TF.Pac and FCP are water-soluble, and yet the loading efficiency of FCP is 5-fold greater than that of TF.Pac.

The conjugation point of the fluorescent moiety on the compound appears not to affect the loading efficiency achieved via the present invention. Thus, FCP and FLUTAX-1 have the same fluorescein fluorophore, but its attachment is at the C2' position for FCP rather than at the C7 position, as in FLUTAX-1. Yet both derivatives achieve similar loading efficiency, in terms of final intra-minicell compound concentration.

Example 11 illustrates, moreover, that quenching by folic acid of the doxorubicin fluorescence dose-dependently decreases the loading efficiency of doxorubicin into minicells. This phenomenon further highlights the role of fluorescence per se in enhanced compound loading into minicells, pursuant to the invention.

So far as the inventors are aware, there has been no report of an impact by fluorescence, as such, on the transportation or movement of a chemical compound, especially movement across a cell membrane. Such impact, as documented by the present inventors, may be due to a transfer of energy, between the fluorescent compound and certain molecules in or lining the transmembrane channels, which enhances movement of the compound through the channel. Compared to non-fluorescent compounds, a fluorescent compound contains electrons that are more easily excitable, e.g., by electromagnetic radiation. Such excitation is believed to facilitate energy transfer between a fluorescent compound and some minicell transmembrane channel structure(s), leading to faster movement of the compound in the channel, as well as an increased amount of compound loaded.

Loading methodology according to the invention requires a concentration gradient, i.e., a concentration of compound that is higher extracellularly than intracellularly. As noted, however, the involvement of a fluorescent compound results in loading rates and intra-vesicle concentrations that are greater than what may be explained conventionally in terms of the concentration gradient alone. Thus, as loading into minicells progresses for a fluorescent compound, the intracellular concentration of the compound increases and then surpasses the extracellular concentration, and movement of compound into minicells continues until a de facto saturation is reached. That the presence of ions in the medium potentiates the fluorescence-mediated enhancement of loading intact, bacterially derived vesicles, as Example 13 illustrates, likewise is not an obvious function of the concentration gradient.

In addition, conventional thinking on preparing pharmaceutical grade minicell- and killed bacterial cell-containing compositions was not informed by and did not take into account the trapping on vesicle surfaces of loaded compound that occurs with the small-scale protocol illustrated by MacDiarmid et al. (2007). The present inventors' discovery of the trapping problem brought to light a hitherto unappreciated variable, the leaching of surface-trapped compound (see Example 14), that could influence the effective dose of a payload compound delivered via administration of a minicell- or killed bacterial cell-containing composition, per section (I) below. The large-scale process of the invention, also illustrated in Example 14, allows for controlling this variable by alleviating or even eliminating the trapping problem.

These discoveries and other findings described above were made with intact, bacterially derived minicells, but they are readily extrapolated to killed bacterial cells. This is so because these two types of nonliving bacterial vesicles differ primarily by virtue of size and the presence or absence of a bacterial chromosome. Neither distinction is deemed relevant to the loading efficiency of a compound, which is primarily a function of the bacterial membrane, a feature that is common to both types of bacterial vesicle.

The unexpected findings by the inventors in this regard underscore the surprising nature not only of the methodology described here for loading small molecule compounds into intact, nonliving bacterial vesicles but also of the related compositions and methods for using them, in accordance with the present invention.

(C) Loading Fluorescent Compounds into Intact, Bacterially Derived Vesicles

Compositions therefore are provided that include an intact, nonliving bacterial vesicle enclosing a compound that displays fluorescence. The fluorescence is either (A) intrinsic (autofluorescence) or (B) extrinsic, i.e., fluorescence by virtue of an energy transfer moiety, as defined below, that was introduced chemically beforehand.

The subcategory (A) of autofluorescent compounds in principle encompasses any small molecule compound, as defined below, that intrinsically displays fluorescence upon exposure to a certain wavelength of electromagnetic radiation, typically but not necessarily in the visual spectrum. In accordance with its methodological aspects, the present invention in relation to subcategory (A) contemplates the loading of any autofluorescent compound into an intact, bacterially derived vesicle, including a minicell or a killed bacterial cell, by means of the large-scale process defined above. In accordance with its compositional aspects, the invention in relation to subcategory (A) encompasses compositions comprising intact, bacterially derived vesicles that contain an autofluorescent compound selected from subcategory (A) exclusive of any one or more or all of the following compounds, which were disclosed previously without reference to or implication of the presently described fluorescence effect on vesicle loading: doxorubicin (excitation 480 nm, emission 580 nm); irinotecan, a semisynthetic analogue of camptothecin, with an excitation maximum around 360 nm and an emission maximum at about 440 nm; bisantrene (excitation, 410 nm; emission, 517 nm); topotecan (excitation, 382 nm; emission, 523 nm); epirubicin (excitation, 474 nm; emission, 551 nm); daunorubicin (excitation, 488 nm; emission, 575 nm); and mitoxantrone (excitation, 610 and 660 nm; emission, 684 nm).

Illustrative of the remaining autofluorescent small molecule compounds that are subsumed under the compositional aspects of the invention are: dynemicin A, a natural cyclic enediyne, as well as fluorescent analogues of dynemicin A (see U.S. Pat. No. 5,281,710, the contents of which are incorporated here by reference); acridine orange, with an excitation maximum at 502 nm and an emission maximum at 525 nm (green); and camptothecin, a natural alkaloid with an excitation maximum at 360 nm and an emission maximum at 440 nm. Likewise illustrative are intrinsically fluorescent compounds in the class of morpholinyl anthracycline derivatives described in international patent application WO1998/002446. Among such derivatives are nemorubicin (3'-deamino-3'-[2(S)-methoxy-4-morpholinyl]doxorubicin) a/k/a MMDX, and its major metabolite PNU-159682 (3'-deamino-3"-4'-anhydro-[2"(S)-methoxy 3"(R)-hydroxy-4"-morpholinyl]doxorubicin), the structural formula of which is shown below, as well as these four other such derivatives described in U.S. Pat. No. 8,470,984, the contents of which are incorporated here by reference: 3'-deamino-3"-4'-anhydro-[2"(S)-methoxy-3"(R)-hydroxy-4"-morpholinyl]idarubicin; 3'-deamino-3"4'-anhydro-[2"(S)-methoxy-3"(R)-hydroxy-4"-morpholinyl]daunorubicin; 3'-deamino-3"-4'-anhydro-[2"(S)-methoxy-3"(R)-hydroxy-4"-morpholinyl]-caminomycin; and 3'-deamino-3"-4'-anhydro-[2"(S)-ethoxy-3"(R)-hydroxy-4"-morpholinyl]d-oxorubicin.

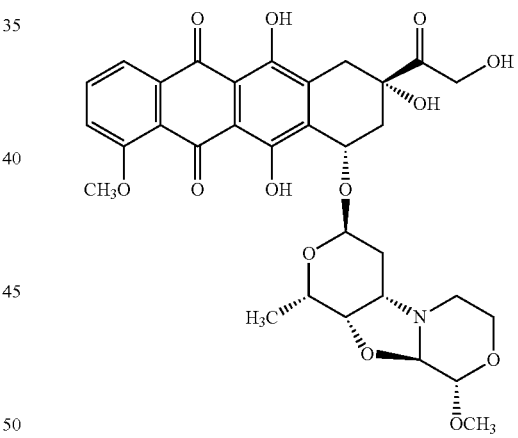

PNU-159682

A pharmaceutically acceptable acid addition salt of any of the aforementioned derivatives also is a member, pursuant to the invention, of this group of autofluorescent morpholinyl anthracycline derivatives.

The subcategory (B) of extrinsically fluorescent compounds encompasses any compound that comprises, inter alia, (i) an active constituent or portion and (ii) an energy transfer moiety, defined below. The active constituent can be a drug or an active part of a drug, to which the energy transfer moiety is added by a derivatization reaction. The result can be a conjugate, where the product of the derivatization reaction incorporates the drug or active part thereof joined, as such, to the energy transfer moiety, with or without a linker; or it can be a structural analog, where the reaction product evinces a structural similarity to the drug or the active part thereof but differs in that one or more atoms, functional groups, or substructures are replaced in the drug or active part with other atoms, groups, or substructures in the structural analog.

In accordance with its methodological aspects, the present invention in relation to subcategory (B) contemplates the loading of any extrinsically fluorescent compound into an intact, bacterially derived vesicle, including a minicell or a killed bacterial cell, by means of the large-scale process. In accordance with its compositional aspects, the invention in relation to subcategory (B) encompasses compositions comprising intact, bacterially derived vesicles that contain an extrinsically fluorescent compound selected from subcategory (B), exclusive of minicell-containing compositions in which the constituent minicells consist of those containing Oregon Green® 488-conjugated paclitaxel or BODIPY® FL-conjugated vinblastine. Such excluded minicell-containing compositions were disclosed by MacDiarmid et al. (2007), supra, without reference to or implication of the presently described effect of fluorescence on transmembrane movement of compounds into such vesicles.

Illustrative of the above-mentioned structural analogs are fluorescent seco-analogs of duocarmycin, a cytotoxic antibiotic, as described by Tietze et al., *Chemistry & Diversity* 9: 2559-70 (2012). Via a reaction scheme involving certain coumarin-carboxylic acids, a trimethoxyindole moiety and (dimethylamino)ethoxyindole moieties of the drug are replaced by a fluorescent molecule, which, like the replaced moieties, interact with DNA. Likewise exemplary of structural analogs within this description are fluorescent analogs of the drug edelfosine (1-O-octadecyl-2-O-methyl-rac-glycero-3-phosphocholine) that, as described in Mollinedo et al., *Cell Death & Dis.* 2: e158 (2011), preserve the pro-apoptotic activity of the drug. See also Gajate et al., *Oncogene* 31: 2627-39 (2012).

In embodiments where a fluorescent conjugate is employed, the linker can have a half-life such that the linker degrades, when the compound is loaded into the vesicle or when a period of time has elapsed or within a range of time thereafter (see below), to release the active constituent of the extrinsically fluorescent conjugate. Alternatively, the linker group can be labile within the target cell. That is, the linker can be subject to thermal, pH-dependent, chemical (e.g., hydrolytic), or enzymatic cleavage, whereupon the active constituent is released into the cell, post-uptake. Such labile linkers have been developed, for instance, in the context of antibody-drug conjugates, and are readily adapted for use in the present invention. See Ducry and Stump, *Bioconjugate Chem.* 21: 5-13 (2010), plus further discussion below.

The above-mentioned "energy transfer moiety" is a group that, upon excitation by electromagnetic radiation of an appropriate wavelength, transfers energy to a nearby energy receptor. The "appropriate" wavelength is any wavelength of electromagnetic radiation that excites electrons in the energy transfer moiety so that they enter an energy level whereby, upon relaxation, the electron either is released from the energy transfer moiety or causes release of electromagnetic radiation from the energy transfer moiety.

Illustrative energy transfer moieties are groups that have a conjugated pi-electron system. Conjugated pi-systems include, for instance, coordination of multiple double bonds, coordination of multiple aromatic groups, coordination of double bonds with aromatic groups, coordination of heterocyclic aromatic groups, and the like. Illustrative energy transfer moieties are acridinyl groups, xanthenyl groups, anthracenyl groups, benzimidazolyl groups, phenanthrenyl groups, pyridinyl groups, quinolinyl groups, and porphorinyl groups.

The energy receptor to which energy is transferred, in keeping with the invention, is believed to be associated with one or more transmembrane structures of the nonliving bacterial vesicle. According to this perspective, when energy transfer is effected from the energy transfer moiety then the transmembrane structure(s) receive(s) the energy transferred, whether via an electron or an emission of light.

Discussed below are different types of compounds that, if they are autofluorescent or extrinsically fluorescent are suitable for loading into the intact, nonliving bacterial vesicles in accordance with the invention. These include but are not limited to the class of biologically active compounds and the subclass of chemotherapeutic compounds, particularly small molecule chemotherapeutic compounds, Many biologically active compounds are not fluorescent. The present disclosure relates an approach for providing a modified (derivatized) form of the given compound, which is fluorescent, for loading such compounds into intact, nonliving bacterial vesicles and, through such vesicles, then for introducing them into a target mammalian cell. While most molecules will be less than about 900 daltons in size, attaching a fluorescent molecule or altering the drug's structure to enhance loading of the drug into minicells, may increase its molecular weight up to about 1500 daltons.

In one aspect, the invention contemplates conjugating a biologically active but non-fluorescent compound with a fluorescent moiety to form a "modified compound" of the formula:

$$D\text{-}L\text{-}F,$$

or a salt thereof, where:
D is the compound or an active constituent thereof,
L is a linker, and
F is a fluorescent moiety.

Such a fluorescent modified compound can be incubated with an intact, nonliving bacterial vesicle under conditions allowing the modified compound to enter the vesicle, pursuant to the invention.

The linker L can be such that the compound or active constituent D is released from the fluorescent moiety F after a period of time or under certain conditions. For example, as noted above the linker can have a half-life in the vesicle such that the linker degrades, sometime after the modified compound is loaded, to release D within the vesicle. Alternatively, the linker L can be stable inside the vesicle but labile in the endosome or lysosome of a mammalian cell. That is, upon uptake by a target mammalian cell and exposure to the environment within the endosomal or lysosomal compartment, the linker degrades under the impact of an environmental factor, such as pH or enzyme action, to release the active constituent in the endosome or lysosome. Examples of such linkers are provided below in Section G.

According to a related aspect the modified compound does not have the biological activity of the unmodified compound and remains in that "inactive" state inside the vesicle. Degradation of the linker in the endosome or lysosome results in release of an active form or species, namely, of active constituent D.

More generally, the fluorescent moiety can be linked to the biologically active compound at a position that partially or completely inhibits the activity of the latter. A biologically active compound typically has one or more external reactive groups that are important for biological activity. Chemical modification or derivatization of these reactive groups can reduce or even eliminate the biological activity of the compound. Such is illustrated by certain modified compounds, discussed in the examples below, that do not possess the biological activity associated with the corresponding unmodified compounds.

With the present technology even higher molecular weight compounds on the molecular-weight continuum of small molecule compounds, as defined under section (E) below, can be loaded effectively into intact, bacterially derived vesicles. Thus, the modified compound can have a molecular weight of at least about 1000 Daltons, or alternatively at least about 1100, 1200, 1300, 1400, or 1500 Daltons.

In the context of any of the methods and compositions described above, the compound or the modified compound can be hydrophobic, while in another aspect, hydrophilic. In yet another aspect the compound or the modified compound is water-soluble.

Along a similar line, the invention provides in one aspect a composition comprising intact, bacterially derived vesicles, in the form of minicells and/or killed bacterial cells, and a compound of the formula D-L-F or a salt thereof, where D is the residue of a non-fluorescent small molecule compound such as a drug, L is a linker, and F is a fluorescent moiety. The composition is useful particularly for the fact that loading the compound into the vesicles is facilitated over the instance of the unmodified small molecular compound.

In accordance with one aspect, the bacterial vesicle of this description is an intact, bacterially derived minicell. Given the high efficiency of the inventive loading methodology, each such vesicle (i.e., minicell) can be packaged with at least about 100,000 copies of the compound. More particularly, each minicell can be packaged with at least about 200,000 copies or, alternatively, with at least about 300,000, about 400,000, about 500,000, about 600,000, about 700,000, about 800,000, about 900,000 or about 1 million copies of the compound.

In one aspect the minicells enclose at least about 200 ng, or at least 300 ng, 400 ng, 500 ng, 600 ng, 700 ng, 800 ng, 900 ng, or 1,000 ng of a given fluorescent compound or combination of fluorescent compounds per $10^9$ minicells. By contrast, the amount loaded per $10^9$ minicells of a comparable non-fluorescent compound typically is an order of magnitude smaller, i.e., on the order of tens of nanograms.

According to another aspect of the disclosure, the intact, nonliving vesicle is a killed bacterial cell. In keeping with the description above, a given killed bacterial cell has a capacity that is about 3-4 times greater than that of a minicell. Accordingly, the killed bacterial cell can be packaged at least about 400,000 copies of the modified compound. More particularly, each killed bacterial cell can be packaged with at least about 800,000 copies or, alternatively, with at least about 1,200,000, about 1,600,000, about 2,000,000, about 2,400,000, about 2,800,000, about 3,200,000, about 3,600,000 or about 4 million copies of the compound.

Such killed bacterial cells can enclose at least about 800 ng, or at least 1,200 ng, 1,600 ng, 2,000 ng, 2,400 ng, 2,800 ng, 3,200 ng, 3,600 ng, or 4,000 ng of the compound per $10^9$ killed cells.

(D) Intact, Bacterially Derived Vesicles

The phrases "intact, bacterially derived vesicle" and "intact, nonliving bacterial vesicle" synonymously refer to a vesicular derivative of a bacterial cell, including a killed bacterial cell and a bacterial minicell, which cannot reproduce and which is unable actively to initiate an entry into a mammalian cell. In this context "intact" connotes regular continuity and structural integrity in the cell envelope, i.e., in the plasma membrane and the surrounding cell wall, which includes multiple layers (for vesicles derived from Gram-positive bacterial cells) or a bilayer outer membrane around a single-layer cell wall (for vesicles derived from Gram-negative bacterial cells). See BERGEY'S MANUAL OF SYSTEMATIC BIOLOGY, 2nd ed. (Springer, 2012).

Thus, the phrase "intact killed bacterial cells" denotes intact, non-living prokaryotic cells of bacteria, cyanobacteria, eubacteria or archaebacteria, possessing an intact cell envelope and containing genetic material (nucleic acid) that is endogenous to the bacterial species. Id. For pharmaceutical use, a composition of killed bacterial cells are isolated as thoroughly as possible from immunogenic components and other toxic contaminants. Methodology for purifying intact killed bacterial cells is described in U.S. Pat. No. 8,591,862, the relevant contents of which are incorporated by reference here. Briefly, live bacterial cells can be killed by antibiotics, followed by removal of cell debris and free endotoxins.

"Minicell" refers to a derivative of a bacterial cell that is lacking in chromosomes ("chromosome-free") and that is engendered by a disturbance in the coordination, during binary fission, of cell division with DNA segregation. Minicells are distinct from other small vesicles, such as so-called "membrane blebs" (~0.2 µm or less in size), which are generated and released spontaneously in certain situations but which are not due to specific genetic rearrangements or episomal gene expression. By the same token, intact minicells are distinct from bacterial ghosts, which are not generated due to specific genetic rearrangements or episomal gene expression.

Bacterially derived minicells employed in this disclosure are fully intact, as discussed above, and thus are distinguished from other chromosome-free forms of bacterial cellular derivatives characterized by an outer or defining membrane that is disrupted or degraded, even removed. See U.S. Pat. No. 7,183,105 at column 111, lines 54 et seq. The intact membrane that characterizes the minicells of the present disclosure allows retention of the therapeutic payload within the minicell until the payload is released, post-uptake, within a tumor cell.

The minicell employed in accordance with this disclosure can be prepared from bacterial cells, such as *E. coli* and *S. typhymurium*. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and a chromosome-less minicell. See de Boer et al., *J. Bacteriol.* 174: 63-70 (1992); Raskin and de Boer, *J. Bacteriol.* 181: 6419-24 (1999); Hu and Lutkenhaus, *Mol. Microbiol.* 34: 82-90 (1999); and Harry, *Mol. Microbiol.* 40: 795-803 (2001).

In addition to min operon mutations, chromosome-less minicells are generated following a range of other genetic rearrangements or mutations that affect septum formation, for example, in the divIVB1 in *B. subtilis*. See Reeve and Cornett, *J. Virol.* 15: 1308-16 (1975). Minicells also can be formed following a perturbation in the levels of gene expression of proteins involved in cell division/chromosome segregation. For instance, over-expression of minE leads to polar division and production of minicells. Similarly, chromosome-less minicells can result from defects in chromosome segregation, e.g., the smc mutation in *Bacillus subtilis*

(Britton et al., *Genes Dev.* 12: 1254-59 (1998)), the spoOJ deletion in *B. subtilis* (Ireton et al., *J. Bacteriol.* 176: 5320-29 (1994)), the mukB mutation in *E. coli* (Hiraga et al., *J. Bacteriol.* 171: 1496-1505 (1989)), and the parC mutation in *E. coli* (Stewart and D'Ari, *J. Bacteriol.* 174: 4513-51 (1992)). Further, CafA can enhance the rate of cell division and/or inhibit chromosome partitioning after replication (Okada et al., *J. Bacteriol.* 176: 917-22 (1994)), resulting in formation of chained cells and chromosome-less minicells.

Min systems exist in most bacterial species, see Barak, *Frontiers in Microbiology* 4: Art. 378 (2013), while in other bacteria, such as *Caulobacter crescentus*, another mechanism has evolved for controlling placement of the division septum, which mechanism can be manipulated to produce minicells via unequal division. Accordingly, minicells can be prepared for the present disclosure from any bacterial cell, be it of Gram-positive or Gram-negative origin. Furthermore, the minicells used in the disclosure should possess intact cell walls (i.e., are "intact minicells"), as noted above, and should be distinguished over and separated from other small vesicles, such as membrane blebs, which are not attributable to specific genetic rearrangements or episomal gene expression.

In a given embodiment the parental (source) bacteria for the minicells can be Gram-positive or they can be Gram-negative, as mentioned. Parental bacteria thus can be selected, for example, from any one or more of the taxons Terrabacteria (BV1), which includes the Gram-positive phyla (Actinobacteria and Firmicutes), among others; Proteobacteria (BV2), a phylum of which all members are Gram-negative; and category BV4, which includes Spirochaetes, Sphingobacteria, and Planctobacteria as well as other Gram-negative bacteria, such as Acidobacteria.

Pursuant to one aspect, therefore, the bacteria from which killed bacterial cells or minicells are prepared are selected from one or more of the taxons Firmicutes (BV3), such as Bacilli, Clostridia and Tenericutes/Mollicutes, and Actinobacteria (BV5), such as Actinomycetales and Bifidobacteriales. In yet a further aspect, the parental bacteria are selected from any one or more of Eobacteria (Chlorofexi, Deinococcus-Thermus), Cyanobacteria, Thermodesulfobacteria, thermophiles (Aquificae, Thermotogae), Alpha, Beta, Gamma (Enterobacteriaceae), Delta or Epsilon Proteobacteria, Spirochaetes, Fibrobacteres, Chlorobi/Bacteroidetes, Chlamydiae/errcomicrobia, Planctomycetes, Acidobacteria, Chrysiogenetes, Deferribacteres, Fusobacteria, Gemmatimonadetes, Nitrospirae, Synergistetes, Dictyoglomi, Lentisphaerae Bacillales, Bacillaceae, Listeriaceae, Staphylococcaceae, Lactobacillales, Enterococcaceae, Lactobacillaceae, Leuconostocaceae, Streptococcaceae, Clostridiales, Halanaerobiales, Thermoanaerobacterales, Mycoplasmatales, Entomoplasmatales, Anaeroplasmatales, Acholeplasmatales, Haloplasmatales, Actinomycinese, Actinomycetaceae, Corynebacterinese, Nocardiaceae, Corynebacteriaceae, Frankineae, Frankiaceae, Micrococcineae, Brevibacteriaceae, and Bifidobacteriaceae.

For pharmaceutical use a composition of the present disclosure should comprise killed bacterial cells or minicells that are isolated as thoroughly as possible from immunogenic components and other toxic contaminants. Methodology for purifying bacterially derived minicells to remove free endotoxin and parent bacterial cells are described in WO2004/113507, which is incorporated by reference here in its entirety. Briefly, the purification process achieves removal of (a) smaller vesicles, such as membrane blebs, which are generally smaller than 0.2 μm in size, (b) free endotoxins released from cell membranes, and (c) parental bacteria, whether live or dead, and their debris, which are sources of free endotoxins, too. Such removal can be implemented with, inter alia, a 0.2 μm filter to remove smaller vesicles and cell debris, a 0.45 μm filter to remove parental cells following induction of the parental cells to form filaments, antibiotics to kill live bacterial cells, and antibodies against free endotoxins.

Underlying the purification procedure is a discovery by the present inventors that, despite the difference of their bacterial sources, all intact minicells are approximately 400 nm in size, i.e., larger than membrane blebs and other smaller vesicles and yet smaller than parental bacteria. Size determination for minicells can be accomplished by using solid-state, such as electron microscopy, or by liquid-based techniques, e.g., dynamic light scattering. The size value yielded by each such technique can have an error range, and the values can differ somewhat between techniques. Thus, the size of minicells in a dried state can be measured via electron microscopy as approximately 400 nm±50 nm. On the other hand, dynamic light scattering can measure the same minicells to be approximately 500 nm±50 nm in size. Also, drug-packaged, ligand-targeted minicells can be measured, again using dynamic light scattering, to be approximately 600 nm±50 nm.

This scatter of size values is readily accommodated in practice, e.g., for purposes of isolating minicells from immunogenic components and other toxic contaminants, as described above. That is, an intact, bacterially derived minicell is characterized by cytoplasm surrounded by a rigid membrane, which gives the minicell a rigid, spherical structure. This structure is evident in transmission-electron micrographs, in which minicell diameter is measured, across the minicell, between the outer limits of the rigid membrane. This measurement provides the above-mentioned size value of 400 nm±50 nm.

Another structural element of a minicell derived from Gram-negative bacteria is the O-polysaccharide component of lipopolysaccharide (LPS), which is embedded in the outer membrane via the lipid A anchor. The component is a chain of repeat carbohydrate-residue units, with as many as 70 to 100 repeat units of four to five sugars per chain. Because these chains are not rigid, in a liquid environment, as in vivo, they can adopt a waving, flexible structure that gives the general appearance of seaweed in a coral sea environment; i.e., the chains move with the liquid while remaining anchored to the minicell membrane.

Influenced by the O-polysaccharide component, dynamic light scattering can provide a value for minicell size of about 500 nm to about 600 nm, as noted above. Nevertheless, minicells from Gram-negative and Gram-positive bacteria alike readily pass through a 0.45 μm filter, which substantiates an effective minicell size of 400 nm±50 nm. The above-mentioned scatter in sizes is encompassed by the present invention and, in particular, is denoted by the qualifier "approximately" in the phrase "approximately 400 nm in size" and the like.

In relation to toxic contaminants, a composition of the disclosure can contain less than about 350 EU free endotoxin. Illustrative in this regard are levels of free endotoxin of about 250 EU, about 200 EU, about 150 EU, about 100 EU, about 90 EU, about 80 EU, about 70 EU, about 60 EU, about 50 EU, about 40 EU, about 30 EU, about 20 EU, about 15 EU, about 10 EU, about 9 EU, about 8 EU, about 7 EU, about 6 EU, about 5 EU, about 4 EU, about 3 EU, about 2 EU, about 1 EU, about 0.9 EU, about 0.8 EU, about 0.7 EU, about 0.6 EU, about 0.5 EU, about 0.4 EU, about 0.3 EU, about 0.2 EU, about 0.1 EU, about 0.05 EU, and about 0.01 EU, respectively.

A composition of the disclosure also can contain at least about $10^8$ vesicles, e.g., at least about 5×10. Alternatively, the composition can contain on the order of $10^9$ or $10^{10}$ vesicles, e.g., $5 \times 10^9$, $1 \times 10^{10}$ or $5 \times 10^{10}$ vesicles. Amongst any such number of minicells, moreover, a composition of the disclosure can contain fewer than about 10 contaminating live/parent bacterial cells, e.g., fewer than about 9, 8, 7, 6, 5, 4, 3, 2, or 1 live/parent bacterial cells.

(E) Small Molecule Compounds

As noted, this disclosure provides methodology for loading into an intact, nonliving bacterial vesicle a small molecule compound that is fluorescent. The small molecule compound can be intrinsically fluorescent (autofluorescent) or it can be extrinsically fluorescent, i.e., fluorescent by virtue of the addition of a fluorescent moiety to a non-fluorescent compound, whereupon the modified compound is loaded into an intact, nonliving bacterial vesicle.

In accordance with this disclosure, the small molecule compound can be a "small molecule drug," which means that it is biologically active at the point of administration of the inventive composition or that it converts to a biologically active form (is "activated") in vivo, post-administration. In keeping with the definition above, "biologically active" refers to the ability of a small molecule drug to react with protein, nucleic acid or other molecules in a cell, leading to a functional change in the cell. In one aspect the change is therapeutically desirable. The biological activity can be a cytotoxicity, for example, whereby the small molecule compound is a chemotherapeutic agent, i.e., it is a small molecule "chemotherapeutic drug." Thus, "chemotherapeutic drug," "chemotherapeutic agent," and "chemotherapy" are employed interchangeably to connote a small molecule drug that has the ability to kill or disrupt a neoplastic cell.

The "small molecule drug" subcategory encompasses compounds characterized by having (i) an effect on a biological process and (ii) a relatively low molecular weight as compared to a protein or polymeric macromolecule. Small molecule drugs typically are about 900 Daltons or less, with a lower limit of about 150 Daltons, as illustrated by Temodar® (temozolomide), at about 194 Daltons, which is used to treat gliaoblastoma multiforme and other types of brain cancer. However, while most molecules will be less than about 900 daltons in size, attaching a fluorescent molecule or altering the drug's structure to enhance loading of the drug into minicells may increase its molecular weight up to about 1500 daltons. In this context "about" indicates that the qualified molecular-weight value is subject to variances in measurement precision and to experimental error on the order of several Daltons or tens of Daltons. Thus, a small molecule drug (unmodified, modified, or attached to a fluorescent molecule) can have a molecular weight of about 1500 Daltons or less, about 1400 Daltons or less, about 1300 Daltons or less, about 1200 Daltons or less, about 1100 Daltons or less, about 1000 Daltons or less, about 900 Daltons or less, about 800 Daltons or less, about 700 Daltons or less, about 600 Daltons or less, about 500 Daltons or less, or about 400 Daltons or less, e.g., in the range of about 150 to about 400 Daltons. More specifically, a small molecule drug (unmodified, modified, or attached to a fluorescent molecule) can have a molecular weight of about 400 Daltons or more, about 450 Daltons or more, about 500 Daltons or more, about 550 Daltons or more, about 600 Daltons or more, about 650 Daltons or more, about 700 Daltons or more, about 750 Daltons or more, about 800 Daltons or more, about 850 Daltons or more, about 900 Daltons or more, about 950 Daltons or more, about 1000 Daltons or more, about 1050 Daltons or more, about 1100 Daltons or more, about 1150 Daltons or more, about 1200 Daltons or more, about 1250 Daltons or more, about 1300 Daltons or more, about 1350 Daltons or more, about 1400 Daltons or more, about 1450 Daltons or more, or about 1500 Daltons or more. In another embodiment, the small molecule drug (unmodified, modified, or attached to a fluorescent molecule) packaged into the minicells has a molecular weight between about 400 and about 1300 Daltons, between about 400 and about 1100 Daltons, between about 400 and about 1000 Daltons, between about 450 and about 900 Daltons, between about 450 and about 850 Daltons, between about 450 and about 800 Daltons, between about 500 and about 800 Daltons, or between about 550 and about 750 Daltons.

Subject to the qualifications set out above to the present invention's methodological and compositional aspects, respectively, suitable small molecule chemotherapeutic drugs include but are not limited to nitrogen mustards, nitrosoureas, ethyleneimine, alkane sulfonates, tetrazine, platinum compounds, pyrimidine analogs, purine analogs, anti-metabolites, folate analogs, anthracyclines, taxanes, vinca alkaloids, and topoisomerase inhibitors, inter alia. Accordingly, a small molecule chemotherapeutic drug for use in the present invention can be selected from among any of the following, inter alia: enediynes, such as dynemicin A, unicalamycin, calicheamicin γ1 and calicheamicin θ1; meayamicin, a synthetic analog of FR901464; benzosuberene derivatives as described, for example, by Tanpure et al., *Bioorg. Med. Chem.* 21: 8019-32 (2013); auristatins, such as auristatin E, mono-methyl auristatin E (MMAE), and auristatin F, which are synthetic analogs of dolastatin; duocarmysins such as duocarmycin SA and CC-1065; maytansine and its derivatives (maytansinoids), such as DM1 and DM4; irinotecan (Camptosar®) and other topoisomerase inhibitors, such as topotecan, etoposide, mitoxantrone and teniposide; and yatakemycin, the synthesis of which is detailed by Okano et al., *J. Am. Chem. Soc.* 128: 7136-37 (2006).

More particularly, any one or more or all of the specific small molecule chemotherapeutic drugs detailed in this paragraph are illustrative of those suitable for use in accordance with the qualifications set out in section (C) above: actinomycin-D, alkeran, ara-C, anastrozole, BiCNU, bicalutamide, bleomycin, busulfan, capecitabine (Xeloda®), carboplatin, carboplatinum, carmustine, CCNU, chlorambucil, cisplatin, cladribine, CPT-11, cyclophosphamide, cytarabine, cytosine arabinoside, cytoxan, dacarbazine, dactinomycin, dexrazoxane, docetaxel, DTIC, ethyleneimine, etoposide, floxuridine, fludarabine, fluorouracil, flutamide, fotemustine, gemcitabine, hexamethylamine, hydroxyurea, idarubicin, ifosfamide, lomustine, mechlorethamine, melphalan, mercaptopurine, methotrexate, mitomycin, mitotane, oxaliplatin, paclitaxel, pamidronate, pentostatin, plicamycin, procarbazine, streptozocin, STI-571, tamoxifen, temozolomide, teniposide, tetrazine, thioguanine, thiotepa, tomudex, topotecan, treosulphan, trimetrexate, vinblastine, vincristine, vindesine, vinorelbine, and VP-16. Pursuant to the invention, any one or more or all of these small molecule chemotherapeutic drugs can be derivatized with a fluorophore or, as the case may be, can be exploited for intrinsic fluorescence.

As detailed in section (C) above, compositions within the invention are subject to exclusions in relation to intrinsically fluorescent drugs (subcategory (A)) and to extrinsically florescent active agents (subcategory (B)), respectively. For subcategory (A), the exclusions consist of doxorubicin, irinotecan, bisantrene, epirubicin, topotecan, epirubicin, daunorubicin, and mitoxantrone. For subcategory (B), the exclusions consist of Oregon Green® 488-conjugated paclitaxel and BODIPY® FL-conjugated vinblastine.

In some embodiments, D in the formula D-L-F is of formula D-I or D-II

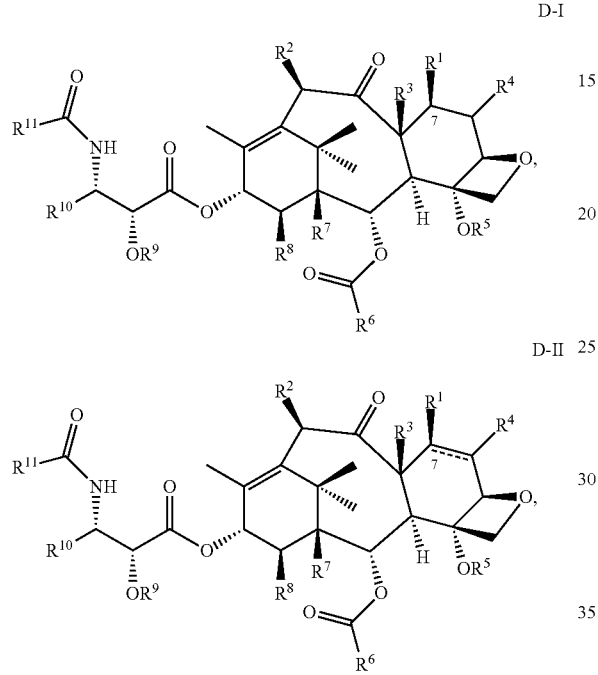

or a stereoisomer thereof or a pharmaceutically acceptable salt of the compound or the stereoisomer,
where:
- $R^1$ is H, —OH, $C_{1-4}$ alkoxy, —O—C(O)—($C_{1-4}$ alkyl), substituted $C_{1-4}$ alkoxy, —O—C(O)—(substituted $C_{1-4}$ alkyl), —O—$CH_2$—O—P(O)(OH)$_2$, —O—$CH_2$—O—($C_{1-4}$ alkyl), —O—$CH_2$—S—($C_{1-4}$ alkyl), or, taken together with $R^3$ form —$CH_2$—, or, taken together with $R^4$, a double bond, $OR^e$, or $R^e$;
- $R^2$ is H, —OH, $C_{1-4}$ alkyl, substituted $C_{1-4}$ alkyl, $C_{1-4}$ alkoxy, substituted $C_{1-4}$ alkoxy, —O—C(O)—($C_{1-4}$ alkyl), —O—C(O)-(substituted $C_{1-4}$ alkyl), —O—$CH_2$—O—($C_{1-4}$ alkyl), —S—$CH_2$—O—($C_{1-4}$ alkyl), —O—C(O)—$R^e$ or —$R^e$;
- $R^3$ is H, $C_{1-4}$ alkyl, or, taken together with $R^1$ form —$CH_2$—;
- $R^4$ is H or halogen, or, taken together with $R^1$, a double bond;
- $R^5$ is H, $C_{1-4}$ acyl, $C_{1-4}$ alkyl, substituted $C_{1-4}$ alkyl, $C_{1-4}$ alkoxymethyl, ($C_{1-4}$ alkyl)thiomethyl, —C(O)—($C_{1-4}$ alkyl), —C(O)-(substituted $C_{1-4}$ alkyl), —C(O)—O—($C_{1-4}$ alkyl), —C(O)—O(substituted $C_{1-4}$ alkyl), —C(O)—NH($C_{1-4}$ alkyl), —C(O)—NH(substituted $C_{1-4}$ alkyl), or $R^e$;
- $R^6$ is phenyl or substituted phenyl;
- $R^7$ is H, —OH, —CO—($C_{1-4}$ alkyl), —CO-(substituted $C_{1-4}$ alkyl), $C_{1-4}$ alkyl, substituted $C_{1-4}$ alkyl, ($C_{1-4}$ alkoxy)methyl or ($C_{1-4}$ alkyl)thiomethyl, or, taken together with $R^8$ and the carbon atoms to which $R^7$ and $R^8$ are bonded, a five or six membered a non-aromatic heterocyclic ring;
- $R^8$ is H, —$CH_3$, or, taken together with $R^7$ and the carbon atoms to which $R^7$ and $R^8$ are bonded, a five or six membered a non-aromatic heterocyclic ring;
- $R^9$ is H, $C_{1-4}$ alkyl, substituted $C_{1-4}$ alkyl, —CO—($C_{1-4}$ alkyl), —CO-(substituted $C_{1-4}$ alkyl), or $R^e$;
- $R^{10}$ is $C_{1-4}$ alkyl, substituted $C_{1-4}$ alkyl, aryl or substituted aryl;
- $R^{11}$ is $C_{1-4}$ alkyl, substituted $C_{1-4}$ alkyl, phenyl, substituted phenyl, —$SR^{12}$, —$NHR^{12}$ or —$OR^{12}$; and
- $R^{12}$ is $C_{1-4}$ alkyl, substituted $C_{1-4}$ alkyl, phenyl, or substituted phenyl;
provided at least one of $R^1$, $R^2$, $R^5$ and $R^9$ is $R^e$, and $R^e$ is a point of connection to L.

In some embodiments:
- $R^1$ is H, OH, —$CH_2SCH_3$, —$CH_2$—O—P(O)(OH)$_2$, $OR^e$ or $R^e$;
- $R^2$ is H, —OH, —OCO—$CH_3$, —CO—$CH_3$ or —($CH_2$)$_2$—N-morpholino;
- $R^3$ is methyl, or, $R^3$ and $R^4$, taken together, are alkylene, such as —$CH_2$—;
- $R^4$ is H or —F;
- $R^5$ is —CO—$CH_3$;
- $R^6$ is phenyl;
- $R^7$ H or OH,
- $R^8$ is H;
- or $R^7$ and $R^8$, taken together, are —O—CO—O—;
- $R^9$ is H, —C(O)—CHBr—($CH_2$)$_{13}$—$CH_3$, —C(O)—($CH_2$)$_2$—$NH_2$; —C(O)—($CH_2$)$_{14}$—$CH_3$; —C(O)—$CH_2$—CH(OH)—COOH, —C(O)—$CH_2$—O—C(O)$CH_2CH(NH_2)$—$CONH_2$, —C(O)—$CH_2$—O—$CH_2CH_2OCH_3$, —C(O)—O—C(O)—$CH_2CH_3$, or —$R^e$;
- $R^{10}$ is phenyl, ($CH_3$)$_2CHCH_2$—, -2-furanyl, cyclopropyl or para-toluyl; and
- $R^{11}$ is phenyl, tert-butoxy, —S—$CH_2$—CH—($CH_3$)$_2$, —S—CH($CH_3$)$_3$, —S—($CH_2$)$_3CH_3$, —O—CH($CH_3$)$_3$, —NH—CH($CH_3$)$_3$, —CH=C($CH_3$)$_2$ or para-chlorophenyl;
provided that at least one of $R^1$ and $R^9$ is $R^e$.

In some embodiments, D in the formula D-L-F is of formula

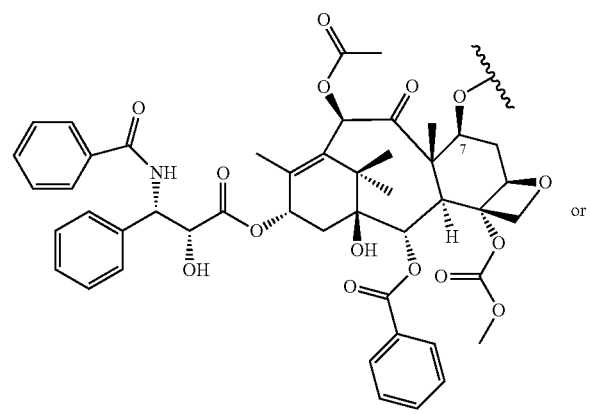

or

-continued
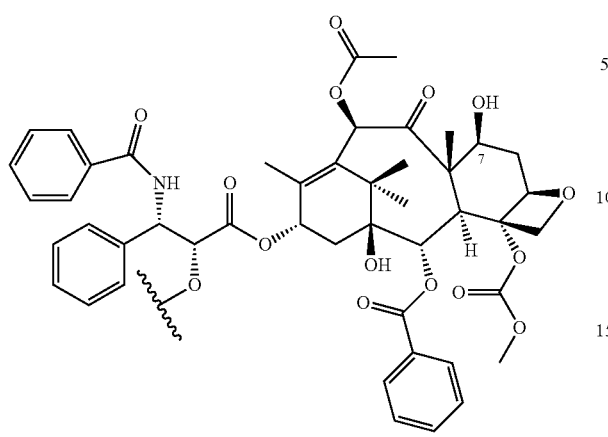
or a stereoisomer thereof, or a pharmaceutically acceptable salt of the compound or the stereoisomer,
where  represents the point of connection with L.
In some embodiments, D in the formula D-L-F is a residue of a compound selected from:
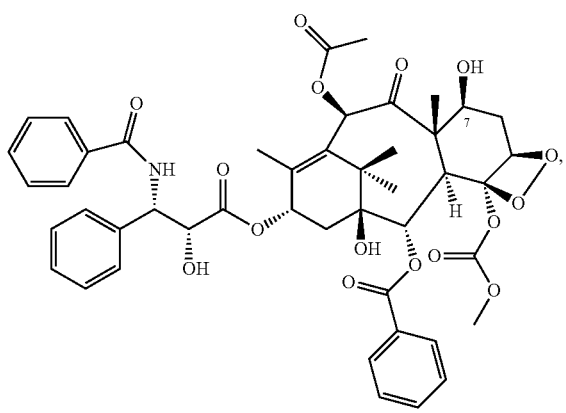
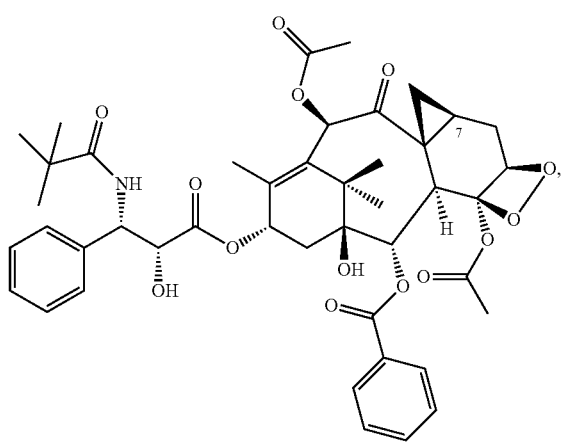
-continued
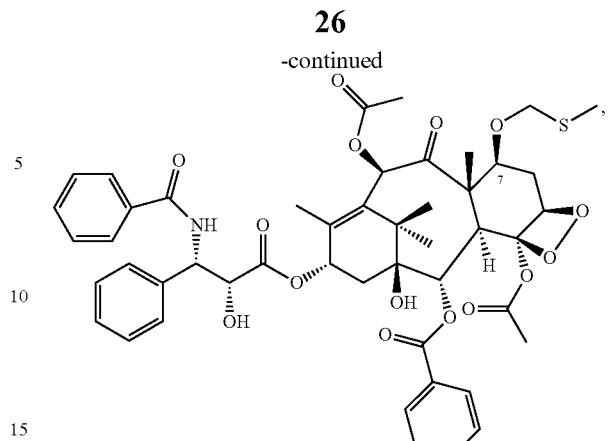
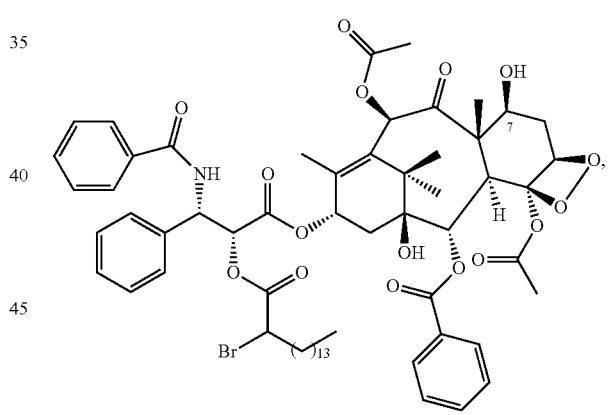
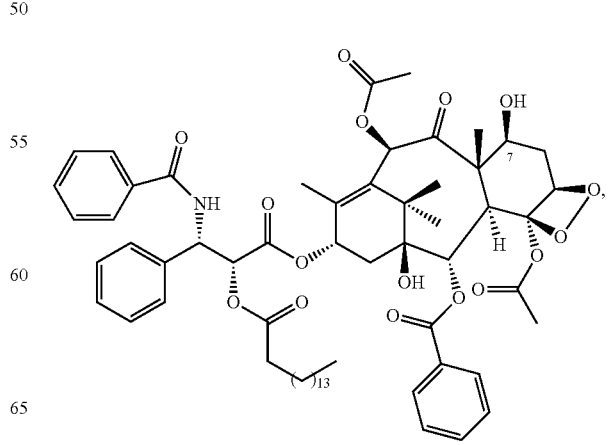

27
-continued
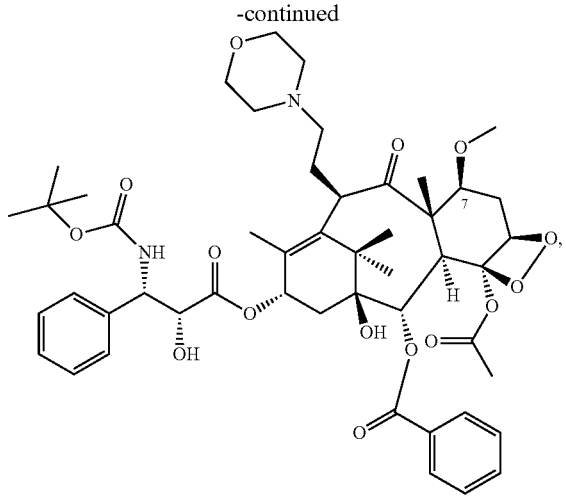
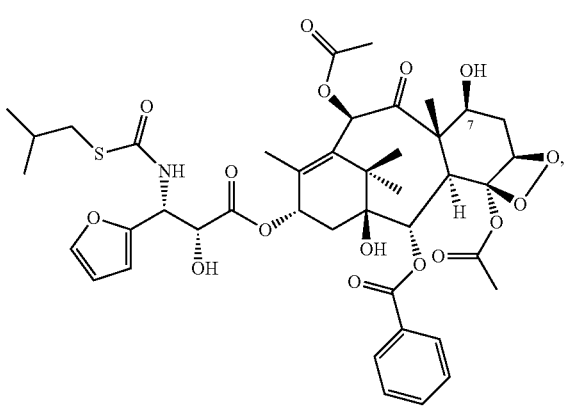
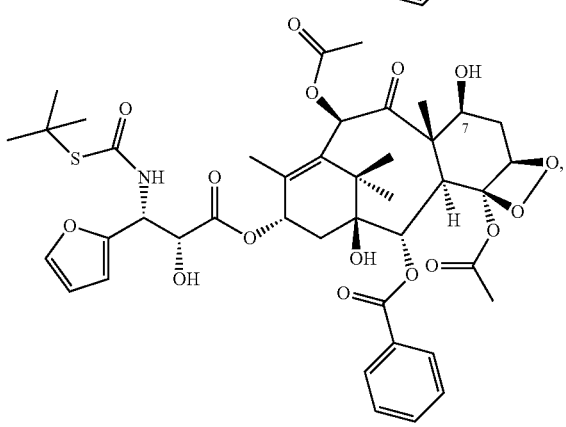
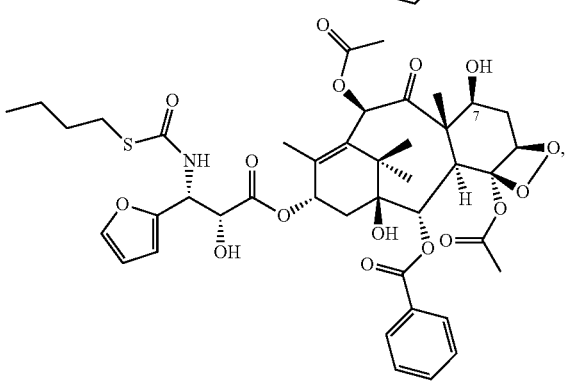
28
-continued
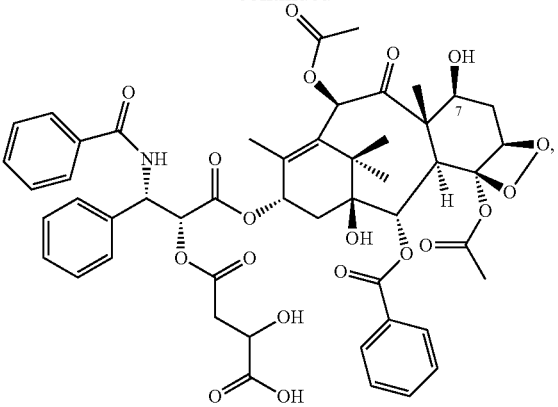
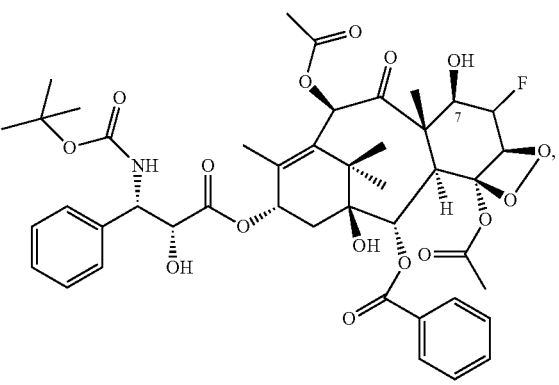
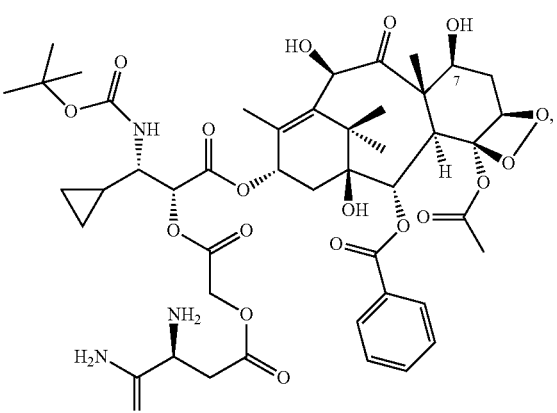
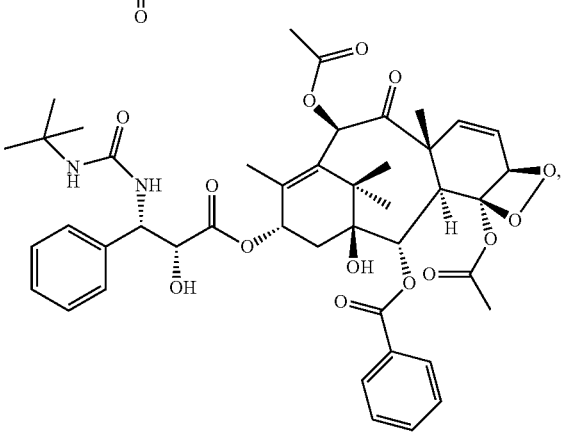

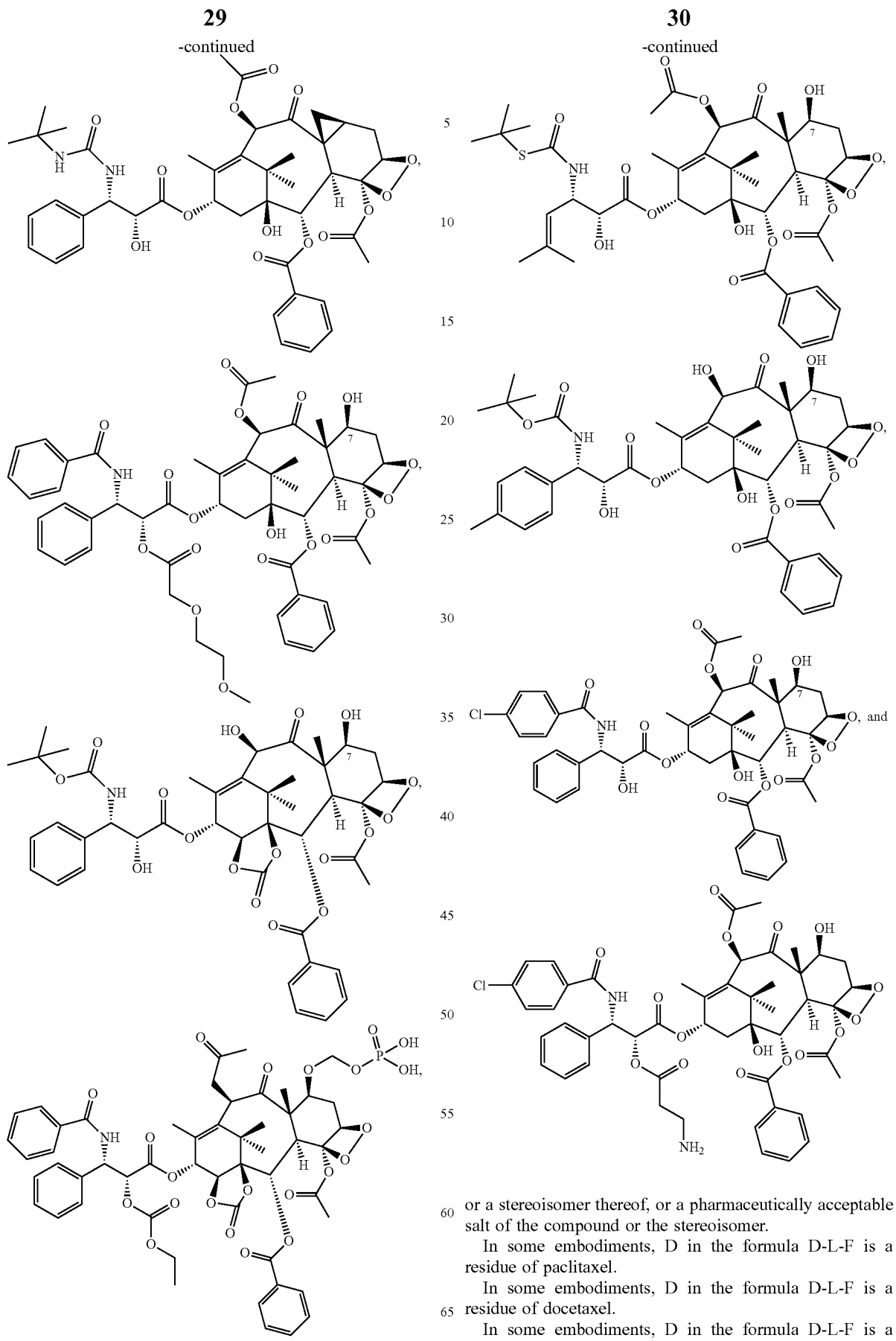
or a stereoisomer thereof, or a pharmaceutically acceptable salt of the compound or the stereoisomer.
In some embodiments, D in the formula D-L-F is a residue of paclitaxel.
In some embodiments, D in the formula D-L-F is a residue of docetaxel.
In some embodiments, D in the formula D-L-F is a residue of vinblastine or an analog thereof.

(F) Fluorescent Moieties

Fluorescent moieties are well known in the art. In some aspects, the fluorescent moiety has a maximum wavelength of excitation of 760 nm, and/or a maximum wavelength of emission of 770 nm. In some aspects, the fluorescent moiety has a maximum wavelength of excitation of 600 nm, and/or a maximum wavelength of emission of 600 nm. In some aspects, the fluorescent moiety has a maximum wavelength of excitation of 500 nm, and/or a maximum wavelength of emission of 550 nm. In some embodiments the fluorescent moiety has an excitation wavelength selected from 380-450 nm, 450-495 nm, 495-570 nm, 570-590 nm, 590-620 nm, 620-650 nm, 650-700 nm or 700-760 nm. In some embodiments the fluorescent moiety has an emission wavelength selected from 380-450 nm, 450-495 nm, 495-570 nm, 570-590 nm, 590-620 nm 620-650 nm, 650-700 nm or 700-770 nm.

In some aspects the fluorescent moiety has a molecular weight of about 100 Daltons to about 1000 Daltons, or any amount inbetween these two values, or about 100 Daltons to about 650 Daltons, or any amount inbetween these two values. In other embodiments, the fluorescent moiety has a molecular weight of about 200, about 300, about 400, about 500, about 600, about 700, about 800, about 900 Daltons, or any amount inbetween these values. In yet other embodiments, the fluorescent moiety has a molecular weight of about 150, about 200, about 250, about 300, about 350, about 400, about 450, about 500, about 550, about 600, about 650 Daltons, or any amount inbetween these values.

In one aspect the fluorescent moiety (F) is a residue of a compound selected from a xanthene derivative, such as fluorescein, rhodamine, Oregon Green, eosin, and Texas Red; a cyanine derivative such as cyanine, indocarbocyanine, oxacarbocyanine, thiacarbocyanine, and merocyanine; a naphthalene derivative such as dansyl and prodan derivatives; a coumarin derivative; a oxadiazole derivative such as pyridyloxazole, nitrobenzoxadiazole and benzoxadiazole; a anthracene derivatives such as anthraquinones, e.g., DRAQ5, DRAQ7 and CyTRAK Orange; a pyrene derivative such as cascade blue; a oxazine derivative such as Nile Red, Nile Blue, cresyl violet, and oxazine 170; a acridine derivative such as proflavin, acridine orange, and acridine yellow; a arylmethine derivative such as auramine, crystal violet, and malachite green; and a tetrapyrrole derivative such as porphin, phthalocyanine, and bilirubin.

In one aspect the fluorescent moiety (F) is

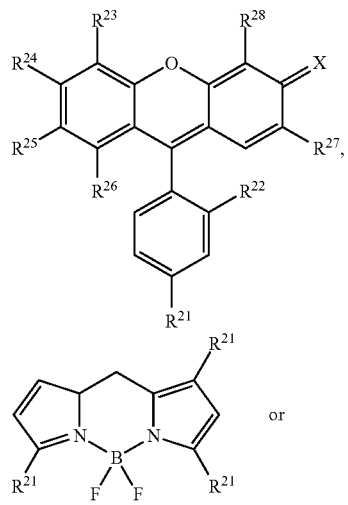

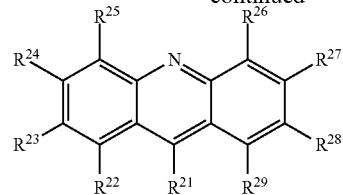

where
X is O or $NR^{20}$;
$R^{20}$ is H or $C_{1-4}$ alkyl;
$R^{21}$ is H, $C_{1-4}$ alkyl, halo, —OH, —COOH, —O—C(O)—($C_{1-4}$ alkyl), —C(O)—O—($C_{1-4}$ alkyl), $C_{1-4}$ alkoxy, halo, —$NO_2$, —$SO_2C$, —$SO_3^-$, or $R^f$;
$R^{22}$ is H, halo, —OH, —COOH, $C_{1-4}$ alkyl, substituted $C_{1-4}$ alkyl, $C_{1-4}$ alkoxy, substituted $C_{1-4}$ alkoxy, —O—C(O)—($C_{1-4}$ alkyl), —O—C(O)-(substituted $C_{1-4}$ alkyl), —C(O)—O—($C_{1-4}$ alkyl), —C(O)—O-(substituted $C_{1-4}$ alkyl), —O—$CH_2$—O—($C_{1-4}$ alkyl), —S—$CH_2$—O—($C_{1-4}$ alkyl), —$NO_2$, —$SO_2Cl$, —$SO_3^-$, or $R^f$;
each $R^{23}$, $R^{24}$, $R^{25}$, $R^{26}$, $R^{27}$, $R^{28}$ and $R^{29}$ are independently H, halo, —OH, —$NO_2$, —$CH_3$ or $R^f$,
or $R^{23}$ and $R^{24}$ join together to form a 5-, 6- or 7-membered ring, and/or $R^{24}$ and $R^{25}$ join together to form a 5-, 6- or 7-membered ring, and/or $R^{27}$ and X join together to form a 5-, 6- or 7-membered ring, and/or $R^{28}$ and X join together to form a 5-, 6- or 7-membered ring;
provided at least one and no more than two of $R^{21}$, $R^{22}$, $R^{23}$, $R^{24}$, $R^{25}$, $R^{26}$, $R^{27}$, $R^{28}$ and $R^{29}$ is $R^f$; wherein $R^f$ is a point of connection to L.

In one aspect the fluorescent moiety (F) is

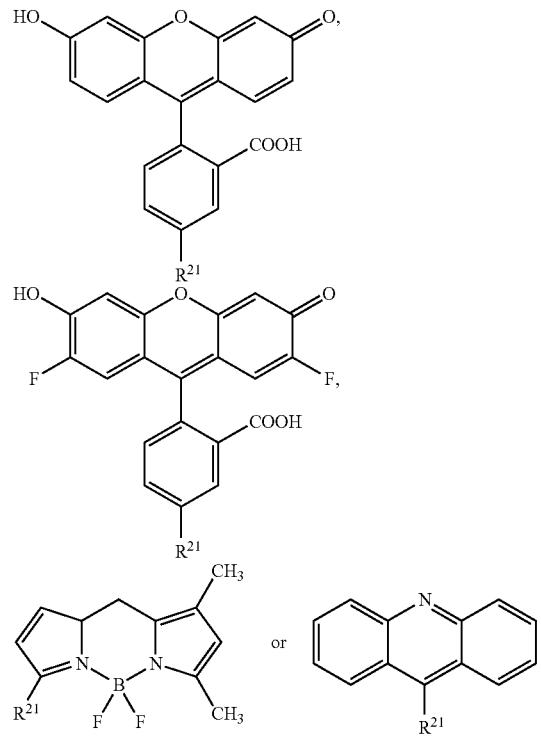

where $R^{21}$ is the point of connection to L.

In one aspect the fluorescent moiety (F) is a residue of a compound selected from:

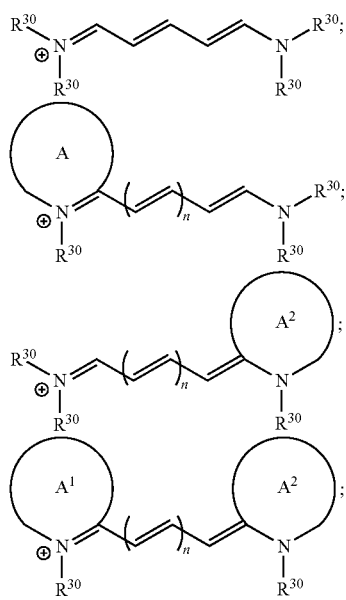

where each $R^{30}$ is independently hydrogen, $C_{1-4}$ alkyl or substituted $C_{1-4}$ alkyl, $A^1$ and $A^2$ are independently optionally substituted nitrogen containing heteroaryl, n is an integer selected from 1-10. In some embodiments, the heteroaryl is pyrrole, imidazole, thiazole, pyridine, quinoline, indole, benzoxazole or benzothiazole.

In one aspect the fluorescent moiety (F) is

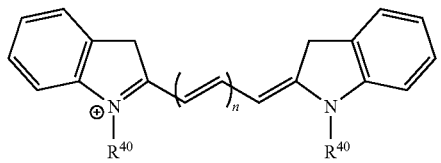

where one of $R^{40}$ is $R^{30}$ and the other is $R^f$, $L^{40}$-$R^f$, $L^{40}$-$OR^f$, $L^{40}$-$NHR^f$, $L^{40}$ is $(CH_2)_m$, wherein one or two $CH_2$ groups are optionally replaced with O, S, SO, $SO_2$, C(O)O, OC(O), C(O)NH, NHC(O), NH or optionally substituted phenyl, and $R^f$ is a point of connection to L.

In one aspect the fluorescent moiety (F) is

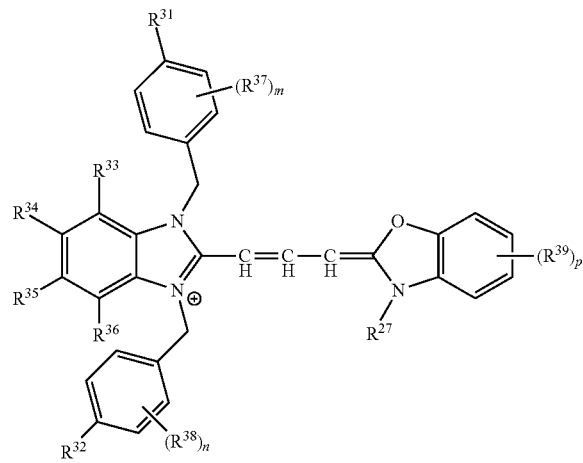

where
- $R^{31}$ and $R^{32}$ are independently H, —OH, $C_{1-4}$ alkyl, $C_{1-4}$ haloalkyl, —O—C(O)—($C_{1-4}$ alkyl), —C(O)—O—($C_{1-4}$ alkyl), $C_{1-4}$ alkoxy, halo, or $R^f$;
- $R^{34}$ and $R^{35}$ are independently H, halo, —OH, —COOH, $C_{1-4}$ alkyl, substituted $C_{1-4}$ alkyl, $C_{1-4}$ alkoxy, —O—C(O)—($C_{1-4}$ alkyl), —C(O)—O—($C_{1-4}$ alkyl), —O—$CH_2$—O—($C_{1-4}$ alkyl), —S—$CH_2$—O—($C_{1-4}$ alkyl), or $R^f$;
- each $R^{33}$ and $R^{36}$ is independently H, halo, —OH, —$CH_3$ or $R^f$;
- each $R^{37}$, $R^{38}$ and $R^{39}$ is independently halo, —OH, —$CH_3$ or $R^f$;
- each m, n, and p is independently 0, 1, 2, 3 or 4;
- provided at least one and no more than two of $R^{31}$, $R^{32}$, $R^{34}$, $R^{34}$, $R^{35}$, $R^{36}$, $R^{37}$, $R^{38}$ and $R^{39}$ is $R^f$; wherein $R^f$ is a point of connection to L.

In one aspect the fluorescent moiety (F) is

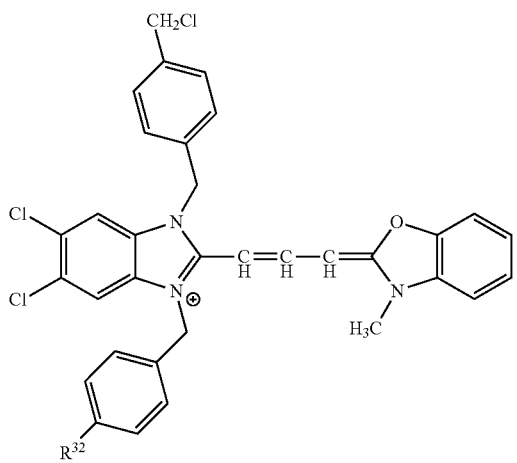

where $R^{32}$ is the point of connection to L.

(G) Linkers

The linker (L) of the present disclosure connects a fluorescent moiety or fluorophore to a small molecule compound. In a particular aspect the linker is a bond, i.e., the fluorescent moiety is linked to the small molecule compound directly.

In some embodiments, the attachment of the fluorescent moiety does not significantly reduce the activity of the drug (D), thereby the modified compound is biologically active and/or pharmaceutically effective. In some embodiments, the attachment of the fluorescent moiety reduces or eliminates the activity of the drug (D), thereby the modified compound has a reduced biological and/or pharmaceutical activity or alternatively is biologically inactive and/or pharmaceutically ineffective.

Other linkers suitable for this purpose include linkers well known for purposes of conjugating two molecules.

In some aspects the linker (L) is stable and does not degrade upon administration, and the conjugate of the fluorescent moiety and the drug is biologically and/or pharmaceutically active. Exemplary stable linkers include but are not limited to acetylalanine (see Example 2) and beta-alanine (see Example 3). In other aspects the linker has a half-life under physiological conditions (e.g., in a non-lyophilized state) that is longer than the minicell loading time such that the fluorescent moiety/fluorophore and the small molecule compound become separate upon breakdown of the linker after the modified compound is loaded into the minicell. Generally speaking, it takes about 4 hours to load the minicells. Thus, the half-life of the linker can be at least 4 hours, 6 hours, 8 hours, 10 hours, 12 hours, 14 hours, 16 hours, 18 hours, 20 hours, 22 hours, or 24 hours. Preferably, the half-life of the linker is within 6-24 hour or 8-24 hours. For example, when used as a linker the 2'-(3-aminopropanoyl) moiety has a half-life of about 8 hours.

In other aspects the linker is stable within the bacterial vesicle but can be pH-sensitive and, hence, is less stable at a pH lower than neutral. Since the pH in the endosome/lysosome is significantly lower than in the normal cellular environment, such a pH-sensitive linker is only degradable in the endosome/lysosome of a target mammalian cell. Under such acidic conditions the linker may be hydrolyzed. For example, esters may be hydrolyzed to an alcohol residue and a carboxylic acid, or amides may be hydrolyzed to an amine and a carboxylic acid.

That pH-sensitive linkers are known is illustrated, for instance, by Nie et al. in POLYMERIC BIOMATERIALS: MEDICINAL AND PHARMACEUTICAL APPLICATIONS, Chapter 16, pages 413-32 (Dumitriu ed., 2013), which describes acid-labile linkers used in drug delivery. International patent application WO2006/108052 also describes acid-labile linkers, which are degradable under conditions found in lysosomes. Duncan, *Nature Reviews Cancer* 6: 688-701 (2006), describes linkers degradable upon exposure to lysosomal enzymes, for example, Gly-Phe-Leu-Gly and polyglutamic acid (PGA) are cleaved by cathepsin B), or to lower pH, for instance, a hydrazone linker degrades in endosomes and lysosomes (pH 6.5 to pH<4.0). U.S. Pat. No. 5,306,809 describes acid-labile linkers that are suitable for immune therapies.

For example, U.S. Pat. No. 6,521,431 describes the use as linkers of glycolic or lactic acid, hydroxy esters, such as 3-hydroxy butyric acid, 2-hydroxy propanoic acid, and 5-hydroxy caproic acid, amino acids, ortho-esters, anhydrides, phosphazines, phosphoesters.

Published application US2013/0071482 describes linkers having one or more moieties such as

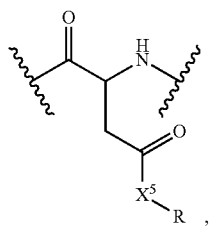

where $X^5$ is O or NH and structures for R are detailed in the '482 published application.

Published application US2013/0261094 describes linkers such as:

—OQ-$(CH_nH_{2n})$—S(R'(R''))—$(C_mH_{2m})$—$CH_2$-A or —$R^9$N-Q-$(C_nH_{2n})$—S(R')(R'')—$(C_mH_{2m})$—$CH_2$-A, where n and m are integers from 0 to 20, and preferably from 1 to 10; R' and R'' are independently an electron lone pair, an oxygen moiety such as =O, or a nitrogen moiety such as =N—$R^x$, wherein $R^x$ is a homo- or heterogenous group of atoms; A is a conjunction moiety; and Q is a direct bond, a C=O, a C=NH or C=$NR^p$ group, wherein $R^p$ is a $C_1$-$C_3$ alkyl and $R^9$ can either be a hydrogen atom or a $C_1$-$C_3$ alkyl group.

Published application US2012/0121615 describes linkers such as

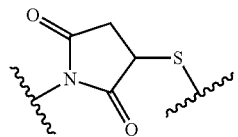 [SMILES: *SC1CC(=O)N(*)C1=O]

or

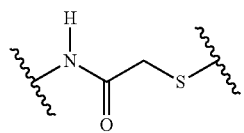

Published application US20050112065 describes pH-sensitive linkers, such as citraconyl or hydrazide linkers, or enzymatically-sensitive linkers. Examples of such linkers, which the application details, include:

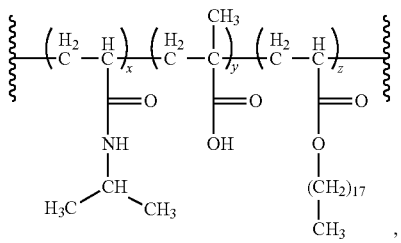

where x, y, z are independently 0, 1, 2, 3, 4 or 5, with the proviso that at least one of x, y, and z is not 0. In some embodiments, x, y, and z are independently 1, 2, 3, 4, or 5.

Nicoletti et al., *Int'l J. Antimicrob. Agents* 33: 441-8 (2009), describes polypeptide GlyPheLeuGly as a linker.

The respective contents of the above-mentioned publications are incorporated here in their entirety by reference. Some publications use the name of a given compound when describing a linker. In any event, any given compound presents a divalent radical when acting as a linker, such that it can link a drug and a fluorescent moiety to provide a modified (fluorescent) compound in accordance with the invention.

In one aspect the linker (L) is selected from the group consisting of a bond, —C(O)—O—, —C(O)NH—, —OC(O)—$(CHR^{50})_q$$NR^{51}$C(O)—, and —OC(O)—$(CHR^{50})_q$C(O)$NR^{51}$—$(CHR^{52})_u$—NH—C(S)—NH—, where $R^{50}$, $R^{51}$ and $R^{52}$ are independently H or $C_{1-4}$ alkyl, and q and u are independently 1, 2, 3, 4, 5, 6 or 7.

In another aspect L is selected from the group consisting of: —O—C(O)—CH($CH_3$)—NHC(O)—, —O—C(O)—$(CH_2)_2$NH—CO—, and —O—C(O)—$(CH_2)_3$C(O)NH—$(CH_2)$—NH—C(S)—NH—.

In some aspects the linker is —$(CHR^{52})_p$—, where at least one of —$(CHR^{52})$— is replaced with one from the group of —O—, —$(CHR^{52})$—O—$)_q$, —S—, —S—S—, —C(O)NH—, —C(O)O—, and —$CR^{52}$=NNH, where $R^{52}$ is H or $C_{1-4}$ alkyl; and where p is an integer selected from 2-10 and q is an integer selected from 1-7. In some embodiments, p is an integer of from 2 to 10, inclusive, and q is an integer from 1 to 7, inclusive.

(H) Treatment Methods and Compositions

Pursuant to a further aspect of this disclosure, the compound-loaded, intact and nonliving bacterial vesicles of a composition as described above are directed to a target mammalian tumor cell via a ligand. In some embodiments the ligand is "bispecific." That is, the ligand displays a specificity for both minicell and mammalian (tumor) cell components, such that it causes a given vesicle to bind to the target cell, whereby the latter engulfs the former. Use of bispecific ligands to target a minicell to a tumor cell is further described in WO 05/056749 and WO 05/079854, and use of bispecific ligands to target a killed bacterial cell to a tumor cell is further described in U.S. Pat. No. 8,591,862, the respective contents of which are incorporated here by reference in its entirety. Once such a ligand is attached to a vesicle, the unoccupied specificity ("monospecificity") of the ligand pertains until it interacts with the target (tumor) mammalian cell.

The ligand can be attached to the cell membrane of the vesicles by virtue of the interaction between the ligand and a component on the cell membrane, such as a polysaccharide, a glycoprotein, or a polypeptide. The expressed ligand is anchored on the surface of a vesicle such that the surface component-binding portion of the ligand is exposed so that the portion can bind the target mammalian cell surface component when the vesicle and the mammalian cell come into contact.

Alternatively, the ligand can be expressed and displayed by a living counterpart of a bacterially derived vesicle, e.g., by the parent cell of a minicell or by a bacterial cell before it becomes a killed cell. In this instance the ligand does not require a specificity to the vesicle and only displays a specificity to a component that is characteristic of mammalian cells. That is, such component need not be unique to tumor cells, per se, or even to the particular kind of tumor cells under treatment, so long as the tumor cells present the component on their surface.

Upon intravenous administration, vesicles accumulate rapidly in the tumor microenvironment. This accumulation, occurring as a function of the above-described leaky tumor vasculature, effects delivery of vesicle-packaged therapeutic payload to cells of the tumor, which then internalize packaged vesicles.

The inventors have found that this delivery approach is applicable to a range of mammalian tumor cells, including cells that normally are refractory to specific adhesion and endocytosis of minicells. For instance, ligands that comprise an antibody or antibody derivative (see below) directed at an anti-HER2 receptor or anti-EGF receptor can bind minicells to the respective receptors on a range of targeted non-phagocytic cells, such as lung, ovarian, brain, breast, prostate, and skin cancer cells.

The binding thus achieved precedes uptake of the vesicles by each type of non-phagocytic cells. That is, in the context of the present invention a suitable target cell presents a cell surface component the binding of which, by a ligand on a vesicle, elicits endocytosis of that vesicle.

More specifically, the present inventors discovered that the interaction between (a) the ligand on a minicell or a killed bacterial cell and (b) a mammalian cell surface receptor can activate an uptake pathway, called here a "receptor-mediated endocytosis" (rME) pathway, into the late-endosomal/lysosomal compartment of the target host cell, such as a tumor cell. By this rME pathway, the inventors found, bacterially derived vesicles are processed through the early endosome, the late endosome and the lysosome, resulting in release of their payload into the cytoplasm of the mammalian host cell. Moreover, a payload that is a nucleic acid not only escapes complete degradation in the late-endosomal/lysosomal compartment but also is expressed by the host cell.

A ligand for this delivery approach can be "bispecific," as described above, because it binds to surface components on a payload-carrying vesicle and on a target cell, respectively, and its interaction with the latter component leads to uptake of the vesicle into the rME pathway. In any event, a given target cell-surface component can be a candidate for binding by the ligand, pursuant to the invention, if interaction with the component in effect accesses an endocytic pathway that entails a cytosolic internalization from the target cell surface. Such candidates are readily assessed for suitability in the invention via an assay in which a cell type that presents on its surface a candidate component is co-incubated in vitro with minicells carrying a ligand that binds the candidate and that also is joined to a fluorescent dye or other marker amenable to detection, e.g., visually via confocal microscopy. (An in vitro assay of this sort is described by MacDiarmid et al. (2007), in the legend to FIG. 3 at page 436.) Thus, an observed internalization of the marker constitutes a positive indication by such an assay that the tested target cell-surface component is suitable for the present invention.

Figure 24:
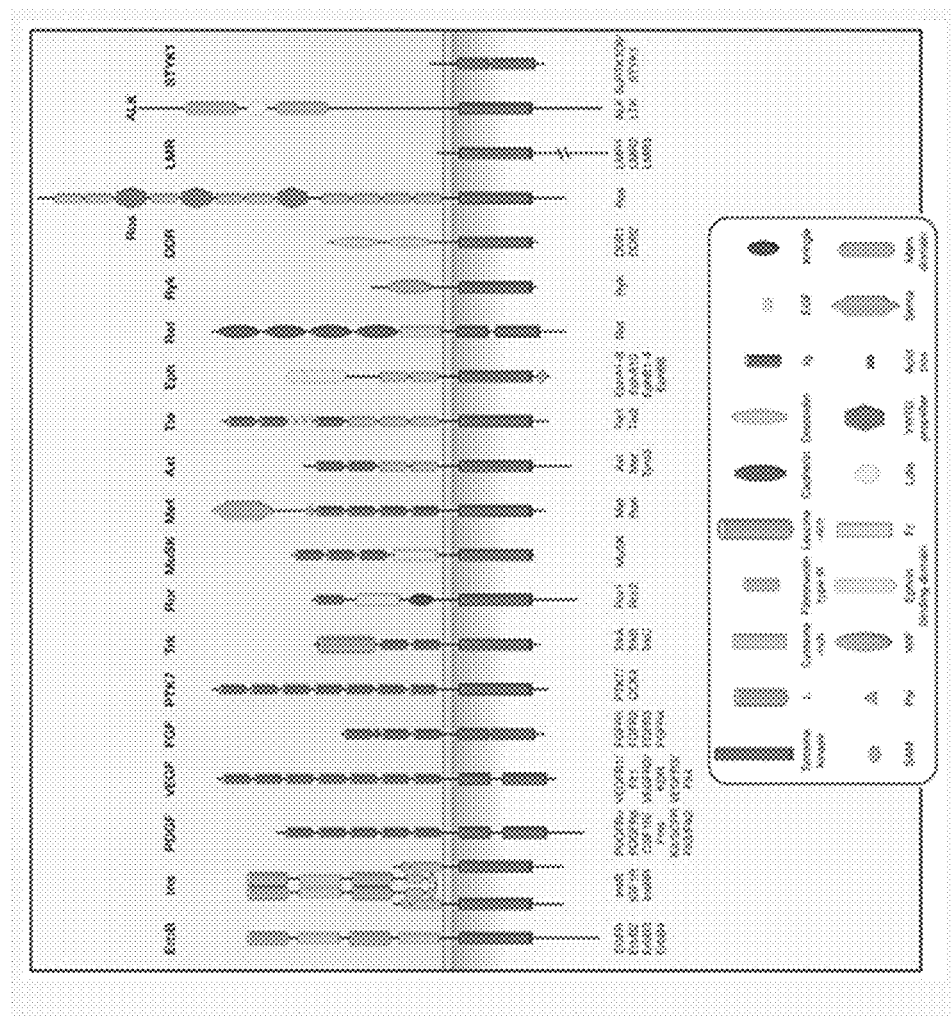
FIG. 24 illustrates 20 subfamilies and 58 members of human receptor tyrosine kinases (excerpted from Lemmon and Schlessinger, *Cell* 141: 1117-134 (2010)).

Illustrative of candidate target cell-surface components are members of (A) the receptor tyrosine kinases or "RKTs," a family of transmembrane proteins that undergo constitutive internalization (endocytosis) at a rate similar to that of other integral membrane proteins. See Goh and Sorkin, *Cold Spring Harb. Perspect. Biol.* 5: a017459 (2013). The family of RKTs is described, for instance, by Lemmon and Schlessinger, *Cell* 141: 1117-134 (2010). The table below lists, in twenty subfamilies, all fifty-eight RTKs in the human proteome, any one or more of which may be tested for suitability in the invention, as described above (see also FIG. 24).

TABLE 1

| RTK Subfamilies | Exemplary RTKs |
| --- | --- |
| ErbB | EGFR, ErbB2, ErbB3, ErbB4 |
| Ins | InsR, IGF1R, InsRR |
| PDGF | PDGFRα, PDGFRβ, CSF1R/Fms, Kit/SCFR, Fit3/Flk2 |
| VEGF | VEGFR1/Fit1, VEGFR2/KDR, VEGFR3/Fit4 |
| FGF | FGFR1, FGFR2, FGFR3, FGFR4 |
| PTK7 | PTK7/CCK4 |
| Trk | TrkA, TrkB, TrkC |
| Ror | Ror1, Ror2 |
| MuSK | MuSK |
| Met | Met, Ron |
| Axl | Axl, Mer, Tyro3 |
| Tie | Tie1, Tie2 |
| Eph | EphA1-8, EphA10, EphB1-4, EphB6 |
| Ret | Ret |
| Ryk | Ryk |
| DDR | DDR1, DDR2 |
| Ros | Ros |
| LMR | LMR1, LMR2, LMR3 |
| ALK | ALK, LTK |
| STYK1 | SuRTK106/STYK1 |

Likewise illustrative are members of: (B) the class of membrane-associated, high-affinity folate binding proteins (folate receptor), which bind folate and reduced folic acid derivatives and which mediate delivery of tetrahydrofolate to the interior of cells, (C) the subgroup of membrane-bound cytokine receptors that play a role in the internalization of a cognate cytokine, such as IL13; (D) the surface antigens, such as CD20, CD33, mesothelin and HM1.24, that are expressed on certain cancer cells and that mediate the internalization of cognate monoclonal antibodies, e.g., rituximab in the instance of CD20; and (E) the family of adhesion receptors (integrins), transmembrane glyproteins that are trafficked through the endosomal pathway and are major mediators of cancer cell adhesion to extracellular matrix.

In accordance with the invention, the ligand can be any polypeptide or polysaccharide that exhibits the desired specificity or specificities, as the case may be. Preferred ligands are antibodies. In its present use the term "antibody" encompasses an immunoglobulin molecule obtained by in vitro or in vivo generation of an immunogenic response. Accordingly, the "antibody" category includes monoclonal antibodies and humanized antibodies, as well as antibody derivatives, such as single-chain antibody fragments (scFv), bispecific antibodies, etc. A large number of different bispecific protein and antibody-based ligands are known, as evidenced by the review article of Caravella and Lugovskoy, *Curr. Opin. Chem. Biol.* 14: 520-28 (2010), which is incorporated here by reference in its entirety. Antibodies useful in accordance with the present disclosure can be obtained as well by known recombinant DNA techniques.

By way of non-limiting example, therefore, an antibody that carries specificity for a surface component, such as a tumor antigen, can be used to target minicells to cells in a tumor to be treated, pursuant to the invention. Illustrative cell surface receptors in this regard include any of the RTKs epidermal growth factor receptor (EGFR), vascular endothelial growth factor receptor (VEGFR), platelet-derived growth factor receptor (PDGFR) and insulin-like growth factor receptor (IGFR), each of which is highly expressed in several solid tumors, including brain tumors, and folate receptor, which is overexpressed in some pituitary adenomas. Such a bispecific ligand can be targeted as well to mutant or variant receptors, e.g., the IL-13Rα2 receptor, which is expressed in 50% to 80% of human glioblastoma multiforme tumors, see Wykosky et al., *Clin Cancer Res.* 14: 199-208 (2008), Jarboe et al., *Cancer Res.* 67: 7983-86 (2007), Debinski et al., *J. Neurooncol.* 48: 103-11 (2000), and Okada et al., *J. Bacteriol.* 176: 917-22 (1994), but which differs from its physiological counterpart IL4R/IL13R, expressed in normal tissues. See Hershey, *J. Allergy Clin. Immunol.* 111: 677-90 (2003). Thus, IL13Rα2 is virtually absent from normal brain cells. See Debinski and Gibo, *Mol. Med.* 6: 440-49 (2000). Additionally, tumors that metastasize to the brain may overexpress certain receptors, which also can be suitable targets. For instance, Da Silva et al., *Breast Cancer Res.* 12: R46 (1-13) (2010), showed that brain metastases of breast cancer expressed all members of the HER family of RTKs. HER2 was amplified and overexpressed in 20% of brain metastases, EGFR was overexpressed in 21% of brain metastases, HER3 was overexpressed in 60% of brain metastases and HER4 was overexpressed in 22% of brain metastases. Interestingly, HER3 expression was increased in breast cancer cells residing in the brain.

(I) Formulations and Administration Routes and Schedules

Formulations of a composition of the disclosure can be presented in unit dosage form, e.g., in ampules or vials, or in multi-dose containers, with or without an added preservative. The formulation can be a solution, a suspension, or an emulsion in oily or aqueous vehicles, and can contain formulatory agents, such as suspending, stabilizing and/or dispersing agents. A suitable solution is isotonic with the blood of the recipient and is illustrated by saline, Ringers solution, and dextrose solution. Alternatively, formulations can be in lyophilized powder form, for reconstitution with a suitable vehicle, e.g., sterile, pyrogen-free water or physiological saline. The formulations also can be in the form of a depot preparation. Such long-acting formulations can be administered by implantation (for instance, subcutaneously or intramuscularly) or by intramuscular injection.

In some aspect, a vesicle-containing composition that includes a therapeutically effective amount of a small molecule compound is provided. A "therapeutically effective" amount of an anti-neoplastic agent is a dosage of the agent in question, in accordance with the present disclosure. If the small molecule compound is in an inactive form in the vesicle, then the "therapeutically effective" amount refers to the amount of the inactive compound that releases an effective amount of activated compound in the endosome/lysosome of a target cell.

In the context of the present disclosure, therefore, a therapeutically effective amount can be gauged by reference to the prevention or amelioration of the tumor or a symptom of the tumor, either in an animal model or in a human subject, when minicells carrying a therapeutic payload are administered, as further described below. An amount that proves "therapeutically effective amount" in a given instance, for a particular subject, may not be effective for 100% of subjects similarly treated for the tumor in question, even though such dosage is deemed a "therapeutically effective amount" by knowledgeable clinician. The appropriate dosage in this regard also will vary as a function, for example, of the type, stage, and severity of the tumor. In any event, the present illustrations of in vitro testing (Examples 3 and 4) and in vivo testing (Examples 5, 7 and 8) according to the present disclosure, as well as of methodology for quantifying the distribution of drug in vivo (Example 9), when considered in light of the entire description, empower a person knowledgeable in pre-clinical and clinical testing of drug candidates to determine, through routine experimentation, the therapeutically effective amount of active agent for a particular indication. Likewise, when "therapeutically effective" is used to refer to the number of minicells in a pharmaceutical composition, the number can be ascertained based on what anti-neoplastic agent is packaged into the minicells and the efficacy of that agent in treating a tumor. The therapeutic effect in this regard can be measured with a clinical or pathological parameter such as tumor mass. Accordingly, reduction or reduced increase of tumor mass can be used to measure therapeutic effects.

Formulations within the disclosure can be administered via various routes and to various sites in a mammalian body, to achieve the therapeutic effect(s) desired, either locally or systemically. In a particular aspect, the route of administration is intravenous injection.

In general, formulations of the disclosure can be used at appropriate dosages defined by routine testing, to obtain optimal physiological effect, while minimizing any potential toxicity. The dosage regimen can be selected in accordance with a variety of factors including age, weight, sex, medical condition of the patient; the severity or stage of the tumor, the route of administration, and the renal and hepatic function of the patient.

Optimal precision in achieving concentrations of vesicle and therapeutic agent within the range that yields maximum efficacy with minimal side effects can, and typically will, require a regimen based on the kinetics of agent availability to target sites and target cells. Distribution, equilibrium, and elimination of vesicles or agent can be considered when determining the optimal concentration for a treatment regimen. The dosage of vesicles and therapeutic agent, respectively, can be adjusted to achieve desired effects.

Moreover, the dosage administration of the formulations can be optimized using a pharmacokinetic/pharmacodynamic modeling system. Thus, one or more dosage regimens can be chosen and a pharmacokinetic/pharmacodynamic model can be used to determine the pharmacokinetic/pharmacodynamic profile of one or more dosage regimens. Based on a particular such profile, one of the dosage regimens for administration then can be selected that achieves the desired pharmacokinetic/pharmacodynamic response. For example, see WO 00/67776.

A formulation of the disclosure can be administered at least once a week to a tumor patient, over the course of several weeks. Thus, the formulation can be administered at least once a week, over a period of several weeks to several months.

More specifically, inventive formulations can be administered at least once a day for about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days. Alternatively, the formulations can be administered about once every day or about once every about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days or more.

In another embodiment of the disclosure, formulations can be administered about once every week or about once every about 2, about 3, about 4, about 5, about 6, about 7, about 8, about 9, about 10, about 11, about 12, about 13, about 14, about 15, about 16, about 17, about 18, about 19 or about 20 weeks or more. Alternatively, the formulations can be administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more.

Alternatively, the formulations can be administered about once every month or about once every about 2, about 3, about 4, about 5, about 6, about 7, about 8, about 9, about 10, about 11 or about 12 months or more.

The formulations can be administered in a single daily dose. Alternatively, the total daily dosage can be administered in divided doses of two, three, or four times daily.

The present invention, thus generally described, will be understood more readily by reference to the following examples, which are provided by way of illustration and are not intended to be limiting of the present invention. All publicly available documents referenced herein, including but not limited to patents, are specifically incorporated by reference.

EXAMPLES

The inventors observed the effect of a fluorescence-related loading enhancement across a broad range of loaded compounds differing in fluorescence type (intrinsic versus extrinsic) and in compound structure. For extrinsically fluorescent compounds, differences concerned the nature, respectively, of the fluorophore and of the linker, if any.

In general, the examples relate the loading of a variety of fluorescent compounds into bacterially derived, intact vesicles. For all of the examples the starting material was a buffered composition of empty, intact minicells, derived from a minCDE-chromosomal deletion mutant of *Salmonella enterica* serovar Typhimurium (*S. typhimurium*), with a free endotoxin level of no more than about 5 EU per $10^9$ minicells. See U.S. Pat. No. 8,449,877 (production of minicell compositions that are substantially lacking in free endotoxin).

For loading vesicles (here, minicells), the methodology in Examples 1-5, 7-10, 12, and 13 essentially conform with the small-scale protocol, described above and illustrated in MacDiarmid et al. (2007). For instance, in a given experiment empty minicells in PBS buffer could be added to a microfuge tube and centrifuged (16,000 g, 10 minutes). After the resulting supernatant was discarded, the minicell pellet would be resuspended in PBS buffer, optionally with 0.01 (w/v) gelatin added (so-called "BSG buffer"), and incubated with the payload compound, generally at about 200 μg to about 1 mg per ml of minicell suspension. The loaded minicells thus obtained would be centrifuged (16,000 g, 10 minutes), and the loading supernatant discarded. Loaded minicells then would be washed by resuspending the pellet in 1 ml of buffer, centrifuging the minicells (16,000 g, 10 minutes), and discarding the supernatant wash. Such a wash step usually was repeated three times. Finally, the minicells would be resuspended in PBS or BSG buffer.

When the fluorescent compound to be loaded is water-soluble, as was the case for many of the aforementioned examples, trapping of compound to vesicle outer surfaces is reduced in significance. As a consequence washing in small scale suffices, permitting use of the small-scale protocol. In Examples 6 and 11, however, the loaded compound was doxorubicin, which is amphipathic rather than hydrophilic, and so trapping is a significant factor. Accordingly, while the loading step for these examples was in small scale, i.e., loading took place in about milliliter-scale volumes of buffered liquid, the washing steps involved cross-filtration (no centrifugation) with liter-scale volumes of buffered liquid, thus constituting a large-scale process.

Finally, Example 14 compares the small-scale protocol with the large-scale process, highlighting improved consistency and purity achieved with the latter.

In the examples the payload-packaged minicells were mounted onto glass slides for visualization by fluorescence microscopy, using a Leica model DM LB light microscope, 100× magnification (Leica Microsystems, Germany). The results were captured using a Leica DC camera and Leica IM image management software, with appropriate filter employed to permit visualization of payload fluorescence.

Example 1. Loading of Vinblastine BODIPY® FL

This example demonstrates packaging into the cytoplasm of bacterially derived minicells of a fluorescent conjugate of vinblastine. Vinblastine is an antimicrotubule drug conventionally used to treat certain kinds of cancer, including Hodgkin's lymphoma, non-small cell lung cancer, breast cancer, head and neck cancer, and testicular cancer.

The employed compound, Vinblastine BODIPY® FL, is available commercially and was obtained from Life Technologies (Thermo Fisher Scientific), Molecular Probes® brand. The compound is a conjugate vinblastine, via a methylene linker, with the fluorescent dye BODIPY® FL. Other BODIPY fluorophores, such as BODIPY R6G, BODIPY TMR, BODIPY 581/591, BODIPY TR, BODIPY 630/650 and BODIPY 650/665, could be substituted for BODIPY® FL in this context. See THE MOLECULAR PROBES® HANDBOOK—A GUIDE TO FLUORESCENT PROBES AND LABELING TECHNOLOGIES (11th ed.), Section 1.4, "BODIPY Dye Series," the contents of which are incorporated here by reference.

Vinblastine BODIPY® FL has well-defined fluorescent characteristics (excitation 505 nm, emission 513 nm; red fluorescence). Its structure is depicted below.

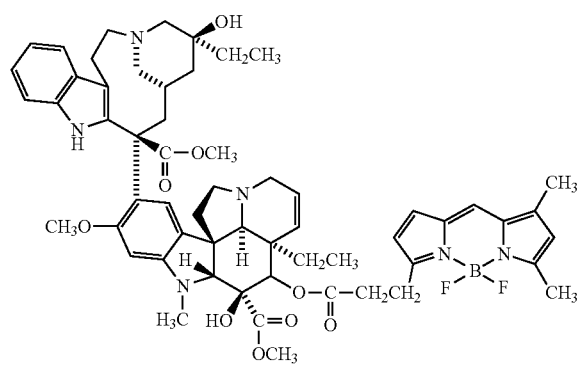

With a starting composition containing empty minicells, Vinblastine BODIPY® FL was loaded (incubation in 1 mg conjugate per ml solution) and was washed in accordance with the small-scale protocol, with the washing step repeated three times. The results of fluorescent imaging (FIG. 1) revealed that all of the loaded minicells fluoresced bright red, indicating that Vinblastine BODIPY® FL had been transferred into the minicell cytoplasm. In addition, Vinblastine BODIPY® FL molecules remained within the minicells despite the reversal of the concentration gradient throughout the washing steps.

Example 2. Loading of FLUTAX-1

This example demonstrates packaging into the cytoplasm of intact, bacterially derived vesicles of a fluorescent conjugate of paclitaxel. Paclitaxel is a taxane that stabilizes microtubules and, as a result, interferes with the normal breakdown of microtubules during cell division. As a mitotic inhibitor paclitaxel is used in chemotherapy to treat lung, ovarian, and breast cancers, head and neck cancer, and advanced forms of Kaposi's sarcoma.

The employed fluorescent taxane derivative FLUTAX-1 is a commercially available conjugate of paclitaxel with fluorescein via an acetylalanine linker. Conventionally, FLUTAX-1 is deemed therapeutically ineffective; hence, it is marketed as a research reagent only. For this example the conjugate was obtained from a commercial source, Tocris Biosciences (Bristol, UK).

FLUTAX-1 (molecular weight: 1283.2 has well-defined fluorescent characteristics (excitation ~495 nm, emission ~520 nm; green fluorescence). The formal name of the derivative is 2aR,4S,4aS,6R,9S,11S,12S,12aR,12bS)-6,12b-Bis(acetyloxy)-9-[(2R,3S)-3-(benzoylamino)-2-hydroxy-1-oxo-3-phenylpropoxy]-12-(benzoyloxy)-2a,3,4,4a5,6,9,10,11,12,12a,12b-dodecahydro-11-hydroxy-4a,8,13,13-tetramethyl-5-oxo-7,11-methano-1H-cyclodeca[3,4]benz[1,2-b]oxet-4-yl ester N-[(3',6'-dihydroxy-3-oxospiro[isobenzofuran-1(3H),9'-[9H]xanthen]-5-yl)caronyl]-L-alanine. Its chemical structure is depicted below.

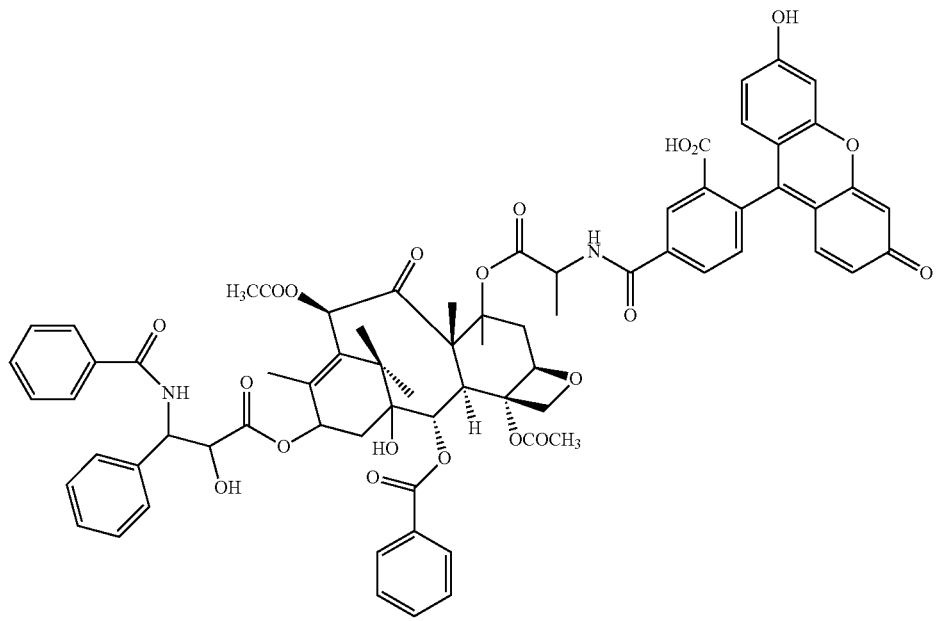

Minicells in PBS, prepared as described above, were incubated with 200 µg/ml FLUTAX-1 solution in 1 ml and then were washed repeatedly, pursuant to the small-scale protocol.

Figure 2:
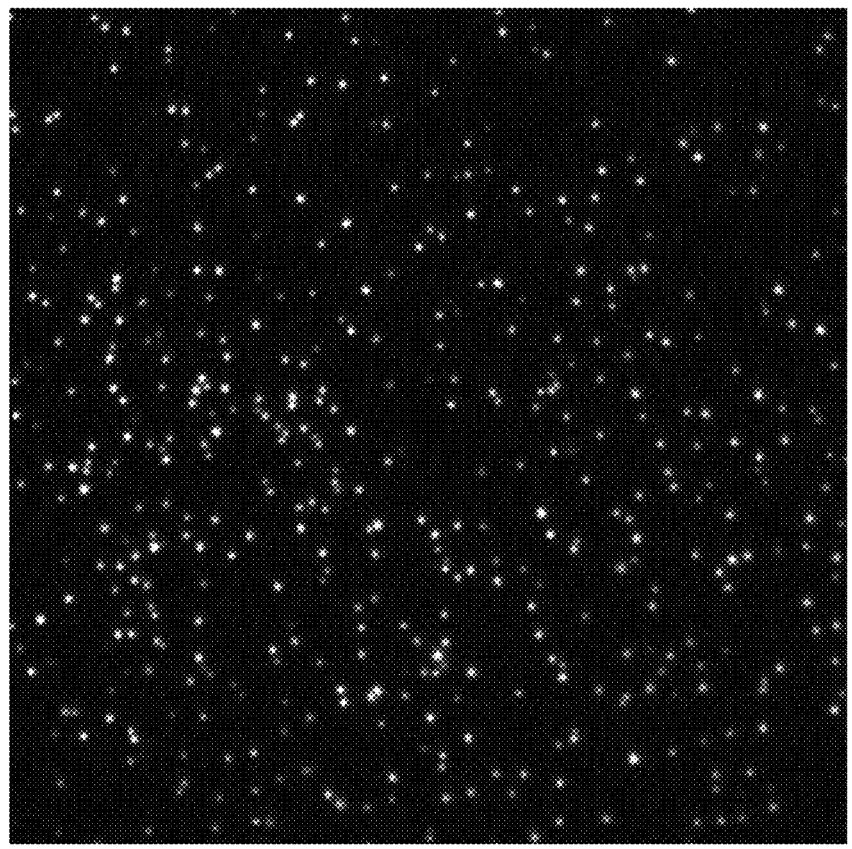
FIG. 2 shows a fluorescent image of minicells packaged with FLUTAX-1. The minicells fluoresce bright green on a black background. Accordingly, FLUTAX-1 was packaged into the minicells and did not remain in the exterior space.

Fluorescent imaging (FIG. 2) revealed that all of the minicells fluoresced bright green suggesting that FLUTAX-1 had been transferred into the minicell cytoplasm and that a large number of FLUTAX-1 molecules remained encapsulated despite the reversal of the concentration gradient throughout the washing steps. The background appeared black in comparison to the FLUTAX-1 packaged minicells, evidencing little to no exterior FLUTAX-1.

The quantity of FLUTAX-1 packaged within the minicells was determined by extracting the drug from the minicells, followed by HPLC analysis and comparison to a standard curve of FLUTAX-1 samples of known concentration. Minicell extraction was performed as described by MacDiarmid et al. (2007), supra, for minicells packaged with doxorubicin. An HPLC method was developed for the quantification of FLUTAX-1. The HPLC method characteristics included (i) Mobile phase: acetonitrile: MilliQ $dH_2O$, 50:50, isocratic elution for 12 minutes at flow rate 2 ml/minute. (ii) Stationary phase: Metalchem 3u Taxsil, 100 mm×4.6 mm plus C18 cartridge. (iii) Column temperature: 40° C. (iv) Detection: (a) SPD-M10Avp diode array detector-228 nm (b) RF-10AXL fluorescence detector (Shimadzu)-Excitation 495 nm, emission 520 nm. (v) Injection volume: 50 µl. (vi) HPLC system: A Shimadzu SCL-10AVP system comprising SIL-10AVP auto-injector, LC-10Advp pump, DGU-14A degasser, CTO-10Avp column oven, RF-10AXL fluorescence detector and SPD-M10Avp diode array detector with Class-VP version 7.2.1 software (Shimadzu corporation, Kyoto, Japan).

Figure 3:
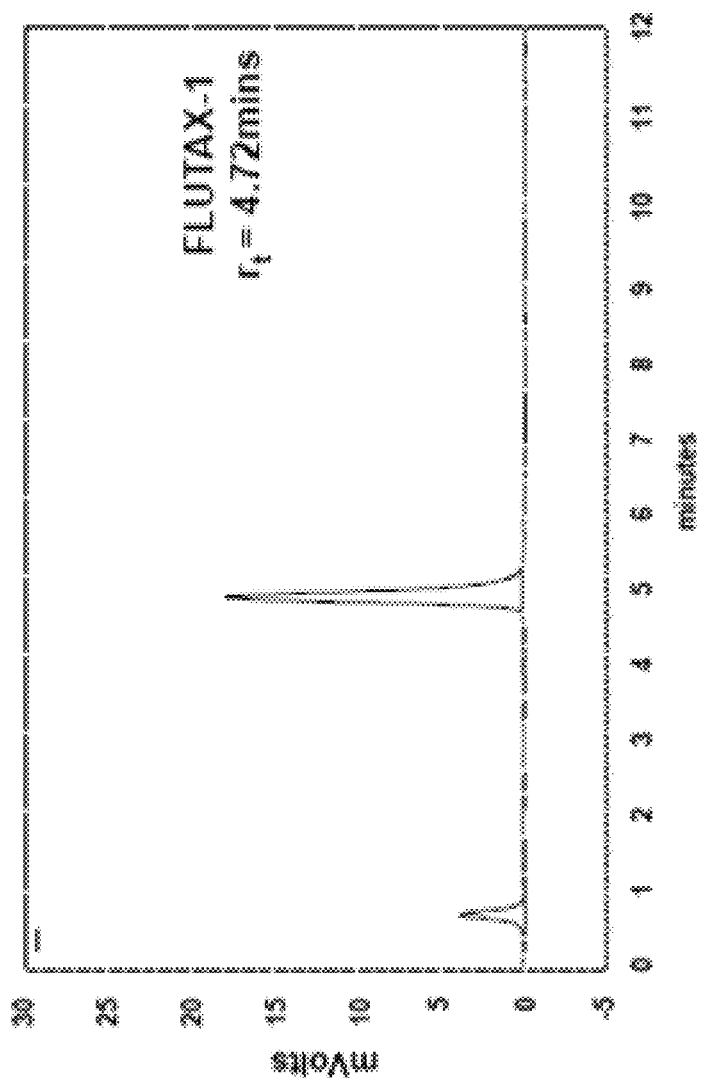
FIG. 3 shows an example chromatogram from an HPLC separation of an extract from $1\times10^9$ FLUTAX-1-packaged minicells. The peak corresponding to FLUTAX-1 is found at the retention time $(r_t)$=4.72 minutes. The area of this peak was used to calculate the quantity of FLUTAX-1 packaged into the minicells by comparing to a standard curve of FLUTAX-1 of known quantities.

FLUTAX-1 content obtained with these drug loading conditions was determined by HPLC to be 570 ng per $1\times10^9$ minicells (FIG. 3). By use of Avogadmo's number this equates to ~270,000 molecules of FLUTAX-1 packaged per minicell, a significant improvement upon paclitaxel packaging, with 127-fold more FLUTAX-1 molecules than paclitaxel molecules per minicell (see Example 9, infra). This is surprising as well because TF.Pac, the water-soluble derivative of paclitaxel, provided only 25-fold more molecules per minicell (see Example 10). The results indicate that the fluorescein fluorophore enhances FLUTAX-1 entry and retention in the minicell.

Example 3. Loading of Paclitaxel Oregon Green®-488

This example demonstrates that another fluorescent paclitaxel conjugate, Paclitaxel Oregon Green®-488 a/k/a "FLUTAX-2," can be packaged into the cytoplasm of intact, bacterially derived vesicles. For this derivative a fluorinated fluorescein moiety, Oregon Green-488, is conjugated to C7 of paclitaxel via a beta-alanine linker. The fluorinated fluorescein moiety confers fluorescence (excitation ~495 nm, emission ~525 nm; green fluorescence) as well as improved water solubility to the derivative molecule.

The involved derivatization of paclitaxel yields a biologically inactive and hence therapeutically ineffective chemical entity, marketed only for research purposes. Paclitaxel Oregon Green-488 is commercially available, therefore, and for this example it was obtained from the Life Technologies (Thermo Fisher Scientific).

The formal name of the derivative is L-alanine, N-[(2', 7'-difluoro-3',''-dihydroxy-3-oxospiro[isobenzofuran-1(3H), 9'-[9H]xanthen]-5-yl)carbonyl]-(2aR,4S,4aS,6R9S,11S, 12S,12aR,12bS)-6,12b-bis(acetyloxy)-12-(benzoyloxy)-9-[(2R,3S)-3-(benzoylamino)-2-hydroxy-1-oxo-3-phenylpropoxy]-2a3,4,4,5,6,9,10,11,12,12a,12b-dodecahydro-11-hydroxy. Its chemical structure is represented below.

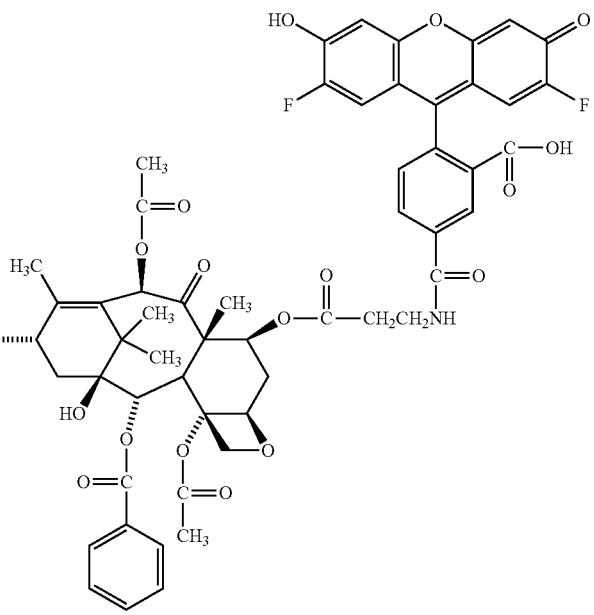

Figure 4:
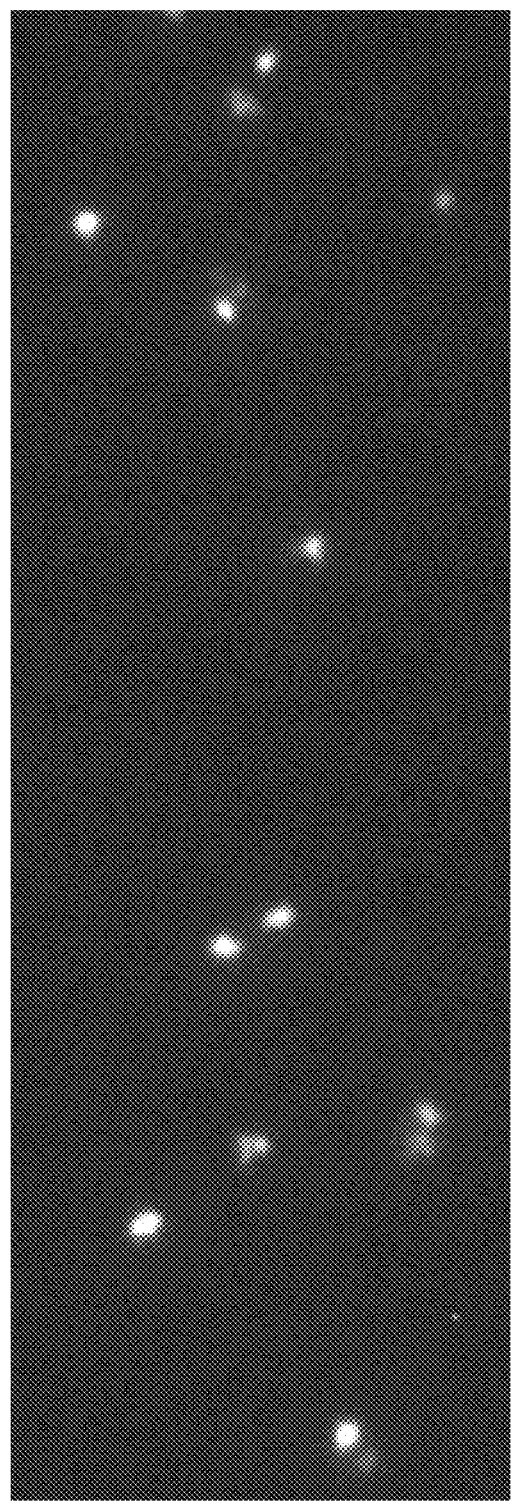
FIG. 4 shows a fluorescent image of minicells packaged with paclitaxel conjugated with Oregon® Green-488. That the minicells fluoresce bright green on a black background shows that the conjugate is packaged into the minicells.

Minicells in PBS were prepared, loaded (100 µg/ml external loading concentration of conjugate solution), and washed in accordance with the small-scale protocol. Fluorescent imaging (FIG. 4) revealed that all of the minicells fluoresced bright green indicating that Paclitaxel Oregon Green®-488 had been transferred into the minicell cytoplasm and that a large number of conjugate molecules had remained in the minicells even upon reversal of the concentration gradient throughout the washing steps. That the background appeared black in comparison to the loaded minicells evidenced little to no exterior Paclitaxel Oregon Green®-488.

The quantity of Paclitaxel Oregon Green®-488 packaged within the minicells has to be determined indirectly, since disruption of loaded minicells resulted in this instance in a breaking down of the loaded compound as well, thwarting quantitation by HPLC analysis. Accordingly, the intensity of (green) fluorescence in minicells loaded with Paclitaxel Oregon® Green-488, was compared, via fluorescence microscopy, with the (red) autofluorescence visualized for minicells loaded with doxorubicin, which is stable under conditions of extraction and quantitation. See Example 6, infra, showing ~800 ng doxorubicin packaged per $10^9$ minicells. In relation to the fluorescence observed with doxorubicin, that is, the high intensity of fluorescence observed for minicells loaded with Paclitaxel Oregon Green®-488 indicated a similar concentration for the latter, i.e., ~800 ng drug per $10^9$ minicells. This value contrasted with the value, observed for paclitaxel-loaded minicells, of less than 10 ng drug per $10^9$ minicells (Example 9, infra).

Example 4. Loading of FITC-Conjugated Paclitaxel

This example demonstrates efficient packaging into the cytoplasm of intact, bacterially derived vesicles of fluorescein isothiocyanate (FITC) derivative of paclitaxel, acronym "FCP." The fluorescein group, identical to the one found in FLUTAX-1, is conjugated via a 5-oxo-5-((6-thioureidohexyl)amino)pentanoic acid linker, i.e., a relatively long linker domain, to the C2' position rather than the C7 position on the paclitaxel molecule, as in FLUTAX-1 and Paclitaxel Oregon Green®-488. Here, too, the fluorescein group confers fluorescence to the derivative molecule (excitation: 495 nm; emission: 519 nm) and, with the linker, increases its aqueous solubility.

FCP is not biologically active and has been used to date for research purposes only. For this example FCP was obtained from IDT Australia Ltd. (Boronia, Victoria). Its chemical structure appears below.

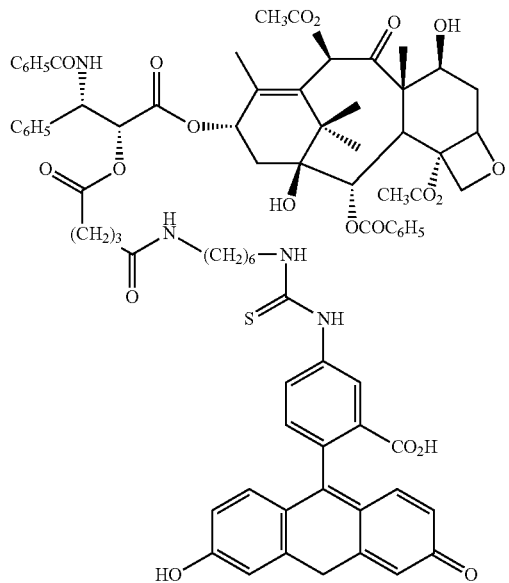

Figure 5:
FIG. 5 shows a fluorescent image of minicells packaged with FCP. The minicells fluoresce bright green on a black background, indicating that FCP is packaged into the minicells.

With a starting composition as described, minicells in PBS were prepared, were loaded via incubation with FCP solution (300 µg/ml), and were washed in accordance with the small-scale protocol. Fluorescent imaging (FIG. 5) revealed that all of the minicells fluoresced bright green, indicating that FCP had been transferred into the minicell cytoplasm and that reversal of the concentration gradient throughout the washing steps left a large number of FCP molecules encapsulated in the minicells. There was little to no exterior FCP, as reflected in the black appearance of the background relative to the FCP-packaged vesicles.

The quantity of FCP packaged within the minicells was determined by extracting the drug from the minicells, followed by HPLC analysis. Minicell extraction was performed and HPLC methodology was employed was as described for the quantification of FLUTAX-1, supra.

Figure 6:
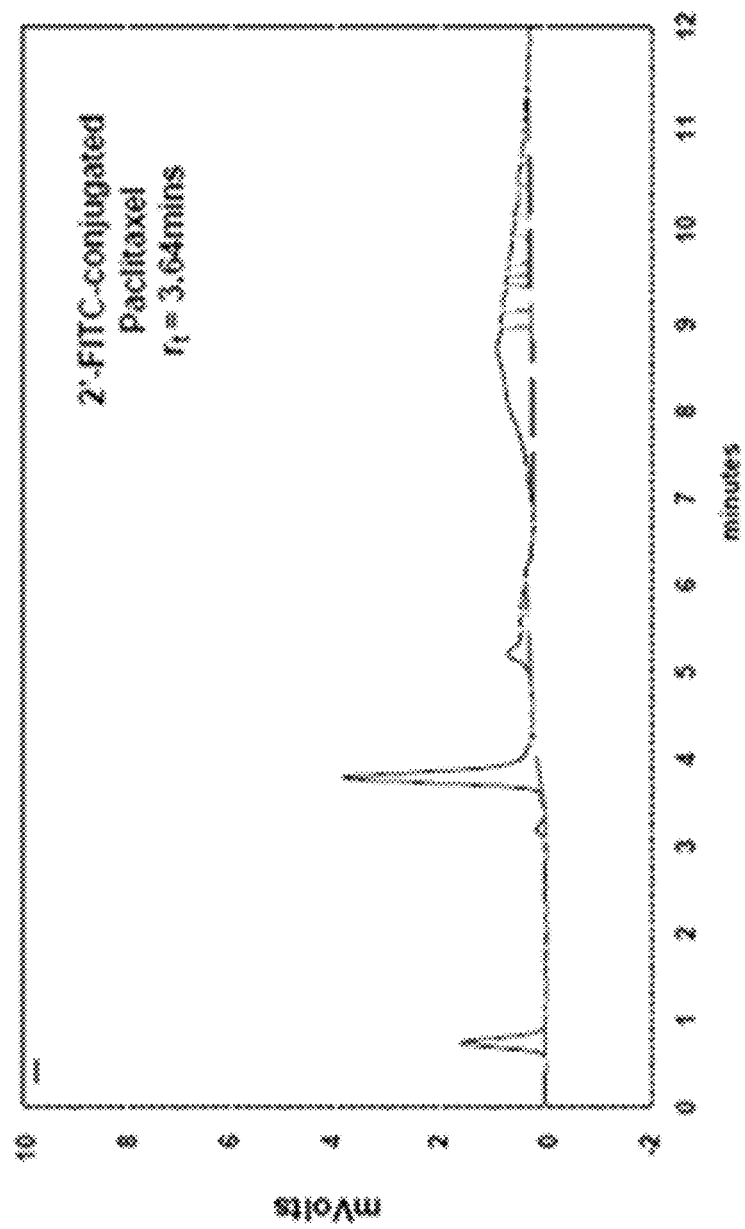
FIG. 6 shows an example chromatogram from an HPLC separation of an extract from FCP-loaded minicells ($1\times10^9$). The peak corresponding to FCP is found at the retention time $(r_t)$=3.64 minutes. The area of this peak was used to calculate the quantity of FCP packaged into the minicells by comparing to a standard curve of FCP of known quantities.

The FCP content obtained with these drug loading conditions was quantified as 550 ng per $1 \times 10^9$ minicells (FIG. 6). This equates to 230,000 molecules of FLCP packaged per minicell. This is a significant improvement upon paclitaxel packaging, with 109-fold more molecules per minicell, despite the fact that FCP is a larger molecule (formula weight 1455.6 versus 853.9).

The number of packaged FCP molecules is similar to that of FLUTAX-1 (~270,000). FCP and FLUTAX-1 have the same fluorophore. Yet conjugation differs, C2' (FCP) versus C7 (FLUTAX-1), while Paclitaxel Oregon Green®-488 shares the same C7 conjugation position as FLUTAX-1. Thus, the structure of the fluorescein fluorophore and not the point of conjugation to the molecule is shown to be critical for facilitating loading of the drug molecule into the minicell. Thus, the point of conjugation is shown to be non-critical to florescence-mediated enhancement of compound loading into intact, bacterially derived vesicles, according to the invention.

Example 5. Loading of BacLight™ Green

This example demonstrates that the bacterial stain BacLight™ Green can be readily packaged in intact, bacterially derived vesicles. A green-fluorescent dye (absorption/emission ~480/516 and ~581/644 nm, respectively), BacLight™ Green is commercially available and was obtained for this example from Life Technologies (Thermo Fisher Scientific), Molecular Probes® brand. Its chemical structure is depicted below.

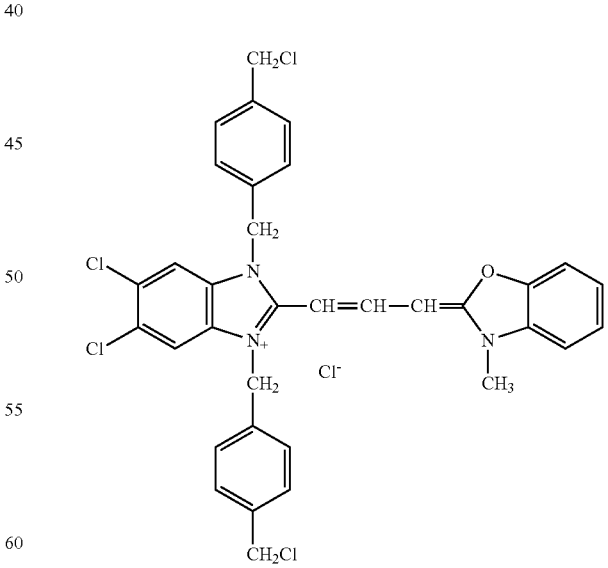

BacLight™ Green solution was added to minicells in PBS buffer to a final concentration of 200 nM. Pursuant to the small-scale protocol the minicells were incubated at room temperature for 30 minutes and were subjected to a thrice-repeated washing step, as described above.

Figure 7:
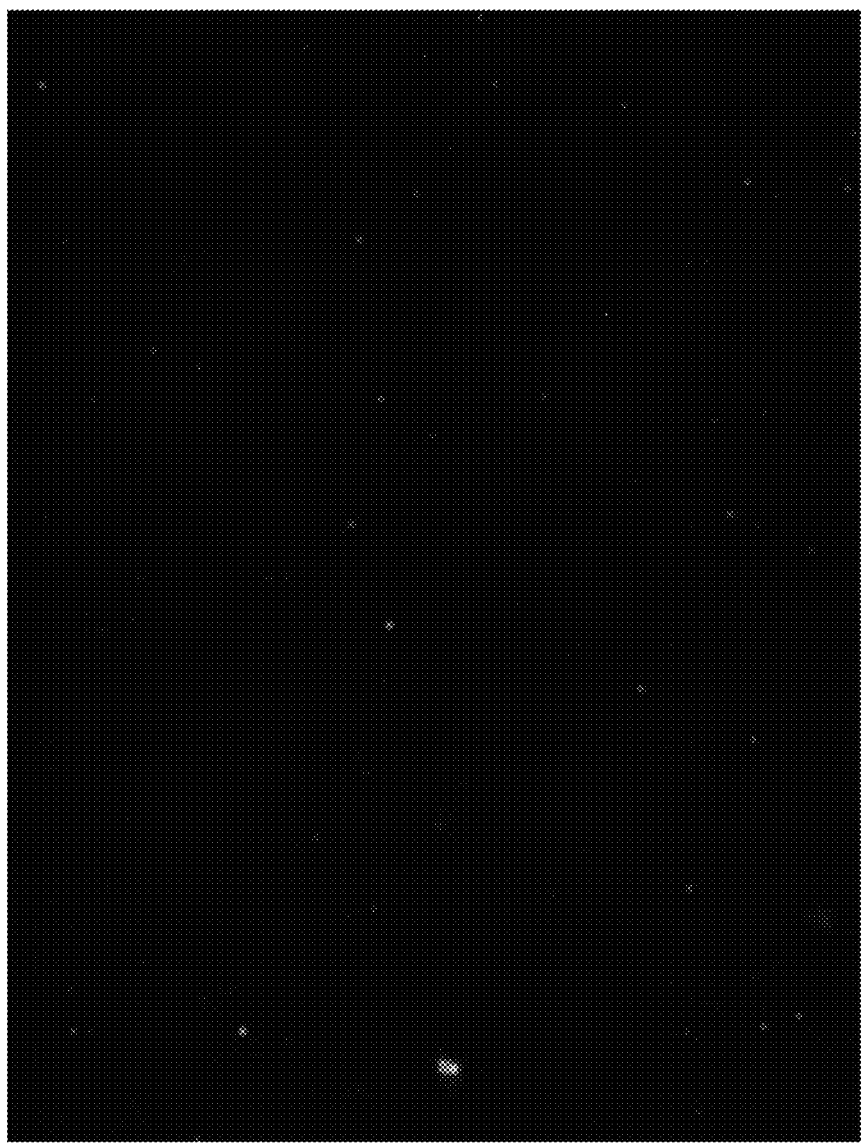
FIG. 7 shows a fluorescent image of minicells packaged with BacLight™ Green. The minicells fluoresce bright green on a black background. BacLight™ Green therefore is shown to be associated with the minicells and not the exterior space.

Fluorescent imaging (FIG. 7) revealed that all of the minicells fluoresced bright green, indicating that BacLight™ Green had been loaded into the minicell. The appearance of a black background, relative to the BacLight™ Green-stained minicells, evidenced little to no exterior stain.

Minicells packaged with BacLight™ Green were analyzed by flow cytometry (Beckman Coulter FC500). Empty minicells and BacLight™ Green-packaged minicells were labeled with an anti-LPS alexa fluor 647 (AF647) antibody. Firstly, the minicells were analyzed using the FL4 channel to detect anti-LPS AF647-stained minicells. The minicell population was visualized in a dot plot using FL4 fluorescence versus forward scatter, and the population was gated to select anti-LPS AF647 stained minicells only, disregarding any debris.

Figure 8:
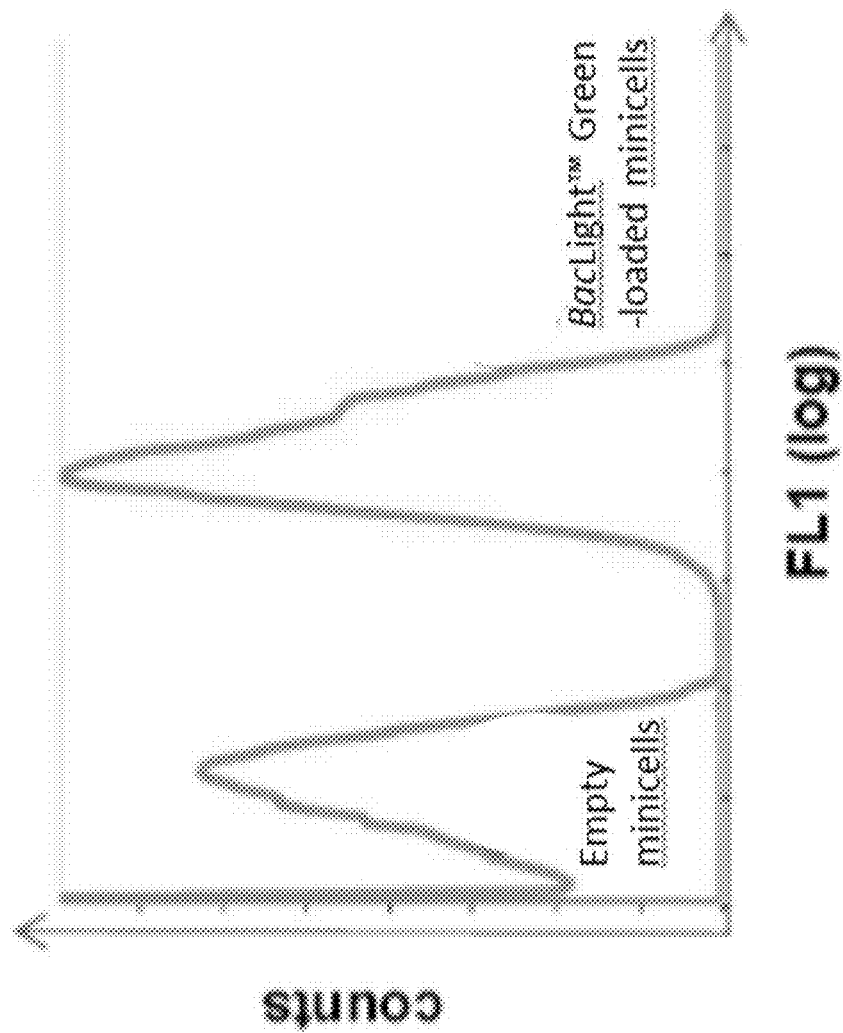
FIG. 8 shows a histogram generated from flow cytometry analysis of empty and BacLight™ Green-packaged minicells. The x axis represents fluorescence in the FL-1 channel, and the y axis=counts. BacLight™ Green-packaged minicells display a distinct population, which is shifted to the right in comparison to the empty minicells, indicating that minicells of the population are fluorescent.

The gated population was analyzed on the FL1 channel, to detect BacLight™ Green fluorescence. The histogram (FIG. 8) represents the BacLight™ Green-packaged minicells as a completely distinct population with a large shift in FL1 fluorescence when compared to empty minicells (log scale). This indicates that greater than 95% of the minicells are fluorescent due to efficient BacLight™ Green incorporation, and that they represent a single fluorescent population with a much greater FL1 fluorescence than that displayed by empty minicells.

Example 6. Loading of Doxorubicin

This example demonstrates that an amphipathic, autofluorescent cytotoxin can be packaged efficiently into the cytoplasm of bacterially derived vesicles. Shown below is the anthracycline structure of the cytotoxin, doxorubicin. Used in cancer chemotherapy, doxorubicin is derived by chemical semisynthesis from *Streptomyces* bacteria and is available commercially.

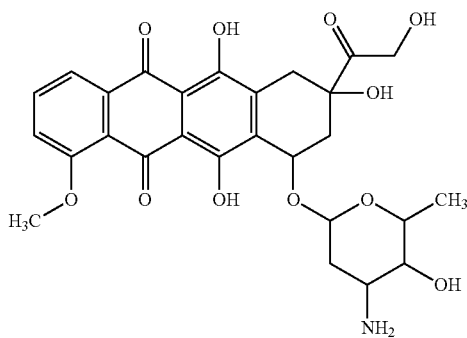 [SMILES: COc1cccc2c1C(=O)c1c(O)c3c(c(O)c1C2=O)CC(O)(C(=O)CO)CC3OC1CC(N)C(O)C(C)O1]

Figure 9:
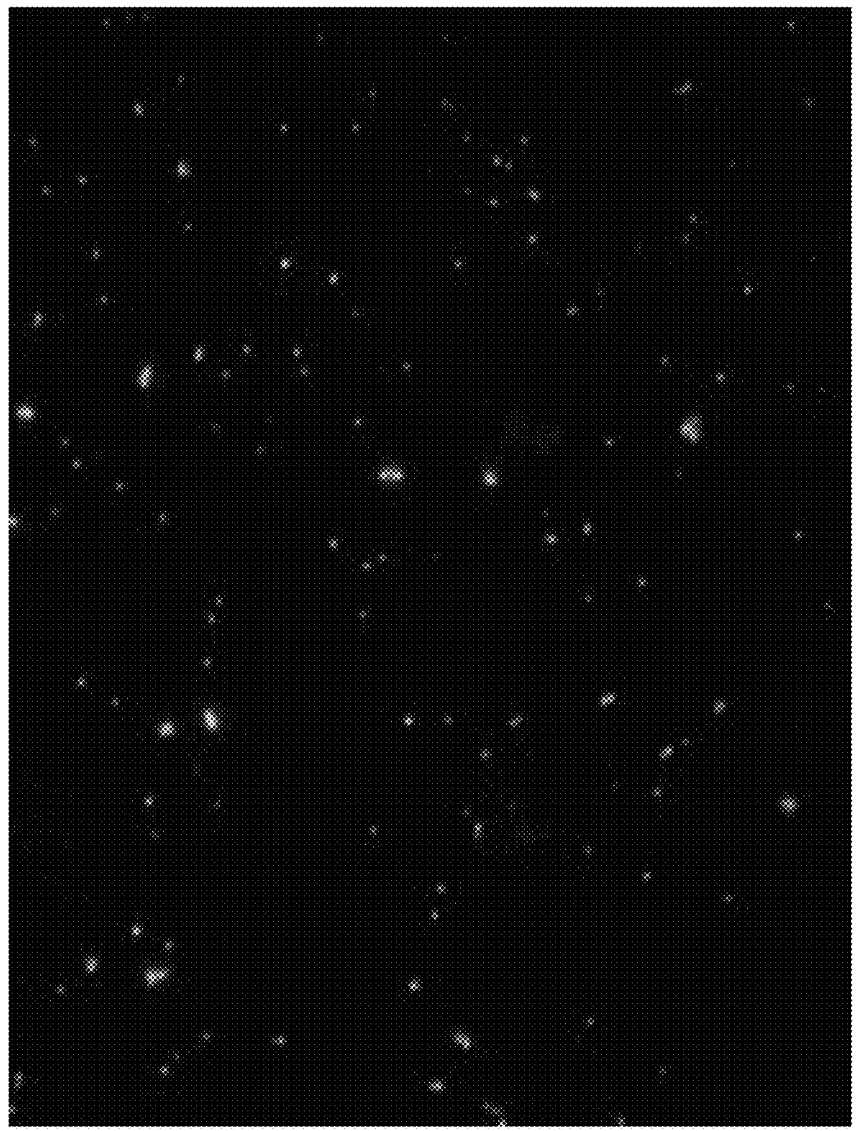
FIG. 9 shows a fluorescent image of minicells packaged with doxorubicin. The minicells fluoresce bright red on a black background, indicating that doxorubicin is present within the minicells rather than in the exterior space.

Pursuant to a large-scale process (loading in small scale plus multiple washing steps in large scale, sans centrifugation, with cross-flow filtration), minicells in PBS buffer were loaded with doxorubicin, and the loaded minicells were visualized via fluorescence microscopy (excitation 480 nm, emission 580 nm; red fluorescence). The imaging results (FIG. 9) revealed that all of the minicells fluoresced bright red, with background that appeared black in comparison to the doxorubicin-packaged minicells.

The quantity of doxorubicin packaged within the minicells was determined by extracting the drug from the minicells, as described, followed by HPLC analysis. The HPLC method characteristics included (i) Mobile phase: 0.1 M ammonium formate pH 3.0: MilliQ $H_2O$: acetonitrile. Gradient 0.2 minutes 28:72:0 to 28:42:30, isocratic 5 minutes, step to 28:72:0, isocratic 15 minutes at flow rate 1.25 ml/minute. (ii) Stationary phase: Waters XBridge Phenyl, 3.5 μm×4.6 mm×150 mm plus C18 cartridge. (iii) Column temperature: 40° C. (iv) Detection: Fluorescence—Excitation 480 nm, Emission 560 nm. (v) Injection volume: 10 μl. (vi) HPLC system: A Shimadzu 10AVP system comprising autosampler, solvent degasser, quaternary pump, column heater and fluorescence detector with Class-VP version 7.2.1 software (Shimadzu corporation, Kyoto, Japan).

Figure 10:
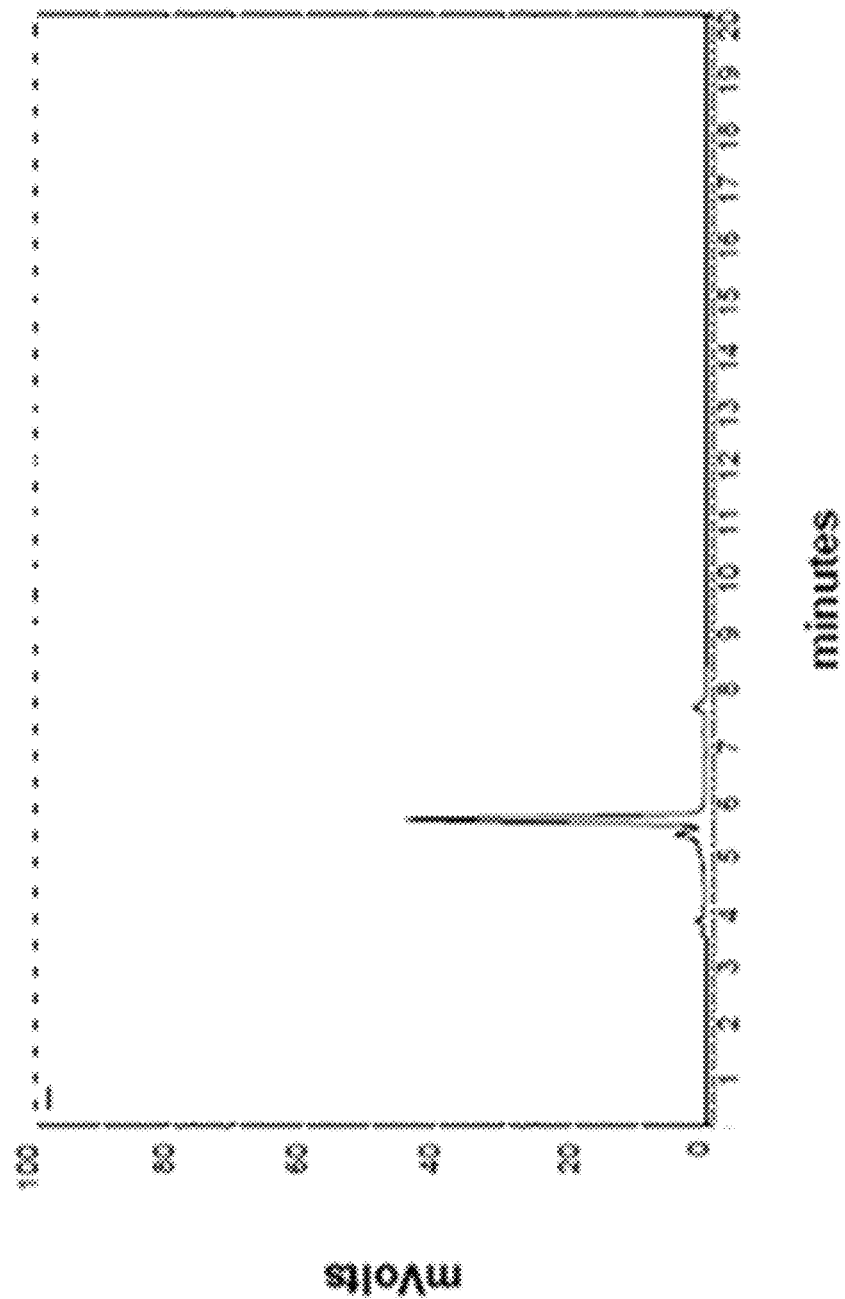
FIG. 10 shows an example chromatogram from an HPLC separation of an extract from $1\times10^9$ doxorubicin-packaged minicells. The peak corresponding to doxorubicin is found at the retention time $(r_t)$=5.5 minutes. The area of this peak was used to calculate the quantity of doxorubicin packaged into the minicells by comparing to a standard curve of known doxorubicin quantities.

The content of doxorubicin obtained with these drug-loading conditions was determined with HPLC to be approximately 770 ng per $1 \times 10^9$ minicells, by comparison to a linear standard curve of doxorubicin samples of known quantity (FIG. 10). This equates to about 800,000 molecules of doxorubicin loaded into each minicell.

Example 7. Loading of a Fluorescent Nucleic Acid Stain

SYTO® 9 is a nucleic acid-binding bacterial stain that is green-fluorescent (excitation ~485/6 nm, emission ~498/501 nm). For this example it was obtained from Life Technologies (Thermo Fisher Scientific), Molecular Probes® brand.

SYTO® 9 solution was added to minicells in PBS buffer to a final concentration of 20 μM. Pursuant to the small-scale protocol, the minicells were incubated for 30 minutes and were subject to a thrice-repeated washing step, as described previously.

Figure 11:
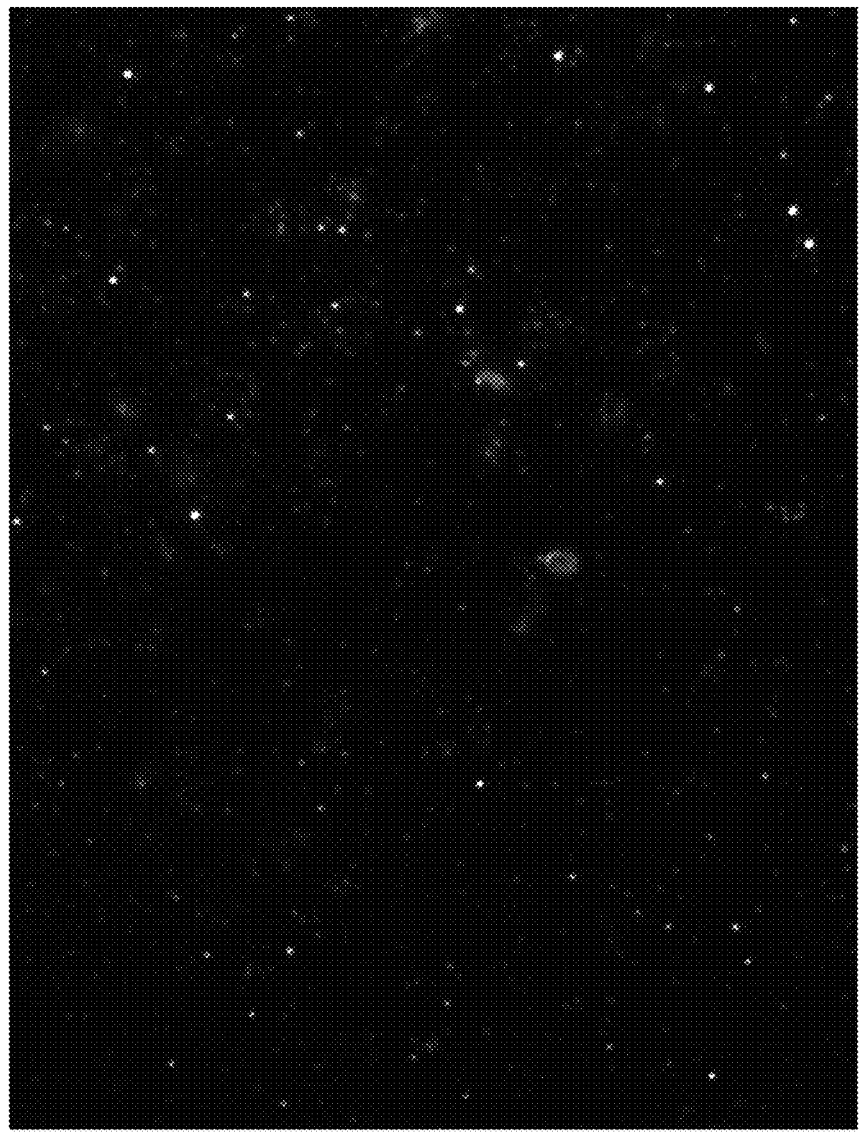
FIG. 11 shows a fluorescent image of minicells packaged with the nucleic acid dye SYTO 9. The minicells fluoresce bright green on a black background indicating that SYTO 9 is associated with the minicells, not the exterior space.

SYTO® 9 Green-packaged minicells were visualized using a fluorescence microscope, as described above, with the appropriate filter employed to permit visualization of SYTO® 9 fluorescence. Fluorescent imaging (FIG. 11) revealed that the SYTO® 9 had been incorporated into the minicells, with little to no exterior stain.

Minicells loaded with SYTO 9® were analyzed by flow cytometry (Beckman Coulter FC500). Empty minicells and SYTO® 9-stained minicells were labeled with an anti-LPS alexa fluor 647 (AF647) antibody. Firstly, the minicells were analyzed using the FL4 channel to detect anti-LPS AF647-stained minicells. The minicell population was visualized in a dot plot, using FL4 fluorescence versus forward scatter, and the population was gated to select anti-LPS AF647-stained minicells only, disregarding any debris. The gated population then was analyzed on the FL1 channel, to detect SYTO 9 fluorescence.

Figure 12:
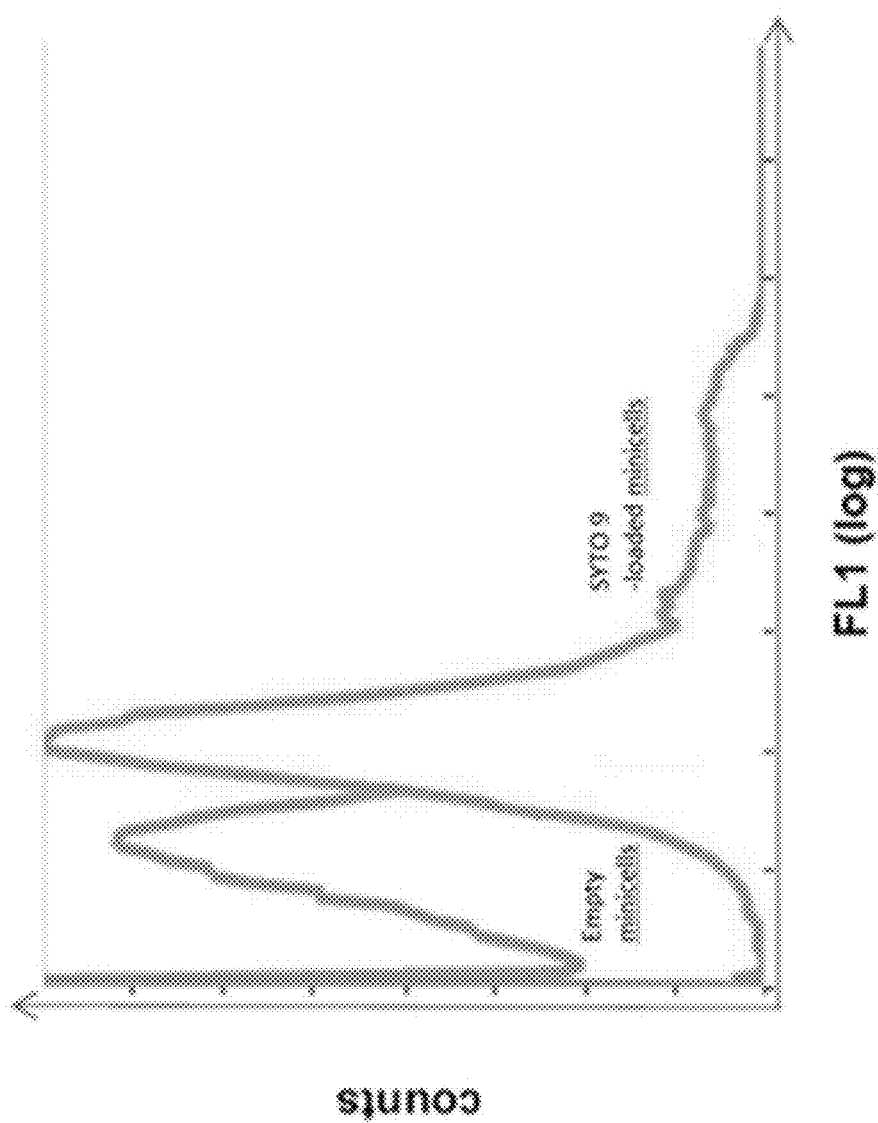
FIG. 12 shows histogram generated from flow cytometry analysis of empty and SYTO 9-packaged minicells. The x axis represents fluorescence in the FL-1 channel; the y axis=counts. SYTO 9-packaged minicells display a distinct population, which is shifted to the right in comparison to the empty minicells; thus, the packaged minicells are fluorescent.

The histogram thus obtained (FIG. 12) represents the SYTO 9-stained minicells as a distinct population, with a shift in FL1 fluorescence when compared to empty minicells (log scale). This indicates that the minicells are fluorescent due to SYTO 9 incorporation and that they represent a fluorescent population with a greater FL1 fluorescence than is shown by empty minicells.

Example 8. Loading of 9-Aminoacridine Compound

This example demonstrates that the fluorescent dye 9-aminoacridine, as a hydrochloride hydrate compound, can be packaged into the cytoplasm of intact, bacterially derived vesicles. The compound, 9-aminoacridine hydrochloride hydrate (9-AAHH), is available from Sigma-Aldrich (St. Louis, Mo.) and has the structure shown below.

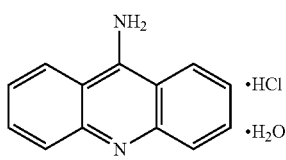

Figure 13:
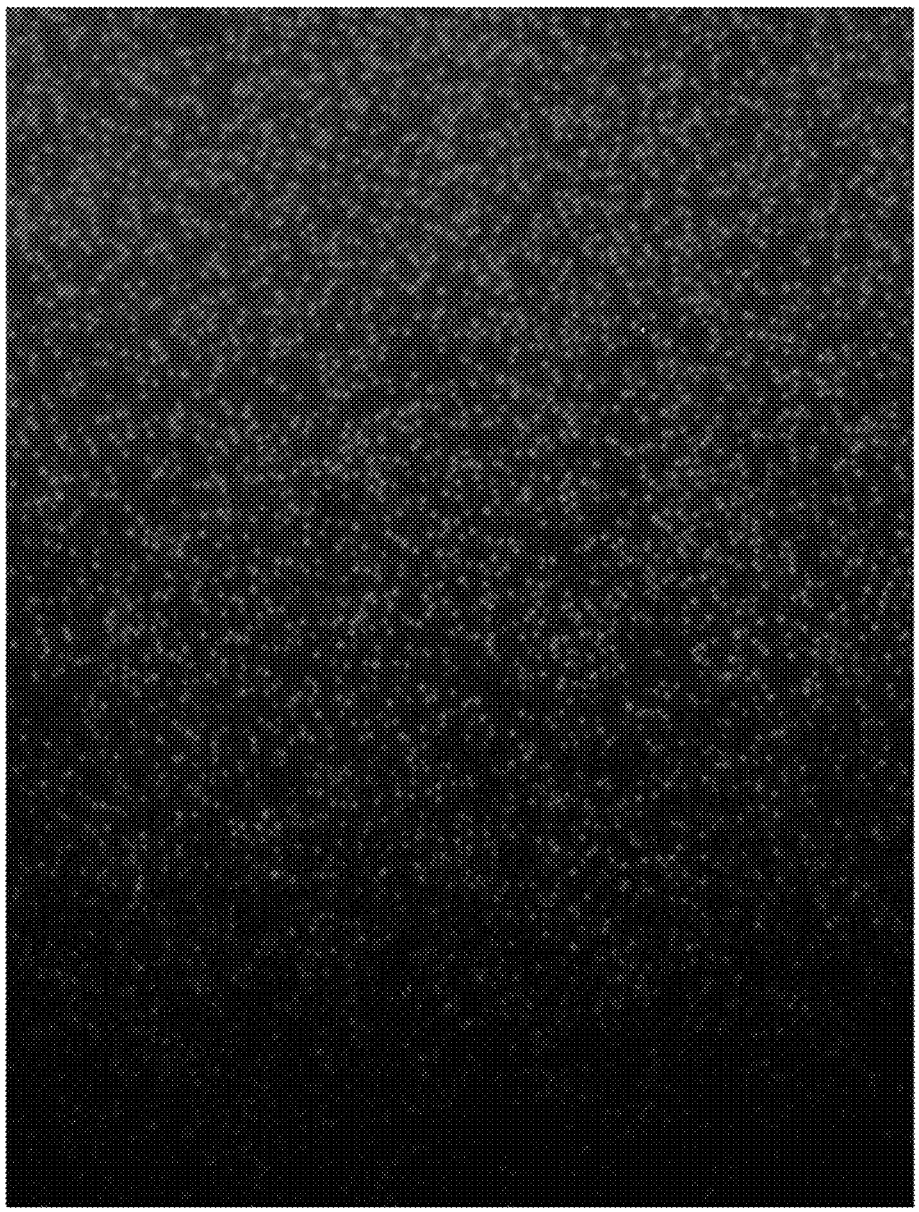
FIG. 13 shows a fluorescent image of minicells packaged with 9-aminoacridine hydrochloride hydrate. The minicells fluoresce blue on a dark background indicating that 9-aminoacridine hydrochloride hydrate is associated with the minicells instead of the exterior space.

Minicells in PBS ($2.5\times10^{10}$) loaded with 9-AAHH (incubation solution: 500 µg/ml) were prepared via the small-scale protocol and were subjected to fluorescence-microscopic visualization (excitation 400 nm, emission 420 nm; blue fluorescence). Fluorescent imaging results (FIG. 13) indicated that 9-aminoacridine had been transferred into the minicell cytoplasm and had remained there, despite reversal of the concentration gradient throughout the washing steps.

Example 9. Inefficient Loading of Paclitaxel

This example demonstrates that the hydrophobic, non-fluorescent cytotoxic drug paclitaxel (see structure below) is loaded into the cytoplasm of intact, bacterially derived vesicles less efficiently than are fluorescent derivatives of paclitaxel.

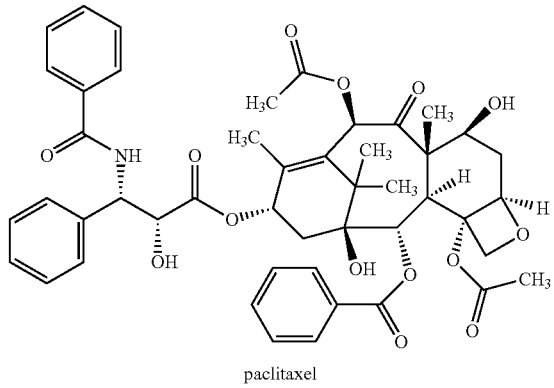

paclitaxel

Minicells in PBS buffer were prepared according to the small-scale protocol. Thus, empty minicells (free endotoxin level $\leq\sim 2$ EU per $10^9$ minicells) were added to a microfuge tube and centrifuged (16,000 g, 10 minutes). The supernatant was discarded and the minicell pellet was thoroughly resuspended in 0.9 ml of PBS buffer adjusted to pH 3 (the lower pH was necessary to keep the highly hydrophobic paclitaxel in solution for at least 30 minutes). Ten to the minicell suspension were added 100 µl of 6 mg/ml paclitaxel (in 1:1 cremophor EL:EtOH), yielding an external paclitaxel concentration of 600 µg/ml. The minicells were incubated at 37° C. overnight with rotation. Excess paclitaxel solution and molecules attached non-specifically to minicell surfaces were washed by centrifugal washes. That is, post-incubation minicells were centrifuged (16,000 g, 10 minutes) and the paclitaxel loading supernatant was discarded. The paclitaxel-loaded minicells were washed by thoroughly, resuspending the pellet in 1 ml of PBS (pH 7.4), centrifuging the minicells (16,000 g, 10 minutes), and discarding the supernatant wash. The wash step was repeated three times. Finally, the paclitaxel-loaded minicells were resuspended in PBS (pH 7.4).

The quantity of paclitaxel packaged within the minicells was determined as above, using HPLC analysis. A HPLC method developed for paclitaxel quantification had characteristics that included (i) Mobile phase: acetonitrile and MilliQ $dH_2O$, isocratic 0.24 minutes 37:63, gradient elution for 5 minutes from 37:63 to 60:40 then mobile phase returned to original solvent composition 37:63 over 1 minute and maintained at this level to the end at a flow rate of 2 ml/minute (running time 8 minutes); (ii) Stationary phase: Metalchem 3u Taxsil, 100 mm×4.6 mm plus C18 cartridge; (iii) Column temperature: 40° C.; (iv) Detection: SPD-M10Avp, diode array detector-228 nm; (v) Injection volume: 50 µl; and (vi) HPLC system: a Shimadzu SCL-10AVP system comprising SIL-10AVP auto-injector, LC-1Advp pump, DGU-14A degasser, CTO-10Avp column oven, SPD-M10Avp diode array detector with Class-VP version 7.2.1 software (Shimadzu Corp., Kyoto, Japan).

Figure 14:
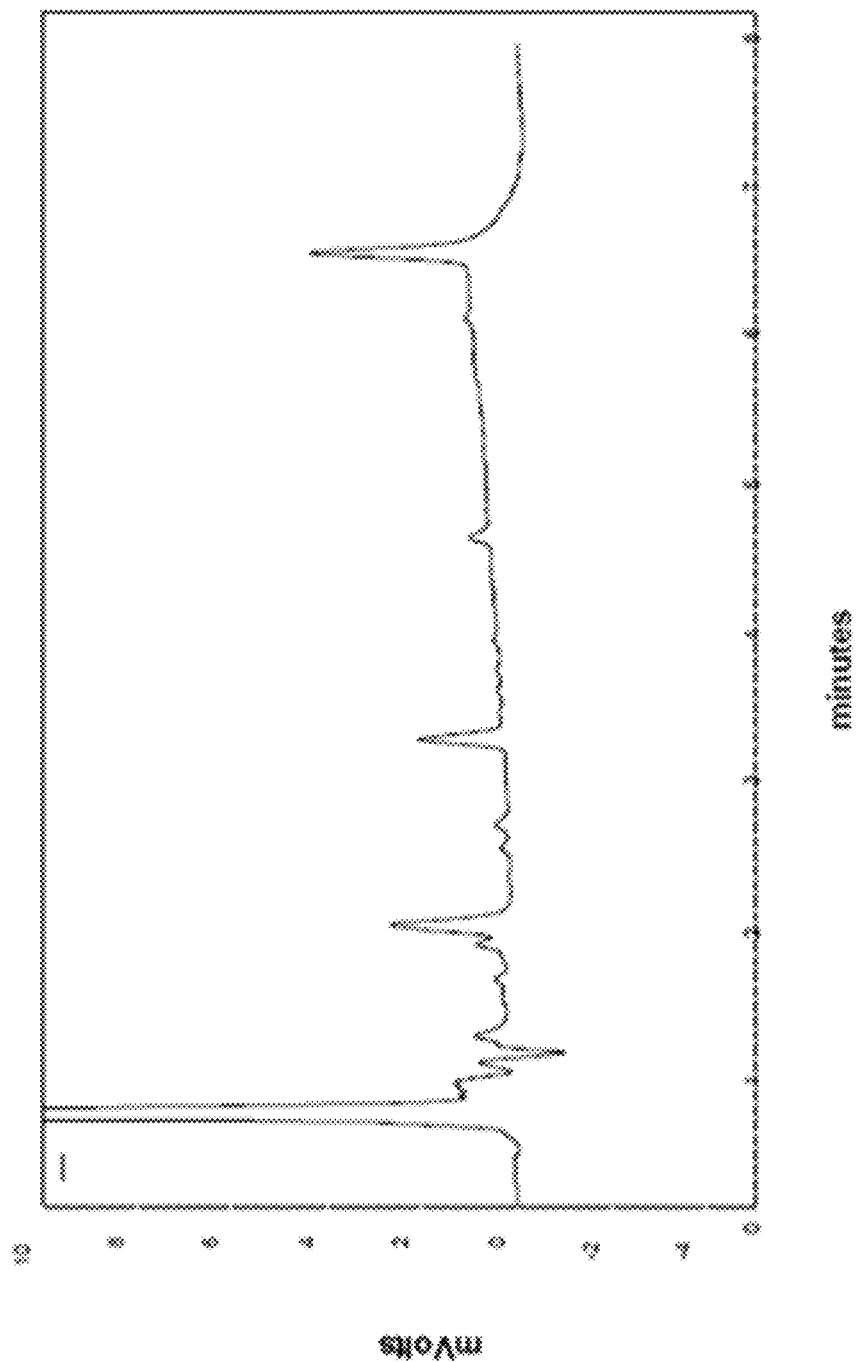
FIG. 14 shows an example chromatogram from an HPLC separation of an extract from $1\times10^9$ paclitaxel-packaged minicells. The peak corresponding to paclitaxel is found at the retention time $(r_t)$=4.48 minutes. The area of this peak was used to calculate the quantity of paclitaxel packaged into the minicells by comparing to a standard curve of known quantities.

The paclitaxel content obtained with these drug loading conditions was quantified by HPLC as 3 ng per $1\times10^9$ minicells, by comparison to a linear standard curve of paclitaxel samples of known quantity (FIG. 14). This equates to 2115 molecules of Paclitaxel encapsulated per minicell, or approximately 110-130-fold fewer than for FCP and FLUTAX-1, respectively. Additional approaches were employed in an attempt to load the minicells with greater quantities of paclitaxel. These included varying solvents, buffers, pH, use of cyclodextrin/Paclitaxel inclusion complexes, use of hydrotropes such as sodium salicylate and NN-diethylnicotinamide, and the use of membrane-destabilization methods, chemical (e.g., EDTA, $CaCl_2$ treatment) and physical (such as sonoporation). All of the tested approaches yielded similar results, with paclitaxel-loading efficiency in the range of 0-10 ng per $1\times10^9$ minicells.

Example 10. Loading of a Water-Soluble Paclitaxel Analog

This example demonstrates that the loading efficiency of 2'-β-alanyl taxol formate or "TF.Pac" (see structure below), a water-soluble analog of paclitaxel, was only slightly increased compared to paclitaxel itself.

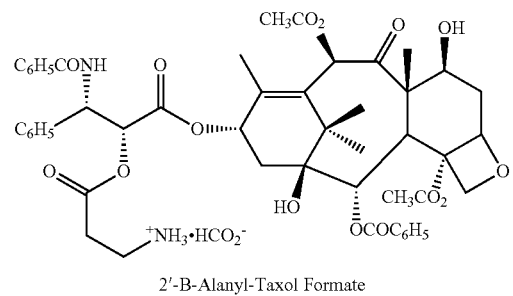

2'-B-Alanyl-Taxol Formate

TF.Pac has improved solubility due to a beta-alanyl formate salt conjugated to the C2' of paclitaxel. Not available commercially, TF.Pac was synthesized in order to illuminate whether it is simply poor aqueous solubility that inhibits efficient loading of paclitaxel into intact, bacterially derived vesicles. Paclitaxel is soluble in water to 0.3 µg/ml while the solubility of TF.Pac is at least 2 mg/ml.

Minicells in PBS buffer were loaded with TF.Pac (loading solution: 1 mg of compound per ml of distilled water 0.1% acetic acid) pursuant to the small-scale protocol.

The quantity of TF.Pac thus packaged within the minicells was determined by extracting the drug from the minicells followed by HPLC analysis. Minicell extraction was performed as described above for minicells packaged with doxorubicin. The HPLC method used was identical to that developed for paclitaxel quantification.

Figure 15:
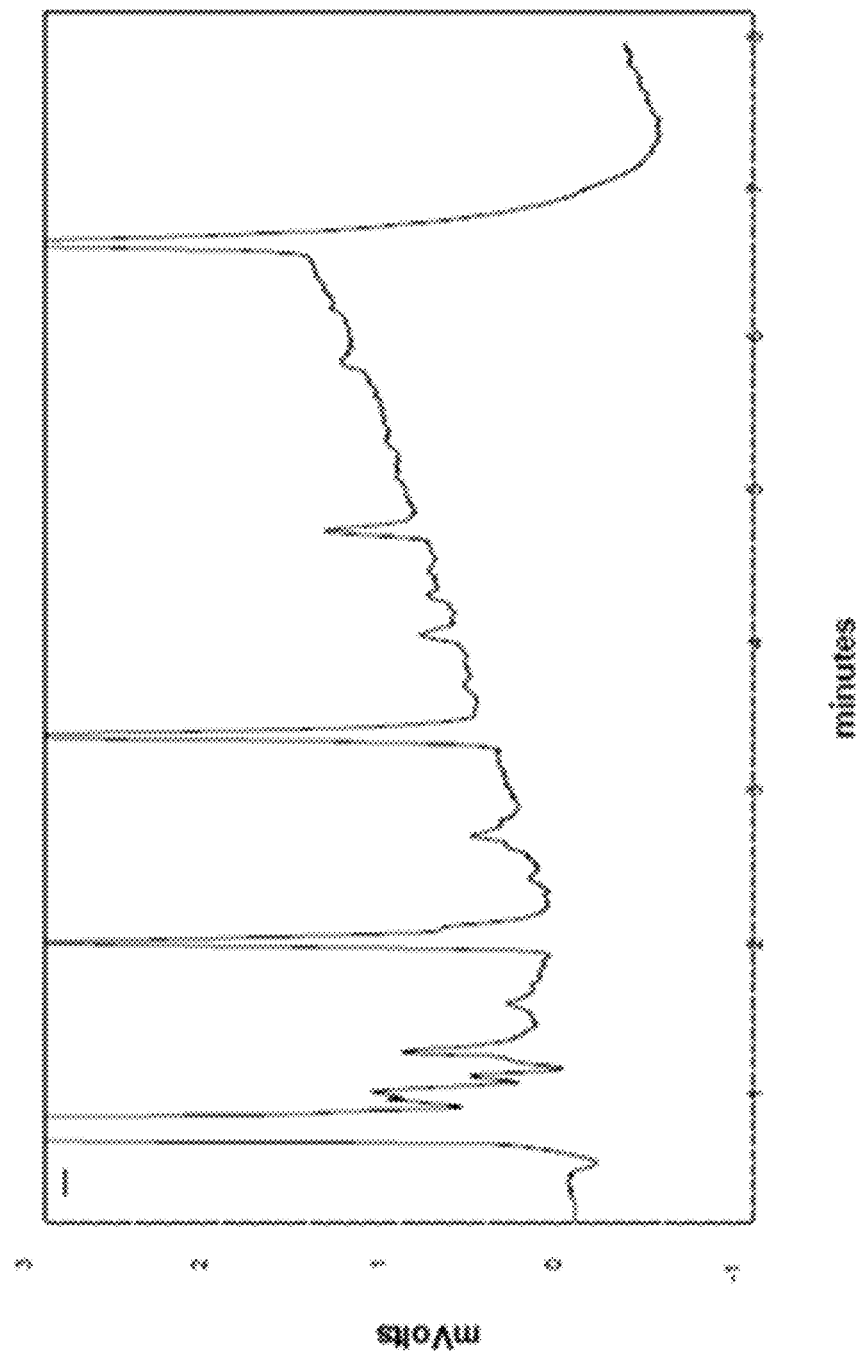
FIG. 15 shows an example chromatogram from an HPLC separation of an extract from $1\times10^9$ TF.Pac-packaged minicells. The peak corresponding to TF.Pac is found at the retention time $(r_t)$=4.57 minutes. The area of this peak was used to determine the quantity of TF.Pac packaged into the minicells by comparing to a standard curve of known TF.Pac quantities.

The average TF.Pac content obtained with these drug loading conditions was quantified by HPLC as 78 ng per $1 \times 10^9$ minicells (FIG. 15), which equates to ~50,000 molecules of TF.Pac packaged per minicell. The loading efficiency thus was somewhat greater than for paclitaxel but was ~5.4-fold less than for FLUTAX-1. Numerous buffers were employed in an attempt to load minicells with greater quantities of TF.Pac; however, the efficiency obtained with the method described above was not exceeded. Accordingly, merely increasing aqueous solubility of a chemical compound is not a driver of enhanced loading into intact, bacterially derived vesicles.

Example 11. Doxorubicin Fluorescence Quencher Folic Acid Influences Loading of Doxorubicin into Intact Minicells This example determines whether a fluorescent compound loads less effectively into intact, bacterially derived vesicles when its fluorescence is quenched. In this instance the compound was the autofluorescent drug doxorubicin (Dox) and the quencher was folic acid (FA). See Husseini, Adv. Sci. Lett. 7: 726 (2012) (FA quenches Dox fluorescence).

Materials and Methods

Doxorubicin in PBS (100 µg/ml) was mixed with various concentrations of FA, namely, 0 µg/ml, 50 µg/ml, and 400 µg/ml. The solutions were incubated at room temperature overnight and then were filtered through a 0.1 µm filter, to sterilize the solutions and to remove any particulates.

On the following day the fluorescence of an aliquot of each solution was measured with a fluorescence plate reader (excitation wavelength: 485 nm, emission wavelengths: 590 nm and 620 nm). Concomitantly, minicells were washed with PBS buffer and then were loaded with one or another of each of the Dox+FA solutions, previously prepared at a density of $2.5 \times 10^{10}$ minicells/ml, in a volume between about 1 ml to 2 mls. Samples (500 µl) were taken from each of the treatment groups at the time points of 30 minutes, 1 hour, 2 hours, 4 hours, 6 hours, and overnight.

For each time point the minicells were subjected to the following small-scale protocol:
1. Centrifuged minicells—16,000 g for 7 minutes.
2. Discarded supernatant (SN) and resuspended pellet in 1 ml of PBS buffer (pH 7.4).
3. Centrifuged minicells—16,000 g for 7 minutes.
4. Discarded SN and resuspended pellet in 0.5 ml of PBS buffer.
5. Passed minicell suspension through a 0.8 µm filter.
6. Washed the filter with a further 0.5 ml of PBS and combined with minicells.
7. Centrifuged minicells—16,000 g for 7 minutes.
8. Discarded SN and resuspended pellet in 1 ml of PBS buffer.
9. Centrifuged minicells—16,000 g for 7 minutes.
10. Discarded SN and resuspended pellet in 1 ml of PBS buffer.
11. Centrifuged minicells—16,000 g for 7 minutes.
12. Discarded SN and finally resuspended pellet in 350 µl of PBS buffer.
    a. 20 µl minicells aliquotted for minicell quantitation using Nanosight technology for nanoparticle tracking analysis (Malvern Instruments, UK).
    b. 40 µl of minicells pelleted for extraction and HPLC analysis (15 minutes at 16,000 g, SN discarded and pellet stored at −20° C.).

Doxorubicin-loaded minicells appeared pink-red as a centrifuged pellet. On the basis of relative color intensity, assessed through ocular inspection, it was apparent that minicells loaded in the presence of 400 µg/ml folic acid contained significantly less doxorubicin than those loaded in the absence of folic acid, after completion of the washing steps at each of the time points.

Somewhat less loading was observed as well in the 50 µg/ml-folic acid samples, compared to 0 µg/ml folic acid.

TABLE 2

Results of fluorescence readings of doxorubicin loading solutions

| µg/ml FA | % Fluorescence Em λ590 nm | Em λ620 nm |
|---|---|---|
| 0 | 100% | 100% |
| 50 | 93% | 94% |
| 400 | 61% | 59% |

Figure 16:
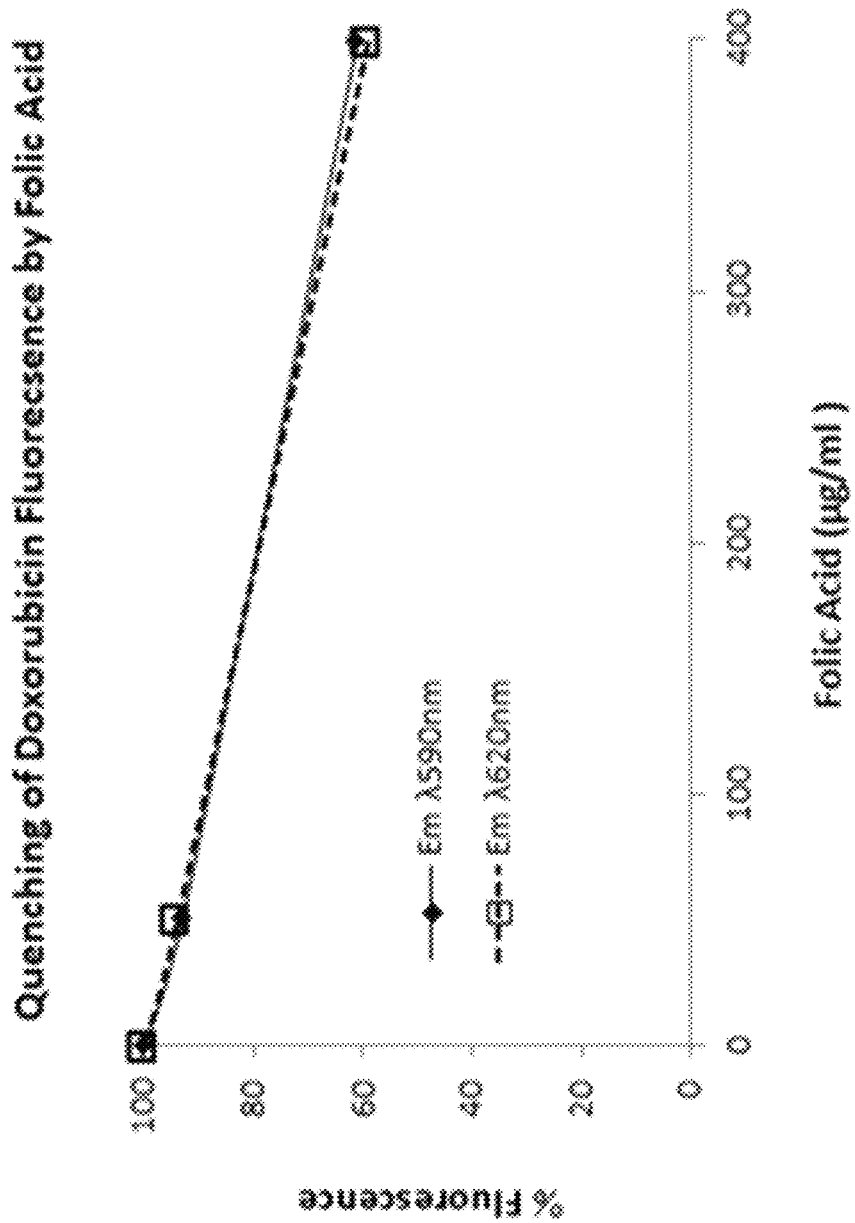
FIG. 16 shows the fluorescence readings, at two different wavelengths, of doxorubicin loading solutions with different concentrations of folic acid.

It was observed that 50 µg/ml and 400 µg/ml folic acid quenched the fluorescence of 100 µg/ml Dox solutions to varying degrees (FIG. 16). This held true when the solution was excited at 485 nm and the emission was measured at either 590 nm or 620 nm. Doxorubicin quenching was more evident using 400 µg/ml of folic acid, with ~40% of the doxorubicin fluorescence emission signal lost, while only 6-7% of the doxorubicin emission fluorescence was lost using the lower concentration of 50 µg/ml folic acid.

Quantitation of Minicell$_{DOX}$ Samples by Colorimery

In addition to using HPLC to determine Dox content for each of the minicell samples, a colorimetric assay was employed to measure doxorubicin content, since this measure is independent of Dox fluorescence.

Doxorubicin Standard Curve

A standard curve of free doxorubicin was generated. Absorbance of doxorubicin in PBS, at various concentrations in duplicate, was measured via biophotometer at 490 nm.

Results

Figure 17:
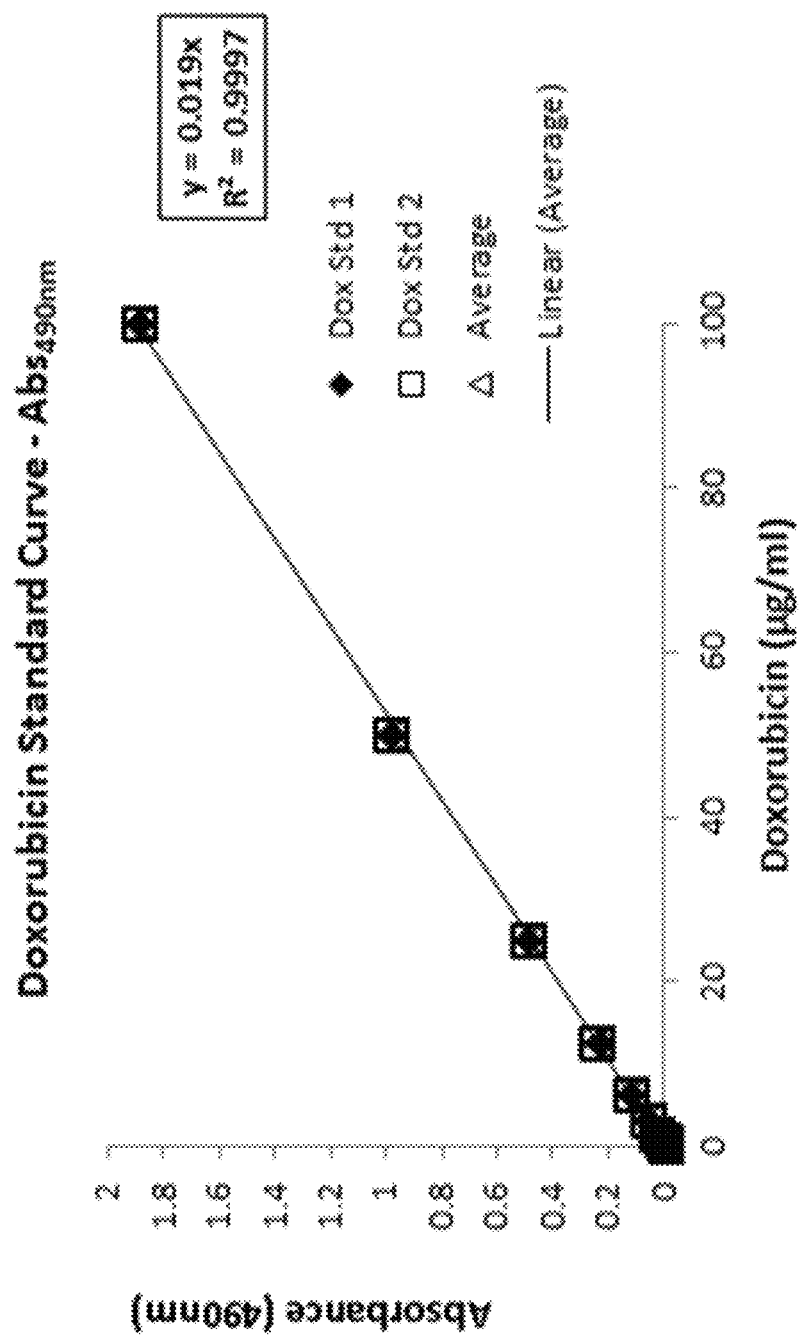
FIG. 17 shows the generation of a standard curve of free doxorubicin.

A linear regression was performed on the averaged data, which generated the equation y=0.019x, where y is absorbance (Abs$_{490nm}$) and x is µg/ml of doxorubicin (FIG. 17). For the minicell$_{Dox}$ samples measured, therefore, $$\mu g/ml\ doxorubicin = Abs_{490nm}/0.019$$

Colorimetry of Minicell$_{Dox}$ Samples

Minicells from each minicell$_{Dox}$ sample were made up to 200 µl with PBS buffer (pH7.4) in cuvettes, per the table above. A 'blank' sample containing empty minicells also was made up in 200 µl of PBS (pH7.4) in a cuvette. The absorbance of the blank minicell sample and all of the minicell$_{Dox}$ samples was measured at 490 nm.

TABLE 3

Results of colorimetric assay of minicell$_{Dox}$ samples

| Sample | | Abs490 | minus blank | µg/ml Dox | ng of Dox per $10^9$ EDVs |
|---|---|---|---|---|---|
| empty EDVs (blank) | | 0.472 | n/a | n/a | n/a |
| 30 mins | 0FA | 0.596 | 0.124 | 6.5 | 435 |
| | 50FA | 0.533 | 0.061 | 3.2 | 214 |
| | 400FA | 0.476 | 0.004 | 0.2 | 14 |

TABLE 3-continued

Results of colorimetric assay of minicell$_{Dox}$ samples

| Sample | | Abs490 | minus blank | μg/ml Dox | ng of Dox per 10$^9$ EDVs |
|---|---|---|---|---|---|
| 1 hr | 0FA | 0.525 | 0.053 | 2.8 | 186 |
| | 50FA | 0.529 | 0.057 | 3.0 | 200 |
| | 400FA | 0.447 | −0.025 | −1.3 | −88 |
| 2 hrs | 0FA | 0.576 | 0.104 | 5.5 | 365 |
| | 50FA | 0.649 | 0.177 | 9.3 | 621 |
| | 400FA | 0.588 | 0.116 | 6.1 | 407 |
| 4 hrs | 0FA | 0.641 | 0.169 | 8.9 | 593 |
| | 50FA | 0.592 | 0.12 | 6.3 | 421 |
| | 400FA | 0.5 | 0.028 | 1.5 | 98 |
| 6 hrs | 0FA | 0.554 | 0.082 | 4.3 | 288 |
| | 50FA | 0.548 | 0.076 | 4.0 | 267 |
| | 400FA | 0.499 | 0.027 | 1.4 | 95 |
| overnight | 0FA | 0.735 | 0.263 | 13.8 | 923 |
| | 50FA | 0.68 | 0.208 | 10.9 | 730 |
| | 400FA | 0.567 | 0.095 | 5.0 | 333 |

Figure 18:
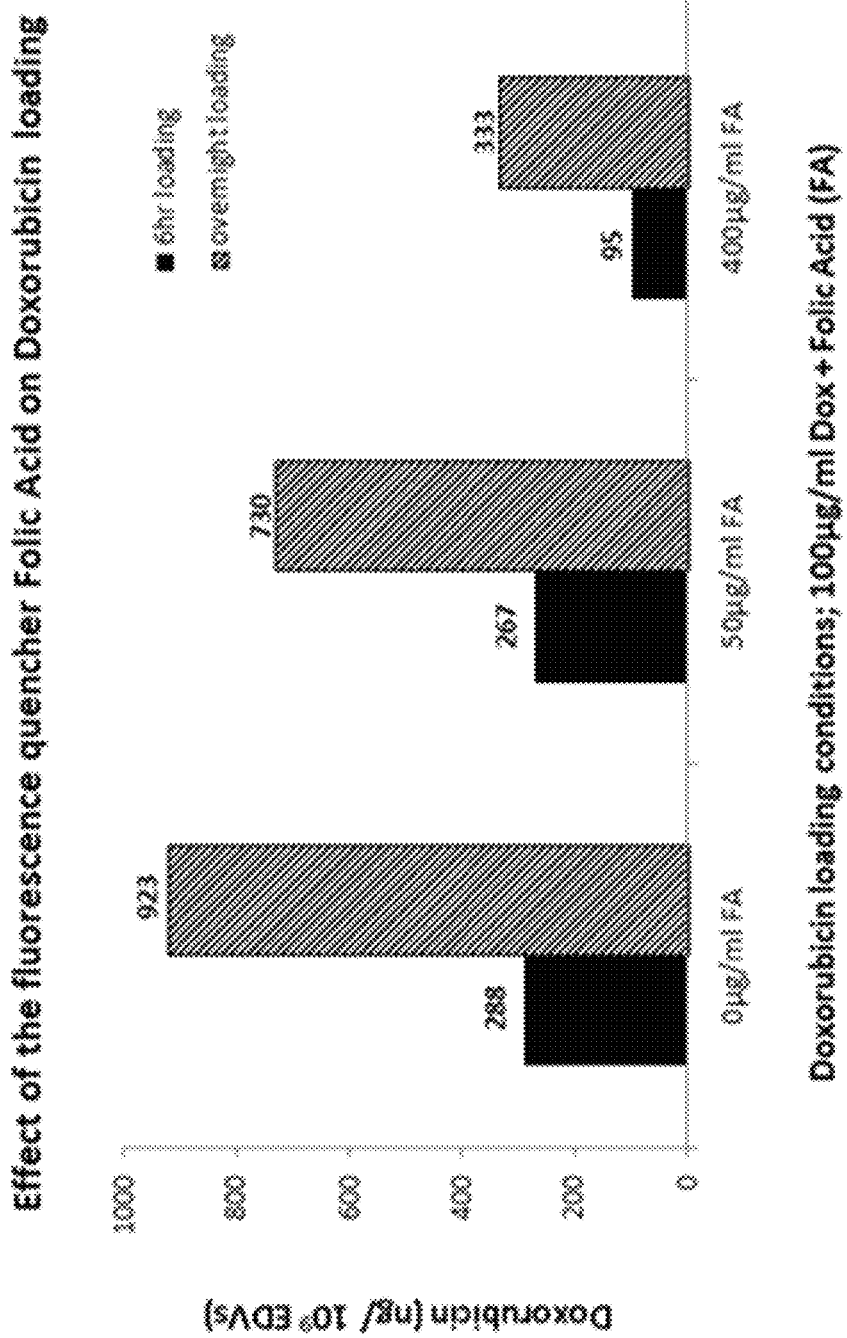
FIG. 18 shows the effect of fluorescence quencher folic acid on doxorubicin loading.

The results are presented in Table 3, above. Most samples were too close to the blank absorbance of 0.472 (i.e., they were within the biophotometer error of 0.1) to be useful. The sensitivity of this colorimetric assay was too low for the majority of samples, and the measurements from most time points therefore fluctuated. See FIG. 18.

HPLC Results

The minicell pellets were processed for analysis by HPLC as described by MacDiarmid et al. (2007), supra. Dox in each sample was quantitated using both $UV_{250nm}$ detection and relative fluorescence (RF) detection.

Figure 19:
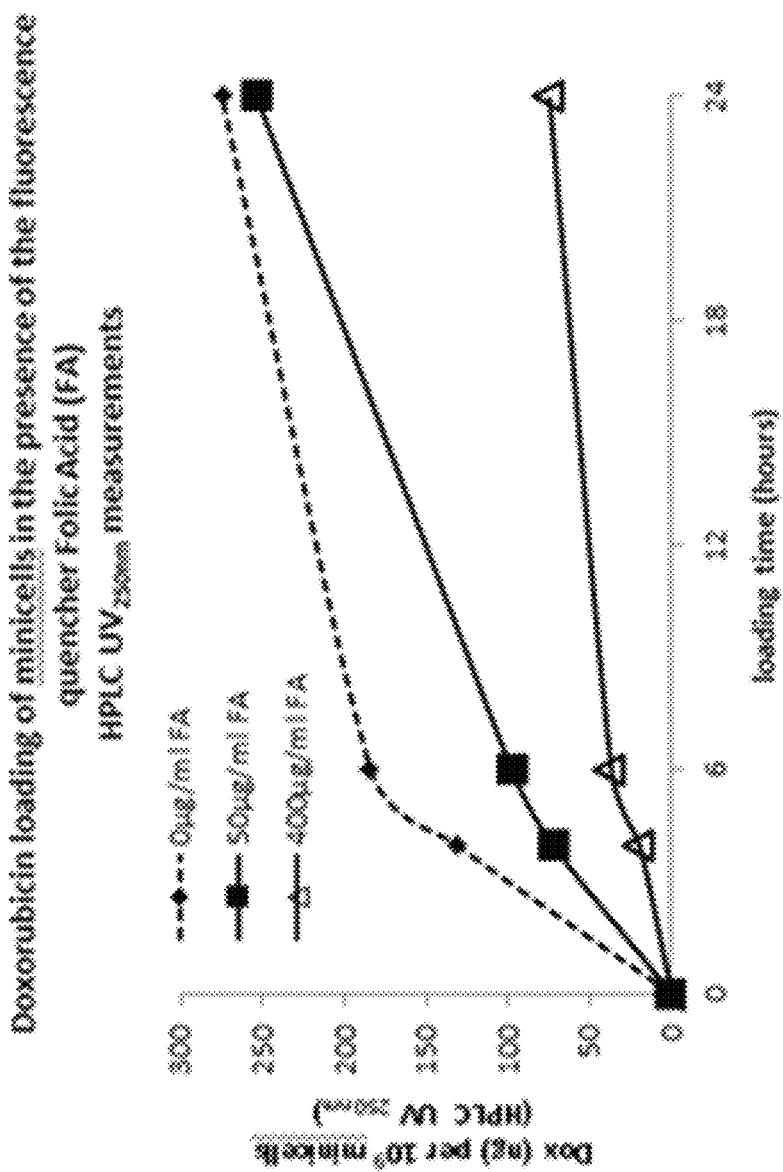
FIG. 19 shows the HPLC quantification of doxorubicin loading into minicells from UV (250 nm) readings.
Figure 20:
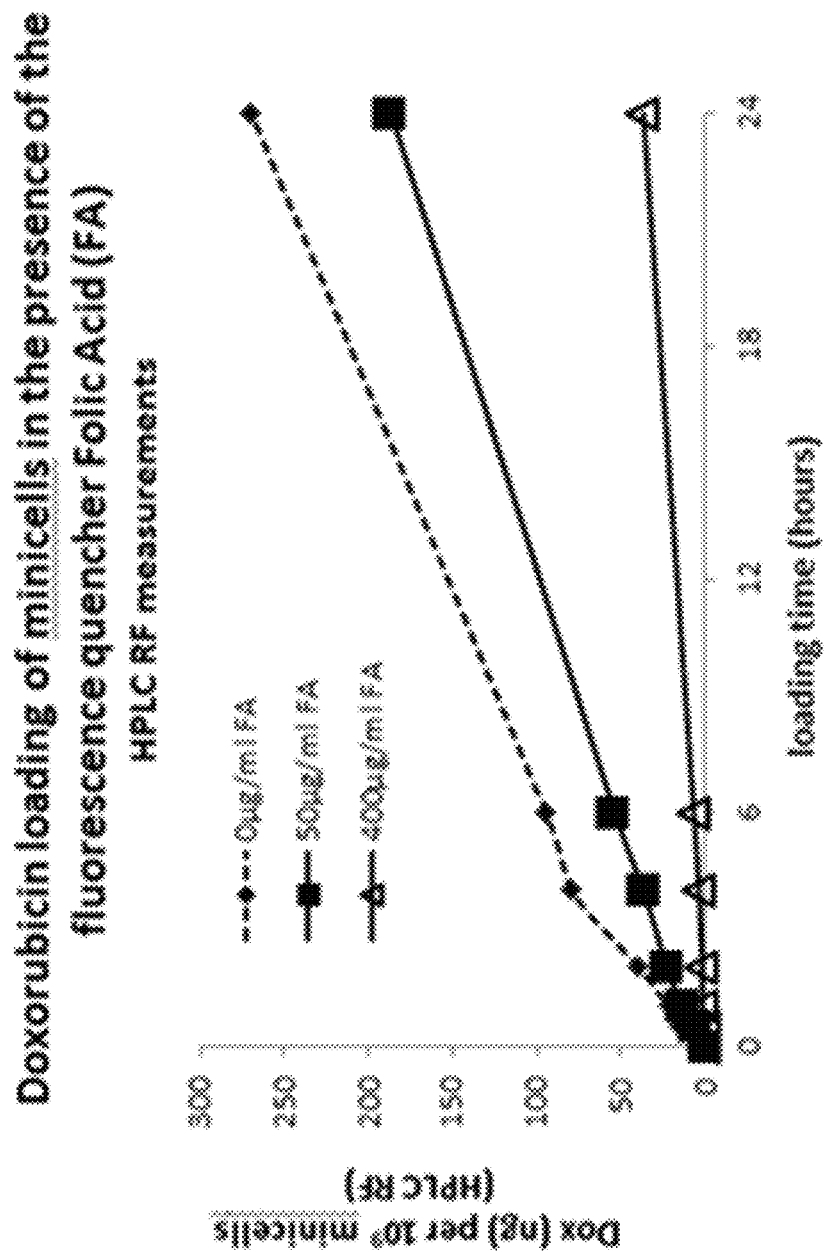
FIG. 20 shows the HPLC quantification of doxorubicin loading from relative fluorescence (RF) readings.

The HPLC quantification from $UV_{250nm}$ readings are presented in FIG. 19, and HPLC quantification from relative fluorescence (RF) readings are shown in FIG. 20. The increasing amounts of folic acid present in the loading solution were observed to affect adversely the loading of doxorubicin into minicells. The higher the external concentration of folic acid, the lower was the concentration of doxorubicin loaded into intact minicells.

Example 12. Loading of Mitoxantrone

This example illustrates enhanced loading into intact, bacterially derived vesicles of mitoxantrone dihydrochloride (MTX), an intrinsically fluorescent cytotoxic drug also known as "Mitozantrone." An anthracenedione anti-neoplastic agent, MTX acts as a type II topoisomerase inhibitor and has been used to treat cancers such as metastatic breast cancer, acute myeloid leukemia, and non-Hodgkin's lymphoma.

Mitoxantrone was purchased from Sigma-Aldrich (St. Louis, Mo.). Empty, intact minicells were prepared (3.2× 10$^{10}$/ml) as described above. Centricon® columns (0.65 μm) were obtained from Millipore (Billerica, Mass.), sterile PBS (pH 7.4) from Sigma-Aldrich, and injectable saline from Livingstone Int'l (Rosebery, NSW).

A 2 mg/ml stock solution of MTX was prepared in saline and was filtered through a 0.1 μm filter. (Mitoxantmone is soluble in water to approximately 5-7.5 mg/ml.) The resultant solution was stored at 4° C. and protected from light.

The small-scale protocol was adapted for use in this example. Thus, in separate tubes minicells were provided in 781 μl aliquots (2.5×10$^{10}$ final). The tubes were spun at 13,200 rpm for 8 minutes on a benchtop Eppendorf centrifuge. The supernatant was removed; pellets were resuspended in 1 ml of PBS buffer (pH 7.4) and then were spun again. The pellets thus obtained were resuspended in 850 μl of PBS buffer.

A volume (150 μl) of MTX (2 mg/ml stock) was added to each minicell suspension to give a final loading solution of 300 μg/ml (external concentration). With mixing on a rotator, the samples were incubated at 37° C. for 2 hours, for 4 hours, or for overnight (about 12 hours).

Following the incubation minicells were spun at 13,200 rpm for 8 minutes, and the supernatant was discarded. The pellets were washed with 1 ml of PBS (pH 7.4) and were centrifuged as above. The supernatant was discarded.

The pellets were resuspended in 0.5 ml of PBS (pH 7.4) and were incubated for 15 minutes at room temperature with rotation. After incubation each sample was applied to a 0.65 μm Centricon® column and was spun at 200 g for 1 minute or until the entire sample flowed through. The flow-through was collected into a fresh tube. A fresh lot of 0.5 ml PBS (pH 7.4) was applied to the same filter and was spun, and the flow-through was added to the original 0.5 ml sample.

The samples were centrifuged at 13,200 rpm for 8 minutes, and the supernatant was discarded. Each sample then was resuspended in 350 μl of PBS (pH 7.4).

Minicell sample counts were performed, with 10 μl minicells in 990 μl PBS (pH 7.4), using the LM20 nanoparticle analysis system, a product of NanoSight Ltd (Amesbury, Wiltshire, UK). The results were as follows:

2 hour: $6.24 \times 10^{10}$/ml
4 hour: $5.77 \times 10^{10}$/ml
Overnight: $5.93 \times 10^{10}$/ml Lots of each sample (20 μl) were spun at 13,200 rpm for 8 minutes and supernatant was removed, followed by HPLC analysis for MTX content in minicell samples.

Via HPLC the amount of MTX loaded into minicells in each sample was measured as the peak area at 251 nm (injection volume: 50 μl). For pairs of duplicate samples (1,2: 2-hour loading; 3,4: 4-hour loading; and 5,6: overnight loading) the results are shown below, including MTX content per sample and the amount of MTX per 10$^9$ minicells.

TABLE 4

| Sample | Area (254 nm) | MTX content per sample (μg) | MTXcontent per 10$^9$ minicells (μg) |
|---|---|---|---|
| 1 | 59644 | 0.563 | 0.452 |
| 2 | 60080 | 0.568 | 0.455 |
| 3 | 58718 | 0.555 | 0.481 |
| 4 | 59241 | 0.560 | 0.485 |
| 5 | 74435 | 0.703 | 0.593 |
| 6 | 66313 | 0.626 | 0.528 |

For samples 5 and 6, with loading overnight, 10$^9$ minicells were loaded on average with about 0.56 g of MTX. This means that each minicell contained about 759,000 MTX molecules, based on a molecular weight of about 444 for the drug, per *The Merck Index Online* (2014).

The concentrations of MTX inside minicells were surprisingly high, comparable to those of doxorubicin, which like MTX is intrinsically fluorescent. See Consoli et al., *Leukemia* 11: 2066-74 (1997), and Bell, *Biochim Biophys Acta* 949: 132-37 (1988) (maximum excitation and emission for MTX at around 610 nm and 685 nm, respectively). See also Smith et al., *Cancer Res.* 52: 4000-08 (1992) (low red fluorescence at 514 nm). Thus, the high loading efficiency of MTX, which is slightly smaller than doxorubicin, is believed to be a function of its fluorescence.

Example 13. Loading of a Fluorescent Compound in the Presence of Ions

This example shows that the presence of ions heightens the fluorescence-mediated enhancement of vesicle loading evidenced by the initial examples. Accordingly, ions from salt disassociation in the vesicle medium are thought to interact with channels in the intact membrane of bacterially derived vesicles (here, minicells) so as to potentiate the above-discussed effect, on movement of a fluorescent compound through the transmembrane channels, of energy transfer between the compound and molecules in or lining the channels.

In keeping with the small-scale protocol, minicells (2.5×$10^{10}$ per tube) were washed once with 1 ml of PBS (pH7.4) and were centrifuged (16,000 g, 7 minutes), and the supernatant was discarded. In 15% ethanol, 85% PBS (pH 7.4), washed minicells were loaded with 100 µg/ml FLUTAX-1 (Tocris Biosciences), either with or without 200 mM KCl (Sigma-Aldrich).

The tubes were rotated at 37° C. One tube from each treatment was removed for washing at each of 15 minutes, 45 minutes, 2 hours and 5 hours. Each treatment was washed three times to remove the reagents and retain the minicells.

FLUTAX-1 levels were measured via HPLC in the manner described above. Thus, measurements (UV 228 nm) were compared to a standard curve of known FLUTAX-1 amounts and were extrapolated to yield the FLUTAX-1 quantity within 1×$10^9$ minicells.

Figure 21:
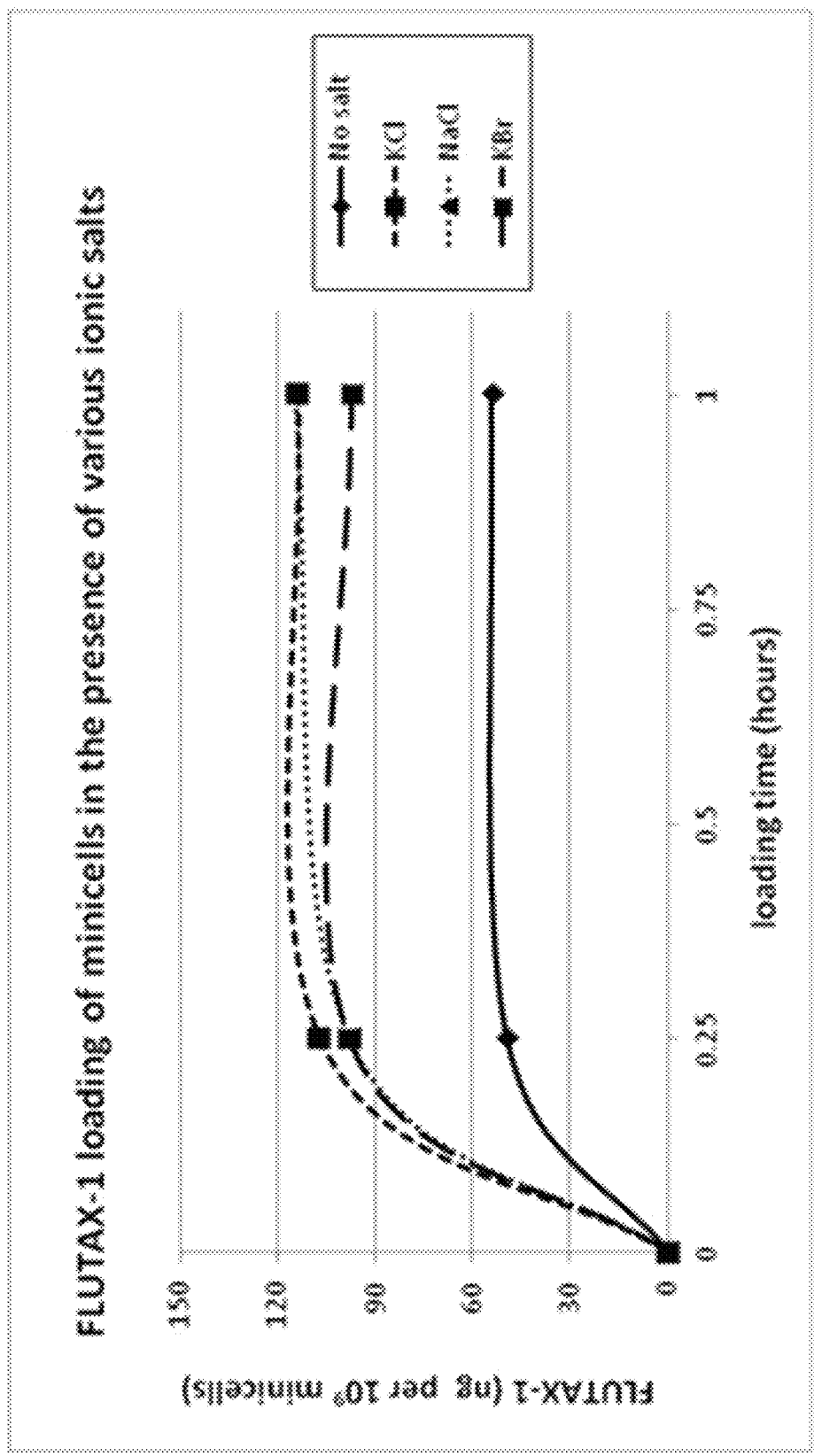
FIG. 21 shows the course and amount FLUTAX-1 loaded into minicells in the presence of ions from dissociation of various ionic salts.

As FIG. 21 depicts, the results show that inclusion of 200 mM KCl in the loading solution dramatically enhanced the loading of FLUTAX-1 into intact minicells. That is, the higher salt concentration was associated with more than a doubling of the quantity of fluorescent drug loaded into the minicells. Indeed, the effect was evident after as little as 15 minutes of minicell/drug co-incubation.

To illuminate whether other ionic salts have this effect, the loading of FLUTAX-1 into minicells was tested in the presence of equimolar amounts of different salts; and loading was measured by HPLC as before. Thus, minicells (2.5×$10^{10}$ per tube) were washed once with 1 ml of PBS (pH7.4) and were centrifuged (16,000 g, 7 minutes), and the supernatant was discarded. Washed minicells were loaded with 100 µg/ml of FLUTAX-1 in 15% ethanol, 85% PBS (pH 7.4), either with or without 200 mM of KCl, NaCl, or KBr. The tubes were rotated at 37° C. One tube from each condition was removed for washing at each of 15 minutes and 1 hour. Each treatment was washed three times as described above.

Minicells were lysed and extracted, as described above, and lysates were run under HPLC conditions for measuring FLUTAX-1 levels. Measurements (UV 228 nm) were compared to a curve of known FLUTAX-1 amounts and were extrapolated to obtain the quantity of FLUTAX-1 in 1×$10^9$ minicells.

Figure 22:
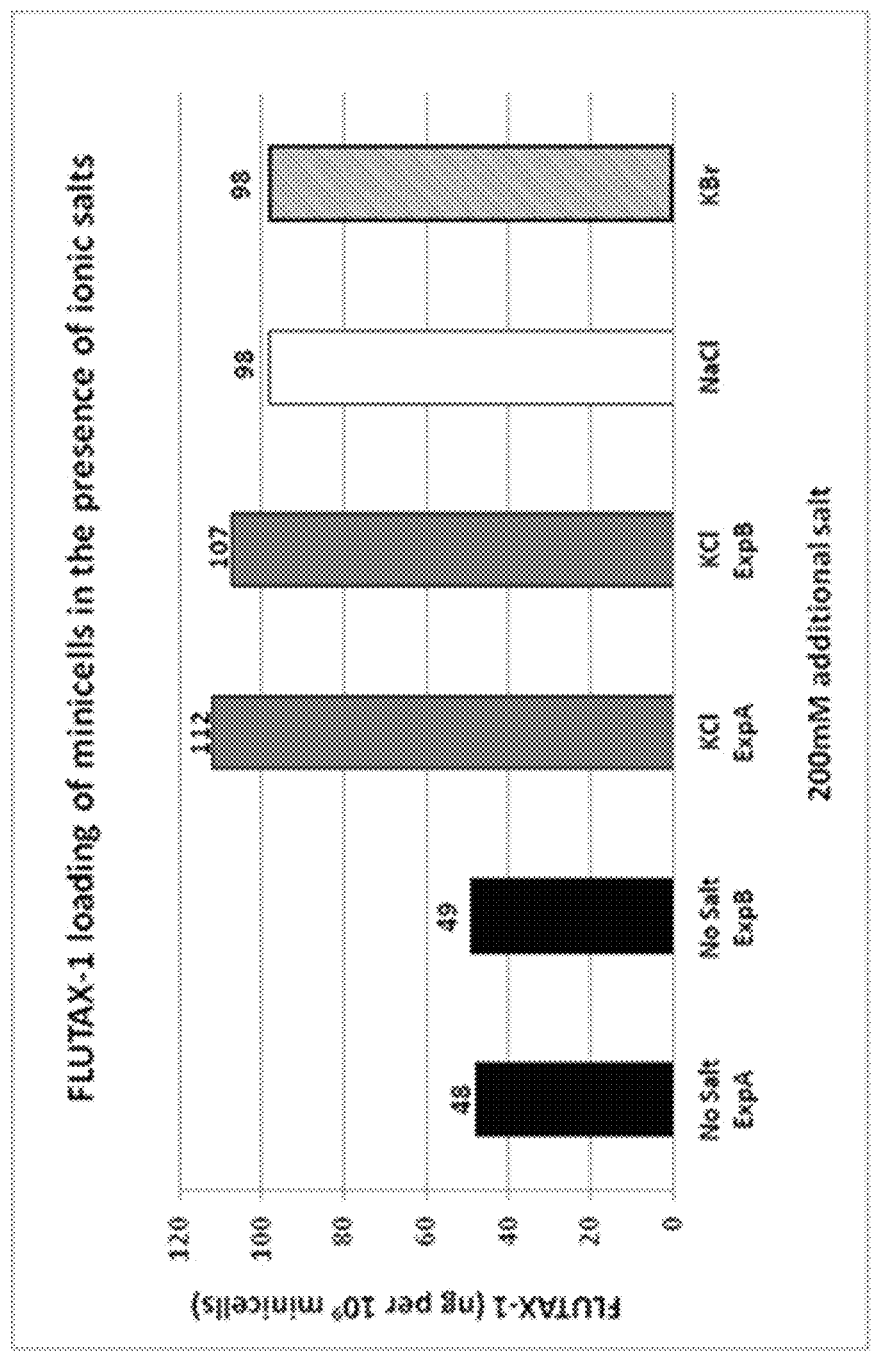
FIG. 22 depicts data shown in FIG. 21 for the time point representing 15 minutes of loading FLUTAX-1 into minicells.

The results are shown in FIG. 21. At 200 mM each of the tested salts dramatically enhanced loading of the fluorescent drug into minicells, with improvement evident at both the 15-minute and the 1-hour time points. The bar chart in FIG. 22 represents the combined data from the 15-minute time point. The same treatments performed in each experiment (e.g., no salt versus 200 mM KCl) provided highly consistent duplicate data.

Each of the salts KCl, NaCl, and KBr increased the efficiency of loading a fluorescent drug into intact, bacterially derived vesicles, here by approximately 2-fold at 15 minutes. Loading was in effect completed within about 4 hours of incubation. These observations underscore that the loading of a fluorescent compound into intact vesicles is enhanced by co-incubating the vesicles and fluorescent compound with positive and/or negative ions added to the external environment. By contrast, there is no such impact of ions on loading of an otherwise similar but non-fluorescent compound.

This ionic effect was found to be influenced by the temperature of co-incubation. For instance, when intact, bacterially derived minicells in HEPES saline buffer (pH 6.8) were prepared and drug-loaded via co-incubation with doxorubicin, essentially as described above, at room temperature (~22° C.) and at ~37° C., respectively, the results from HPLC-based quantification of intra-vesicle doxorubicin levels at different time points were as follows:

TABLE 5

| | ng Dox per $10^9$ EDVs | |
|---|---|---|
| Timepoint (hrs) | 37° C. | RT |
| 0 | 0 | 0 |
| 2 | 1910 | 684 |
| 4 | 2281 | 1009 |
| 6 | 1846 | 1215 |
| 8 | 1886 | 846 |
| 24 | 2957 | 1466 |

Figure 23:
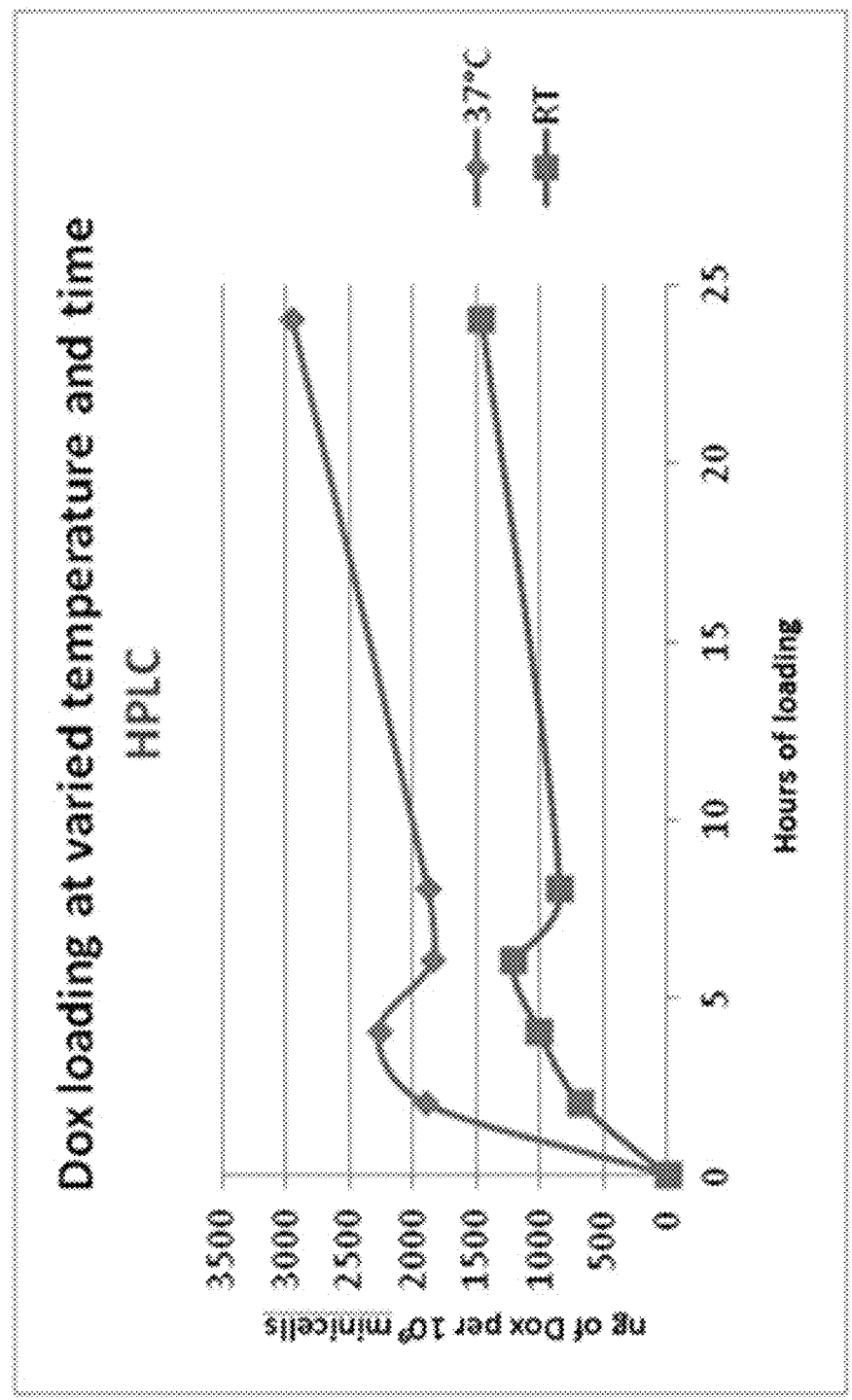
FIG. 23 shows the effect of co-incubation temperature on the enhancement by ions of fluorescence-mediated transmembrane movement of compounds into minicells.

A graphical representation of these data (FIG. 23) shows that the amount of fluorescent compound loaded into the minicells was over 100% greater when co-incubation occurred at about 37° C. than at room temperature. (Membrane degradation renders infeasible any co-incubation temperature much higher than about 37° C.)

Example 14. Advantages of Inventive Large-Scale Process Over Conventional Small-Scale Protocol This example contrasts the small-scale protocol, discussed above in relation to MacDiarmid et al. (2007), with the large-scale process of the present invention. As the example demonstrates, the inventive process afforded surprisingly better consistency and purity for compositions containing intact, bacterially derived vesicles. This is because a large-scale method of the invention significantly reduces not only the endotoxin levels but also the payload compound entrapped outside the vesicle.

Small-Scale Protocol

Intact minicells were prepared and loaded with doxorubicin essentially in accordance with the methodology of MacDiarmid et al. (2007), except that the minicells did not carry any targeting bispecific ligands and, hence, would not be taken up by a targeted host cell. Upon overnight incubation with the drug (about 1 ml/mg) at 37° C. with rotation, the loaded minicells were subjected five times to a washing step that entailed centrifugation (13,200 rpm, 10 minutes) and resuspension of the resultant pellet in 1 ml BSG buffer (pH 7.4).

The washed, doxorubicin-loaded minicells (1×$10^8$) then were incubated with estrogen receptor-negative MDA-MB-468 human breast cancer cells ($10^4$ cells per well) in Gibco RPMI-1640 tissue culture medium (in 0.5 ml per well) supplemented with 10% Fetal Bovine Serum, 2 mM L-glutamine, and 100 U/ml of both penicillin G and streptomycin.

The cells were monitored subsequently every 24 hours via confocal microscopy. Within two days the cancer cells displayed red fluorescence in their nuclei, indicative of doxorubicin entry, even though the loaded minicells had not been targeted for uptake by the cells. Thus, the small-scale protocol resulted in the trapping on the minicell surfaces of extraneous doxorubicin, which leached into the tissue culture medium and entered the cancer cells.

Large-Scale Process

Five batches were prepared independently of minicells that packaged doxorubicin and were targeted with a bispecific ligand that bound EGFR (see MacDiarmid et al. (2007) at page 443, second paragraph under "Experimental Procedures"). In accordance with the large-scale process, the doxorubicin-loaded and EGFR-targeted minicells were subjected to five successive washings with PBS buffer, about 20 liters per washing, over large cross-flow filters.

For each batch of minicells the doxorubicin concentration was determined, as described above, and the level of free endotoxin was measured via a standard LAL assay. See, e.g., Dawson, *LAL Update*, Vol. 22, No. 3 (October 2005). The results are tabulated below.

TABLE 6

| $^{EGFR}$Minicell$_{Dox}$ Batch | Dox Concentration (per $1 \times 10^9$ minicells) | Free Endotoxin Level (EU per $1 \times 10^9$ minicells) |
| --- | --- | --- |
| 1 | 612 ng | 2.25 EU |
| 2 | 688 ng | 2.05 EU |
| 3 | 764 ng | 2.7 EU |
| 4 | 639 ng | 5.55 EU |
| 5 | 659 ng | 2.4 EU |
| Mean value | 672 ng | 2.99 EU |
| Standard deviation | 58 ng | 1.45 EU |

As these results show, the large-scale process provided an average doxorubicin concentration for loaded minicells of about 672 ng±58 ng per $1\times10^9$ minicells. A substantially improved purity achieved with the large-scale process is evidenced by an average free endotoxin level of 2.99 EU±1.45 EU per $1\times10^9$ minicells.

While certain embodiments have been illustrated and described, it should be understood that changes and modifications can be made therein in accordance with ordinary skill in the art without departing from the technology in its broader aspects as defined in the following claims.

The embodiments illustratively described above may suitably be practiced in the absence of any element or elements, limitation or limitations not specifically disclosed. For example, the terms "comprising," "including," "containing," etc. should be read expansively and without limitation. Additionally, the terms and expressions employed here have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this specification. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is to be understood as well that the terminology used herein is for the purpose of describing particular embodiments only and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document specifically and individually were indicated to be incorporated by reference in its entirety. Definitions that are contained in text incorporated by reference are excluded to the extent that they contradict definitions in this disclosure.

Other embodiments are set forth in the claims that follow.

What is claimed is:

1. A composition comprising an intact bacterially derived minicell, wherein:
   (a) the minicell encloses at least about 500,000 molecules of a fluorescent small molecule drug, and
   (b) the fluorescent small molecule drug is not doxorubicin, irinotecan, bisantrene, topotecan, epirubicin, daunorubicin, mitoxantrone, L-alanine, N-[(2',7'-difluoro-3',6'-dihydroxy-3-oxospiro[isobenzofuran-1 (3H),9'-[9H]xanthen]-5-yl)carbonyl]-(2aR,4S,4aS,6R, 9S,11S,12S,12aR,12bS)-6,12b-bis(acetyloxy)-12-(benzoyloxy)-9-[(2R,3S)-3-(benzoylamino)-2-hydroxy-1-oxo-3-phenylpropoxy]-2a,3,4,4a,5,6,9,10, 11,12,12a,12b-dodecahydro-11-hydroxy, or vinblastine conjugated to 4,4-difluoro-5,7-dimethyl-4-bora-3a,4a-diaza-s-indacene.

2. The composition of claim 1, wherein:
   (a) the small molecule drug is biologically active;
   (b) the small molecule drug is cytotoxic;
   (c) the small molecule drug is activated in vivo;
   (d) any combination of (a), (b), and/or (c).

3. The composition of claim 1, wherein the small molecule drug is cytotoxic and:
   (a) the small molecule drug is a morpholinyl anthracycline derivative; or
   (b) the small molecule drug is PNU-159682.

4. A composition comprising an intact and nonliving bacterial vesicle that encloses at least about 500,000 copies a compound of formula D-L-F or a salt thereof, wherein D is the residue of a small molecule drug, L is a linker, and F is a fluorescent moiety, wherein the linker:
   (a) has a half-life of between about 6 hours and about 24 hours; and/or
   (b) is degraded in the endosome of a mammalian cell.

5. The composition of claim 4, wherein the linker is selected from the group consisting of a bond, —OC(O)—(CHR$^{40}$)$_q$NR$^{41}$C(O)—, and —OC(O)—(CHR$^{40}$)$_q$C(O)NR$^{41}$—(CHR$^{42}$)$_u$—NH—C(S)—NH—, wherein R$^{40}$, R$^{41}$ and R$^{42}$ are independently —H or C$_{1-4}$ alkyl, and q and u are independently 1, 2, 3, 4, 5, 6 or 7.

6. The composition of claim 4, wherein the linker is selected from the group consisting of
—O—C(O)—(CH$_2$)NHC(O)— and —O—C(O)—(CH$_2$)$_3$C(O)NH—(CH$_2$)$_6$—NH—C(S)—NH—.

7. The composition of claim 4, wherein the fluorescent moiety is:

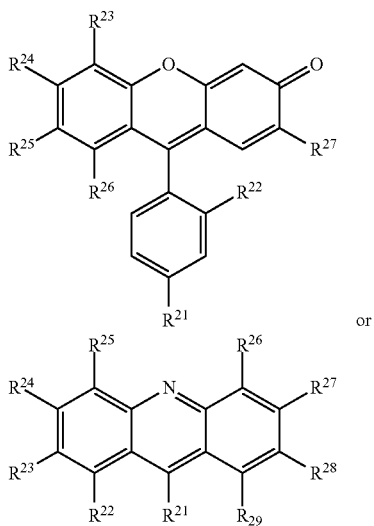

or

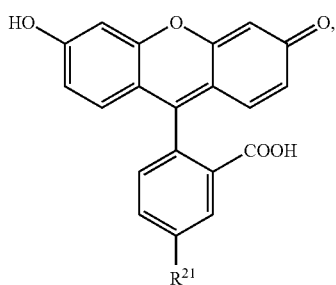

wherein:
R$^{21}$ is —H, —OH, —COOH, —O—C(O)—(C$_{1-4}$ alkyl), —C(O)—O—(C$_{1-4}$ alkyl), C$_{1-4}$ alkoxy, halo, or —R$^d$;

R$^{22}$ is —H, —OH, —COOH, C$_{1-4}$alkyl, substituted C$_{1-4}$ alkyl, C$_{1-4}$ alkoxy, substituted C$_{1-4}$ alkoxy, —O—C(O)—(C$_{1-4}$ alkyl), —O—C(O)-(substituted C$_{1-4}$ alkyl), —C(O)—O—(C$_{1-4}$ alkyl), —C(O)—O-(substituted C$_{1-4}$ alkyl), —O—CH$_2$—O—(C$_{1-4}$ alkyl), —S—CH$_2$—O—(C$_{1-4}$ alkyl), or —R$^d$;

each R$^{23}$, R$^{24}$, R$^{25}$, R$^{26}$, R$^{27}$, R$^{28}$ and R$^{29}$ are independently —H, halo, —OH, —CH$_3$ or —R$^d$, provided at least one of R$^{21}$, R$^{22}$, R$^{23}$, R$^{24}$, R$^{25}$, R$^{26}$, R$^{27}$, R$^{28}$ and R$^{29}$ is —R$^d$; wherein R$^d$ is a point of connection to the linker.

8. The composition of claim 4, wherein the fluorescent moiety is:

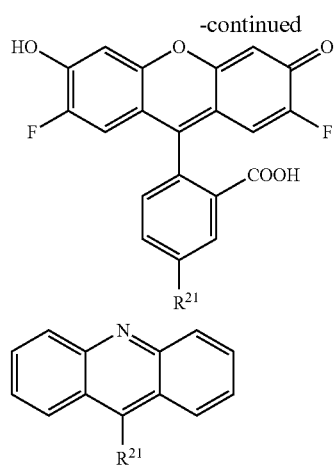

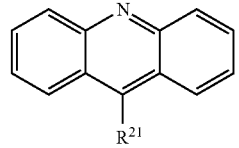

wherein R$^{21}$ is the point of connection to the linker.

9. The composition of claim 4, wherein the fluorescent moiety is:

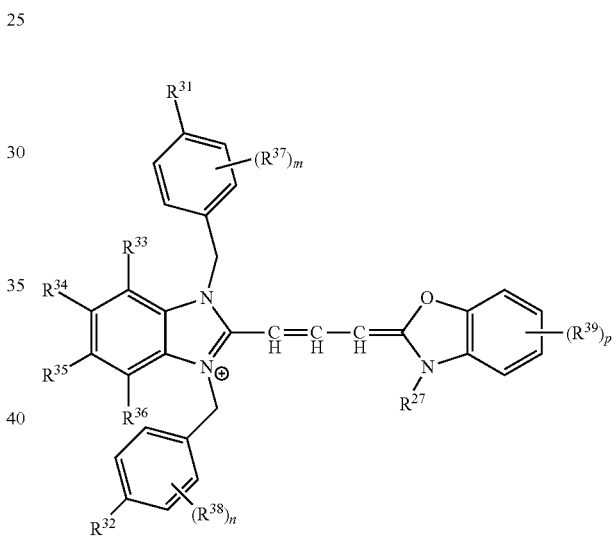

wherein:
R$^{31}$ and R$^{32}$ are independently —H, —OH, C$_{1-4}$ alkyl, C$_{1-4}$ haloalkyl, —O—C(O)—(C$_{1-4}$ alkyl), —C(O)—O—(C$_{1-4}$ alkyl), C$_{1-4}$ alkoxy, halo, or —R$^d$;

R$^{34}$ and R$^{35}$ are independently —H, halo, —OH, —COOH, C$_{1-4}$alkyl, substituted C$_{1-4}$ alkyl, C$_{1-4}$ alkoxy, —O—C(O)—(C$_{1-4}$ alkyl), —C(O)—O—(C$_{1-4}$ alkyl), —O—CH$_2$—O—(C$_{1-4}$ alkyl), —S—CH$_2$—O—(C$_{1-4}$ alkyl), or —R$^d$;

each R$^{33}$ and R$^{36}$ is independently —H, halo, —OH, —CH$_3$ or —R$^d$;

each R$^{37}$, R$^{38}$ and R$^{39}$ is independently halo, —OH, —CH$_3$ or —R$^d$;

each m, n, and p is independently 0, 1, 2, 3 or 4;

provided at least one of R$^{31}$, R$^{32}$, R$^{34}$, R$^{34}$, R$^{35}$, R$^{36}$, R$^{37}$, R$^{38}$ and R$^{39}$ is —R$^d$; wherein R$^d$ is a point of connection to the linker.

10. The composition of claim 9, wherein the fluorescent moiety is:

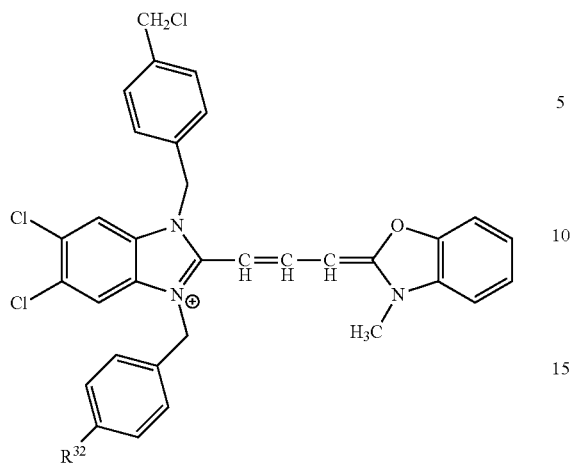
wherein $R^{32}$ is the point of connection to the linker.
11. A method for treating cancer in a patient in need thereof, comprising administering to the patient an effective amount of a composition of claim 1, wherein the compound is cytotoxic.
12. The composition of claim 4, wherein the intact and nonliving bacterial vesicle is an intact bacterially derived minicell.
* * * * *